US008916573B2

(12) United States Patent
Hubschwerlen et al.

(10) Patent No.: US 8,916,573 B2
(45) Date of Patent: Dec. 23, 2014

(54) QUINAZOLINE-2,4-DIONE DERIVATIVES

(75) Inventors: Christian Hubschwerlen, Allschwil (CH); Georg Rueedi, Allschwil (CH); Jean-Philippe Surivet, Allschwil (CH); Cornelia Zumbrunn Acklin, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 14/238,415

(22) PCT Filed: Aug. 10, 2012

(86) PCT No.: PCT/IB2012/054080
§ 371 (c)(1),
(2), (4) Date: Feb. 11, 2014

(87) PCT Pub. No.: WO2013/021363
PCT Pub. Date: Feb. 14, 2013

(65) Prior Publication Data
US 2014/0171425 A1    Jun. 19, 2014

(30) Foreign Application Priority Data

Aug. 11, 2011    (WO) .................. PCT/IB2011/053583

(51) Int. Cl.
A01N 43/54    (2006.01)
A61K 31/517   (2006.01)
C07D 239/72   (2006.01)
C07D 401/00   (2006.01)

(52) U.S. Cl.
USPC ...................... 514/266.1; 544/283

(58) Field of Classification Search
USPC ...................... 544/283; 514/266.1
See application file for complete search history.

(56) References Cited

U.S. PATENT DOCUMENTS

| 8,114,867 | B2 | 2/2012 | Gude et al. |
| 8,217,029 | B2 | 7/2012 | Bur et al. |
| 8,349,828 | B2 | 1/2013 | Hubschwerlen et al. |
| 8,618,092 | B2 | 12/2013 | Hubschwerlen et al. |
| 2003/0105118 | A1 | 6/2003 | Masumoto et al. |
| 2006/0205719 | A1 | 9/2006 | Hubschwerlen et al. |
| 2007/0060558 | A1 | 3/2007 | Sanchez et al. |

FOREIGN PATENT DOCUMENTS

| WO | 98/42688 | 10/1998 |
| WO | 01/79206 | 10/2001 |
| WO | 2004/089947 | 10/2004 |
| WO | 2005/049605 | 6/2005 |
| WO | 2006/024741 | 3/2006 |
| WO | 2006/134378 | 12/2006 |
| WO | 2007/070359 | 6/2007 |
| WO | 2008/126024 | 10/2008 |
| WO | 2008/126034 | 10/2008 |
| WO | 2009/104147 | 8/2009 |
| WO | 2009/104159 | 8/2009 |
| WO | 2010/015985 | 2/2010 |
| WO | 2010/041194 | 4/2010 |
| WO | 2010/041219 | 4/2010 |
| WO | 2010/046388 | 4/2010 |
| WO | 2010/079206 | 7/2010 |

OTHER PUBLICATIONS

Bellina et al., "Palladium Catalysts for the Suzuki Cross-Coupling Reaction: An Overview of Recent Advances", Synthesis (2004), No. 15, pp. 2419-2440.
Benz, G., "Synthesis of Amides and Related Compounds" in Comprehensive Organic Synthesis, 1st Ed. (1991), vol. 6, pp. 381-417.
Cha et al., "Acyclic Stereocontrol Induced by Allylic Alkoxy Groups. Synthetic Applications of Stereoselective Dihydroxylation in Natural Product Synthesis", Chem. Rev. (1995), vol. 95, pp. 1761-1795.
Chang et al., "Triazolinones as Nonpeptide Angiotensin II Antagonists. 1. Synthesis and Evaluation of Potent 2,4,5-Trisubstituted Triazolinones", J. Med. Chem. (1993), vol. 36, No. 17, pp. 2558-2568.
de Meijere et al., "Fine Feathers Make Fine Birds: The Heck Reaction in Modern Garb", Angew. Chem. Int. Ed. Engl. (1994), vol. 33, pp. 2379-2411.
Doyle et al., "Enantioselective Alkylations of Tributyltin Enolates Catalyzed by Cr(salen)Cl: Access to Enantiomerically Enriched All-Carbon Quaternary Centers", J. Am. Chem. Soc. (2005), vol. 127, No. 1, pp. 62-63.
Fu, G.C., "The Development of Versatile Methods for Palladium-Catalyzed Coupling Reactions of Aryl Electrophiles through the Use of P(t-Bu)3 and PCy3 as Ligands", Acc. Chem. Res. (2008), vol. 41, No. 11, pp. 1555-1564.
Gould, P.L., "Salt selection for basic drugs", Int. J. Pharm. (1986), vol. 33, pp. 201-217.
Greene et al., Protective Groups in Organic Synthesis, 3rd Ed. (1999) (3 pages).
Greene et al., Protective Groups in Organic Synthesis, 3rd Ed. (1999), pp. 23-147.
Greene et al., Protective Groups in Organic Synthesis, 3rd Ed. (1999), pp. 494-653.
Heck, R.F., "Palladium-Catalyzed Vinylation of Organic Halides", Organic Reactions (1982), vol. 27, pp. 345-391.

(Continued)

*Primary Examiner* — Paul V. Ward
(74) *Attorney, Agent, or Firm* — Hunton & Williams LLP

(57) ABSTRACT

The invention relates to antibacterial compounds of formula (I), wherein $R^1$ is H, halogen, $(C_1-C_3)$alkyl or $(C_1-C_3)$alkoxy; $R^2$ is H, halogen, $(C_1-C_3)$alkyl, $(C_1-C_3)$alkoxy or pyrrolidin-1-yl; $R^3$ is H, halogen, $(C_1-C_3)$alkyl, $(C_1-C_3)$alkoxy, vinyl or 2-methoxycarbonyvinyl or $R^2$ and $R^3$ together with the two carbon atoms which bear them form a phenyl ring; $R^4$ is H, halogen, $(C_1-C_3)$alkyl or $(C_1-C_3)$alkoxy; and $R^5$ is H, $(C_1-C_3)$alkyl or cyclopropyl, or $R^4$ and $R^5$ form together a —$CH_2CH_2CH_2$— group; A is the divalent group —$CH_2$—, —$CH_2CH_2$—, #—$CH(OH)CH_2$—*, #—$CH_2N(R^6)$—* and —$CH_2NHCH_2$—, wherein # indicates the point of attachment to the optionally substituted (quinazoline-2,4-dione-3-yl)methyl residue and * represents the point of attachment to the substituted (oxazolidinon-4-yl)methyl residue; $R^6$ is H or acetyl; Y is CH or N; and Q is O or S; and salts of such compounds.

15 Claims, No Drawings

(56) References Cited

OTHER PUBLICATIONS

Herndon et al., "Ketanserin Analogues: Structure-Affinity Relationships for 5-HT2 and 5-HT1C Serotonin Receptor Binding", J. Med. Chem. (1992), vol. 35, pp. 4903-4910.

Kantchev et al., "Pd-N-Heterocyclic Carbene (NHC) Catalysts for Cross-Coupling Reactions", Aldrichimica ACTA (2006), vol. 39, No. 4, pp. 97-111.

Klapars et al., "A General and Efficient Copper Catalyst for the Amidation of Aryl Halides", J. Am. Chem. Soc. (2002), vol. 124, pp. 7421-7428.

Larock, R.C., Comprehensive Organic Transformations, A Guide to Functional Group Preparations, 2nd Ed. (1999), pp. 779-784.

Larock, R.C., Comprehensive Organic Transformations, A Guide to Functional Group Preparations, 2nd Ed. (1999), pp. 1941-1949.

Mauger et al., "Synthetic Applications of Buchwald's Phosphines in Palladium-Catalyzed Aromatic-Bond-Forming Reactions", Aldrichimica ACTA (2006), vol. 39, No. 1, pp. 17-24.

Mitsunobu, O., "The Use of Diethyl Azodicarboxylate and Triphenylphosphine in Synthesis and Transformation of Natural Products", Synthesis (1981), pp. 1-28.

Miyaura et al., "Palladium-Catalyzed Cross-Coupling Reactions of Organoboron Compounds", Chem. Rev. (1995), vol. 95, No. 7, pp. 2457-2483.

Remington: The Science and Practice of Pharmacy, 21st Ed. (2005) (5 pages). (Table of Contents).

Sato et al., "One-pot reductive amination of aldehydes and ketones with -picoline-borane in methanol, in water, and in neat conditions", Tetrahedron (2004), vol. 60, pp. 7899-7906.

Shen et al., "Highly Reactive, General, and Long-Lived Catalysts for Coupling Heteroaryl and Aryl Chlorides with Primary Nitrogen Nucleophiles", Angew. Chem. Int. Ed. (2005), vol. 44, pp. 1371-1375.

Surry et al., "Biaryl Phosphane Ligands in Palladium-Catalyzed Amination", Angew. Chem. Int. Ed. (2008), vol. 47, pp. 6338-6361.

Thompson et al., "Direct Conversion of Activated Alcohols to Azides Using Diphenyl Phosphorazidate. A Practical Alternative to Mitsunobu Conditions", J. Org. Chem. (1993), vol. 58, pp. 5886-5888.

Wolfe et al., "Scope and Limitations of the Pd/BINAP-Catalyzed Amination of Aryl Bromides", J. Org. Chem. (2000), vol. 65, No. 4, pp. 1144-1157.

International Search Report issued in corresponding International Application No. PCT/IB2012/054080 mailed Dec. 13, 2012.

Written Opinion issued in corresponding International Application No. PCT/IB2012/054080 mailed Dec. 13, 2012.

QUINAZOLINE-2,4-DIONE DERIVATIVES

CROSS-REFERENCE TO RELATED APPLICATIONS

This application is a §371 National Stage of International Application No. PCT/IB2012/054080, filed Aug. 10, 2012, which claims the benefit of priority from International Application No. PCT/IB2011/053583, filed Aug. 11, 2011, the contents of which are hereby incorporated by reference in their entirety.

FIELD OF THE INVENTION

The present invention concerns quinazoline-2,4-dione antibiotic compounds, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram-positive and Gram-negative aerobic and anaerobic bacteria and mycobacteria.

BACKGROUND OF THE INVENTION

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immuno-compromised patients.

BRIEF SUMMARY OF THE INVENTION

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:

- *S. aureus* is resistant to β-lactams, quinolones and now even to vancomycin;
- *S. pneumoniae* is becoming resistant to penicillin or quinolone antibiotics and even to new macrolides;
- *Enteroccocci* are quinolone and vancomycin resistant and β-lactam antibiotics are inefficacious against these strains;
- *Enterobacteriacea* are cephalosporin and quinolone resistant;
- *P. aeruginosa* are β-lactam and quinolone resistant.

Furthermore, the incidence of multi-drug-resistant Gram-negative strains such as *Enterobacteriacae* and *Pseudomonas aeruginosa*, is steadily increasing and new emerging organisms like *Acinetobacter* spp. or *Clostridium difficile*, which have been selected during therapy with the currently used antibiotics, are becoming a real problem in hospital settings. Therefore, there is a high medical need for new antibacterial agents which overcome these multidrug-resistant bacilli.

In addition, microorganisms that are causing persistent infections are increasingly being recognized as causative agents or cofactors of severe chronic diseases like peptic ulcers or heart diseases.

WO 2010/041219 describes antibacterial compounds of formula (A1)

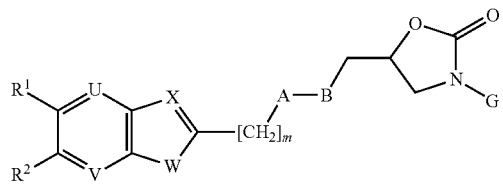

(A1)

wherein
$R^1$ represents hydrogen, $(C_{1-4})$alkoxy or halogen;
$R^2$ represents hydrogen or $(C_{1-4})$alkoxy;
U represents N or CH;
V represents N or $CR^b$, wherein $R^b$ is hydrogen or halogen;
W represents *—CH=$CR^a$—, *—N=CH— or S, wherein the asterisks indicate the bond which is linked to the carbon atom connecting V and W and wherein $R^a$ represents hydrogen or halogen;
X represents N or $CR^c$, wherein $R^c$ is hydrogen, $(C_{1-4})$alkyl or halogen;
with the proviso that the group of formula (D)

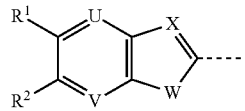

(D)

contains between none and three heteroatoms, wherein the heteroatoms are independently selected from nitrogen and, in case of W, sulfur;
m represents 1, A represents —NHCH$_2$—#, —CH$_2$NH—#, —NHCH$_2$CH$_2$—#, —CH$_2$NHCH$_2$—, —CH$_2$CH$_2$NH—#, —NHCH$_2$CH$_2$NH—, —CH$_2$NHCH$_2$CH$_2$—# or piperazin-1,4-diyl, wherein the hash indicates the bond which is linked to B, and B represents a bond; or
m can notably represent 0, A can then notably represent —NHCH$_2$CH$_2$NHCH$_2$—# wherein the hash indicates the bond which is linked to B, and B represents a bond; and
G can notably represent a group of the formula (G1)

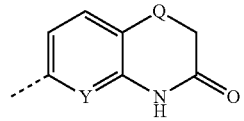

(G1)

wherein Y represents CH or N, and Q represents O or S.
WO 2009/104159 describes antibacterial compounds of formula (A2)

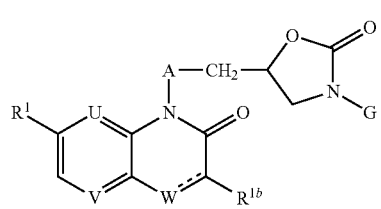

(A2)

wherein
"-----" is a bond or is absent;
$R^1$ represents $(C_1-C_4)$alkoxy or halogen;
$R^{1b}$ represents H or $(C_1-C_3)$alkyl;
U and V each independently represent CH or N;

W represents CH or N, or, in case "----" is absent, W represents CH₂ or NH; with the proviso that at least one of U, V and W represents CH or CH₂;
A represents —CH₂—CH(R²)—B—NH—* or —CH(R³)—CH₂—N(R⁴)—[CH₂]ₘ—*; wherein the asterisks indicate the bond which is linked via the CH₂-group to the oxazolidinone moiety;
B represents CH₂ or CO;
R² represents hydrogen, OH or NH₂;
R³ and R⁴ both represent hydrogen, or R³ and R⁴ together form a methylene bridge; m represents the integer 0, 1 or 2; and
G represents notably a group of the formula G⁵ drawn below

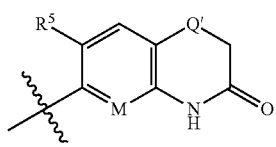

G⁵ wherein M represents CH or N, Q' represents O or S and R⁵ represents hydrogen or fluorine.

US 2007/0060558 discloses antibacterial compounds having the formula (A3)

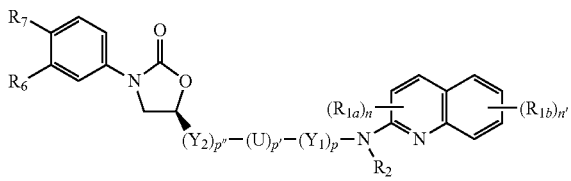

(A3)

wherein
n and n' each independently represent 0, 1, 2 or 3;
R₁ₐ and R₁ᵦ can (notably) each independently represent halogen, (C₁-C₆)alkyl or (C₁-C₆)alkoxy;
R₂ can notably represent H;
the group —(Y₁)ₚ—(U)ₚ—(Y₂)ₚ″— can notably represent 2-ethylamino, 2-propylamino or 3-propylamino;
R₆ and R₇ can (among other possibilities) form together a cyclic structure.

WO 2006/134378 discloses antibacterial compounds having the formula (A4)

L-U₁-M-U₂—R     (A4)

wherein
L can notably represent the group

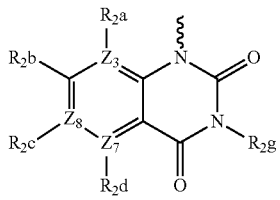

wherein Z₃, Z₆ and Z₇ can each notably be C, R₂a, R₂b, R₂c and R₂d can each notably be independently H, halogen, (C₁-C₆)alkyl or (C₁-C₆)alkoxy, and R₂g can notably be H or (C₁-C₆)alkyl;

U₁ can notably be —CH₂CH₂— or —CH₂CH₂CH₂—;
M is one of the groups

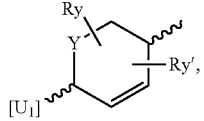

M1

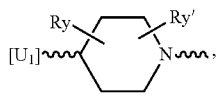

M2

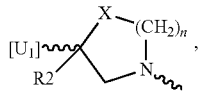

M3

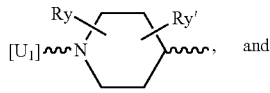

M4

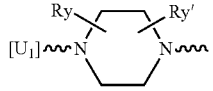

M5 wherein R2 is H or carboxy, " ⌇ " indicate points of attachment, Ry and Ry' can notably be H, X and Y are each independently CH₂, O or NR' wherein, "----" is a bond or is absent, n is 1, 2 or 3;
when M is a group M1 or M4, U₂ is NR'—W wherein W is notably CH₂, CO or CH₂CH₂;
when M is a group M2, M3 or M5, U₂ is W wherein W is as defined above;
when W is CH₂ or CO, R is an optionally substituted aryl, heteroaryl, heterocyclyl or ortho-fused bicyclic heteroaryl, or when W is CH₂CH₂, R is an optionally substituted aryl, heteroaryl, heteroaryloxy, heteroarylthio, heteroarylsulfinyl, heteroarylsulfonyl or heteroarylamino; and
R' at each occurrence can notably be H or (C₁-C₆)alkyl.

Besides, WO 2010/046388 describes antibacterial compounds having the formula (A5)

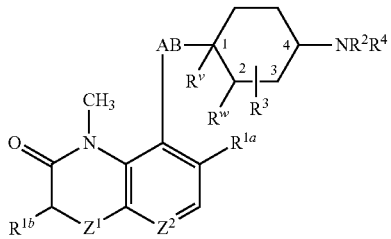

(A5)

wherein
Z¹ and Z² are each independently N or CH; AB is OCH₂, CH₂O, NR¹¹CH₂ or CH₂NR¹¹;
R¹¹ can notably be H, (C₁-C₂)alkyl or formyl;
R¹ᵃ can notably be H, halogen, (C₁-C₆)alkyl or (C₁-C₆)alkoxy;
R¹ᵇ is H or F;
R² is H;
Rᵛ, Rʷ and R³ can notably each be H;

$R^4$ is $UR^5$ wherein U is CO or $CH_2$ and $R^5$ can (for example) be the group

→showing the point of attachment, which group can optionally be substituted.

The instant invention provides new antibacterial compounds based on a quinazoline-2,4-dione motif, namely the compounds of formula I described herein.

Various embodiments of the invention are presented hereafter:

DETAILED DESCRIPTION OF PREFERRED EMBODIMENTS

1) The invention firstly relates to compounds of formula I

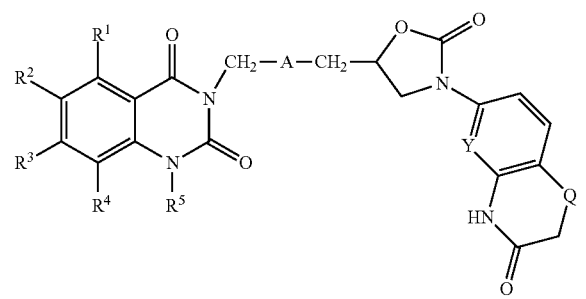

wherein
$R^1$ is H, halogen, $(C_1-C_3)$alkyl or $(C_1-C_3)$alkoxy;
$R^2$ is H, halogen, $(C_1-C_3)$alkyl, $(C_1-C_3)$alkoxy or pyrrolidin-1-yl;
$R^3$ is H, halogen, $(C_1-C_3)$alkyl, $(C_1-C_3)$alkoxy, vinyl or 2-methoxycarbonylvinyl or $R^2$ and $R^3$ together with the two carbon atoms which bear them form a phenyl ring;
$R^4$ is H, halogen, $(C_1-C_3)$alkyl or $(C_1-C_3)$alkoxy and $R^5$ is H, $(C_1-C_3)$alkyl or cyclopropyl, or $R^4$ and $R^5$ form together a —$CH_2CH_2CH_2$— group;
A is the divalent group —$CH_2$—, —$CH_2CH_2$—, #—CH(OH)$CH_2$—*, #—$CH_2N(R^6)$—* or —$CH_2NHCH_2$—, wherein # indicates the point of attachment to the optionally substituted (quinazoline-2,4-dione-3-yl)methyl residue and * represents the point of attachment to the substituted (oxazolidinon-4-yl)methyl residue;
$R^6$ is H or acetyl;
Y is CH or N; and
Q is O or S;
and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a straight or branched chain alkyl group containing from one to four carbon atoms. The term "$(C_1-C_x)$alkyl" (x being an integer) refers to a straight or branched chain alkyl group containing 1 to x carbon atoms. For example, a $(C_1-C_4)$alkyl group contains from one to four carbon atoms. Representative examples of alkyl groups include methyl, ethyl, propyl, iso-propyl, n-butyl, iso-butyl, sec-butyl and tert-butyl. Preferred are methyl and ethyl. Most preferred is methyl.

The term "alkoxy", used alone or in combination, refers to a straight or branched chain alkoxy group containing from one to four carbon atoms. The term "$(C_x-C_y)$alkoxy" (x and y each being an integer) refers to an alkoxy group as defined before containing x to y carbon atoms. For example, a $(C_1-C_3)$alkoxy group contains from one to three carbon atoms. Representative examples of alkoxy groups include methoxy, ethoxy, n-propoxy and iso-propoxy. Preferred are methoxy and ethoxy. Most preferred is methoxy.

The term "halogen" refers to fluorine, chlorine, bromine or iodine, and preferably to fluorine or chlorine.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

In this text, a bond interrupted by a wavy line shows a point of attachment of the radical drawn to the rest of the molecule. For example, the radical drawn below

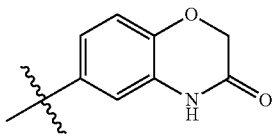 [SMILES: *c1ccc2c(c1)NC(=O)CO2]

is the 3-oxo-3,4-dihydro-2H-benzo[b][1,4]oxazin-6-yl group.

Besides, the term "room temperature" as used herein refers to a temperature of 25° C. Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

2) According to one main embodiment of this invention, the compounds of formula I as defined in embodiment 1) will be such that Y is CH.

3) One sub-embodiment of embodiment 2) relates to the compounds of formula I as defined in embodiment 2) wherein Q is O.

4) Another sub-embodiment of embodiment 2) relates to the compounds of formula I as defined in embodiment 2) wherein Q is S.

5) According to another main embodiment of this invention, the compounds of formula I as defined in embodiment 1) will be such that Y is N.

6) One sub-embodiment of embodiment 5) relates to the compounds of formula I as defined in embodiment 5) wherein Q is O.

7) Another sub-embodiment of embodiment 5) relates to the compounds of formula I as defined in embodiment 5) wherein Q is S.
8) A further embodiment of this invention relates to the compounds of formula I as defined in one of embodiments 1) to 7) wherein A is the divalent group —$CH_2$—.
9) One sub-embodiment of embodiment 8) relates to the compounds of formula I as defined in embodiment 8) wherein $R^1$ is H.
10) According to a particular variant of embodiment 9), the compounds of formula I as defined in embodiment 9) will be such that $R^4$ is halogen or ($C_1$-$C_3$)alkyl (and notably chlorine or methyl).
11) Another sub-embodiment of embodiment 8) relates to the compounds of formula I as defined in embodiment 8) wherein $R^2$ is H.
12) According to a particular variant of embodiment 11), the compounds of formula I as defined in embodiment 11) will be such that $R^3$ is H.
13) According to a particular variant of embodiment 12), the compounds of formula I as defined in embodiment 12) will be such that:
one of $R^1$ and $R^4$ is independently halogen or ($C_1$-$C_3$)alkyl (and notably chlorine or methyl) and the other is H; or
each of $R^1$ and $R^4$ is independently halogen (and notably each of $R^1$ and $R^4$ is chlorine).
14) In a preferred sub-embodiment, the compounds of embodiment 12) or 13) will be such that $R^5$ is methyl.
15) According to another particular variant of embodiment 12), the compounds of formula I as defined in embodiment 12) will be such that $R^4$ and $R^5$ form together a —$CH_2CH_2CH_2$— group.
16) A further sub-embodiment of embodiment 8) relates to the compounds of formula I as defined in embodiment 8) wherein $R^3$ is H.
17) Yet a further sub-embodiment of embodiment 8) relates to the compounds of formula I as defined in embodiment 8) wherein $R^4$ is H.
18) According to a particular variant of embodiment 17), the compounds of formula I as defined in embodiment 17) will be such that $R^1$ is halogen or ($C_1$-$C_3$)alkyl (and notably chlorine or methyl).
19) Yet a further embodiment of this invention relates to the compounds of formula I as defined in one of embodiments 1) to 7) wherein A is the divalent group —$CH_2CH_2$—.
20) One sub-embodiment of embodiment 19) relates to the compounds of formula I as defined in embodiment 19) wherein $R^1$ is H.
21) According to a particular variant of embodiment 20), the compounds of formula I as defined in embodiment 20) will be such that $R^4$ is halogen or ($C_1$-$C_3$)alkyl (and notably chlorine or methyl).
22) Another sub-embodiment of embodiment 19) relates to the compounds of formula I as defined in embodiment 19) wherein $R^2$ is H.
23) According to a particular variant of embodiment 22), the compounds of formula I as defined in embodiment 22) will be such that $R^3$ is H.
24) According to a particular variant of embodiment 23), the compounds of formula I as defined in embodiment 23) will be such that:
one of $R^1$ and $R^4$ is independently halogen or ($C_1$-$C_3$)alkyl (and notably chlorine or methyl) and the other is H; or
each of $R^1$ and $R^4$ is independently halogen (and notably each of $R^1$ and $R^4$ is chlorine).
25) In a preferred sub-embodiment, the compounds of embodiment 23) or 24) will be such that $R^5$ is methyl.
26) According to another particular variant of embodiment 23), the compounds of formula I as defined in embodiment 23) will be such that $R^4$ and $R^5$ form together a —$CH_2CH_2CH_2$— group.
27) A further sub-embodiment of embodiment 19) relates to the compounds of formula I as defined in embodiment 19) wherein $R^3$ is H.
28) Yet a further sub-embodiment of embodiment 19) relates to the compounds of formula I as defined in embodiment 19) wherein $R^4$ is H.
29) According to a particular variant of embodiment 28), the compounds of formula I as defined in embodiment 28) will be such that $R^1$ is halogen or ($C_1$-$C_3$)alkyl (and notably chlorine or methyl).
30) Yet another embodiment of this invention relates to the compounds of formula I as defined in one of embodiments 1) to 7) wherein A is the divalent group #—CH(OH)$CH_2$—*.
31) One sub-embodiment of embodiment 30) relates to the compounds of formula I as defined in embodiment 30) wherein $R^1$ is H.
32) According to a particular variant of embodiment 31), the compounds of formula I as defined in embodiment 31) will be such that $R^4$ is halogen or ($C_1$-$C_3$)alkyl (and notably chlorine or methyl).
33) Another sub-embodiment of embodiment 30) relates to the compounds of formula I as defined in embodiment 30) wherein $R^2$ is H.
34) According to a particular variant of embodiment 33), the compounds of formula I as defined in embodiment 33) will be such that $R^3$ is H.
35) According to a particular variant of embodiment 34), the compounds of formula I as defined in embodiment 34) will be such that:
one of $R^1$ and $R^4$ is independently halogen or ($C_1$-$C_3$)alkyl (and notably chlorine or methyl) and the other is H; or
each of $R^1$ and $R^4$ is independently halogen (and notably each of $R^1$ and $R^4$ is chlorine).
36) In a preferred sub-embodiment, the compounds of embodiment 34) or 35) will be such that $R^5$ is methyl.
37) According to another particular variant of embodiment 34), the compounds of formula I as defined in embodiment 34) will be such that $R^4$ and $R^5$ form together a —$CH_2CH_2CH_2$— group.
38) A further sub-embodiment of embodiment 30) relates to the compounds of formula I as defined in embodiment 30) wherein $R^3$ is H.
39) Yet a further sub-embodiment of embodiment 30) relates to the compounds of formula I as defined in embodiment 30) wherein $R^4$ is H.
40) According to a particular variant of embodiment 39), the compounds of formula I as defined in embodiment 39) will be such that $R^1$ is halogen or ($C_1$-$C_3$)alkyl (and notably chlorine or methyl).
41) Yet another embodiment of this invention relates to the compounds of formula I as defined in one of embodiments 1) to 7) wherein A is the divalent group #—$CH_2N(R^6)$—* (and in particular wherein A is the divalent group #—$CH_2NH$—*).
42) One sub-embodiment of embodiment 41) relates to the compounds of formula I as defined in embodiment 41) wherein $R^1$ is H.
43) According to a particular variant of embodiment 42), the compounds of formula I as defined in embodiment 42) will be such that $R^4$ is halogen or ($C_1$-$C_3$)alkyl (and notably chlorine or methyl).

44) Another sub-embodiment of embodiment 41) relates to the compounds of formula I as defined in embodiment 41) wherein $R^2$ is H.
45) According to a particular variant of embodiment 44), the compounds of formula I as defined in embodiment 44) will be such that $R^3$ is H.
46) According to a particular variant of embodiment 45), the compounds of formula I as defined in embodiment 45) will be such that:
one of $R^1$ and $R^4$ is independently halogen or $(C_1$-$C_3)$alkyl (and notably chlorine or methyl) and the other is H; or
each of $R^1$ and $R^4$ is independently halogen (and notably each of $R^1$ and $R^4$ is chlorine).
47) In a preferred sub-embodiment, the compounds of embodiment 45) or 46) will be such that $R^5$ is methyl.
48) According to another particular variant of embodiment 45), the compounds of formula I as defined in embodiment 45) will be such that $R^4$ and $R^5$ form together a —$CH_2CH_2CH_2$— group.
49) A further sub-embodiment of embodiment 41) relates to the compounds of formula I as defined in embodiment 41) wherein $R^3$ is H.
50) Yet a further sub-embodiment of embodiment 41) relates to the compounds of formula I as defined in embodiment 41) wherein $R^4$ is H.
51) According to a particular variant of embodiment 50), the compounds of formula I as defined in embodiment 50) will be such that $R^1$ is halogen or $(C_1$-$C_3)$alkyl (and notably chlorine or methyl).
52) Yet another embodiment of this invention relates to the compounds of formula I as defined in one of embodiments 1) to 7) wherein A is the divalent group —$CH_2NHCH_2$—.
53) One sub-embodiment of embodiment 52) relates to the compounds of formula I as defined in embodiment 52) wherein $R^1$ is H.
54) According to a particular variant of embodiment 53), the compounds of formula I as defined in embodiment 53) will be such that $R^4$ is halogen or $(C_1$-$C_3)$alkyl (and notably chlorine or methyl).
55) Another sub-embodiment of embodiment 52) relates to the compounds of formula I as defined in embodiment 52) wherein $R^2$ is H.
56) According to a particular variant of embodiment 55), the compounds of formula I as defined in embodiment 55) will be such that $R^3$ is H.
57) According to a particular variant of embodiment 56), the compounds of formula I as defined in embodiment 56) will be such that:
one of $R^1$ and $R^4$ is independently halogen or $(C_1$-$C_3)$alkyl (and notably chlorine or methyl) and the other is H; or
each of $R^1$ and $R^4$ is independently halogen (and notably each of $R^1$ and $R^4$ is chlorine).
58) In a preferred sub-embodiment, the compounds of embodiment 56) or 57) will be such that $R^5$ is methyl.
59) According to another particular variant of embodiment 56), the compounds of formula I as defined in embodiment 56) will be such that $R^4$ and $R^5$ form together a —$CH_2CH_2CH_2$— group.
60) A further sub-embodiment of embodiment 52) relates to the compounds of formula I as defined in embodiment 52) wherein $R^3$ is H.
61) Yet a further sub-embodiment of embodiment 52) relates to the compounds of formula I as defined in embodiment 52) wherein $R^4$ is H.
62) According to a particular variant of embodiment 61), the compounds of formula I as defined in embodiment 61) will be such that $R^1$ is halogen or $(C_1$-$C_3)$alkyl (and notably chlorine or methyl).
63) A further embodiment of this invention relates to the compounds of formula I as defined in one of embodiments 1) to 7) wherein $R^1$ is H.
64) Yet a further embodiment of this invention relates to the compounds of formula I as defined in one of embodiments 1) to 7) wherein $R^1$ is halogen (and notably chlorine).
65) Another embodiment of this invention relates to the compounds of formula I as defined in one of embodiments 1) to 7) wherein $R^1$ is $(C_1$-$C_3)$alkyl (and notably methyl).
66) Yet another embodiment of this invention relates to the compounds of formula I as defined in one of embodiments 1) to 7) wherein $R^1$ is $(C_1$-$C_3)$alkoxy (and notably methoxy).
67) Yet another embodiment of this invention relates to the compounds of formula I as defined in one of embodiments 1) to 7) and 63) to 66) wherein $R^2$ is H.
68) Yet another embodiment of this invention relates to the compounds of formula I as defined in one of embodiments 1) to 7) and 63) to 67) wherein $R^3$ is H.
69) Yet another embodiment of this invention relates to the compounds of formula I as defined in one of embodiments 1) to 7) and 63) to 68) wherein $R^4$ is H.
70) Yet another embodiment of this invention relates to the compounds of formula I as defined in one of embodiments 1) to 7) and 63) to 68) wherein $R^4$ is halogen (and notably chlorine).
71) Yet another embodiment of this invention relates to the compounds of formula I as defined in one of embodiments 1) to 7) and 63) to 68) wherein $R^4$ is $(C_1$-$C_3)$alkyl (and notably methyl).
72) Yet another embodiment of this invention relates to the compounds of formula I as defined in one of embodiments 1) to 7) and 63) to 68) wherein $R^4$ is $(C_1$-$C_3)$alkoxy (and notably methoxy).
73) Yet another embodiment of this invention relates to the compounds of formula I as defined in one of embodiments 1) to 7) and 63) to 72) wherein $R^5$ is H or $(C_1$-$C_3)$alkyl (and notably wherein $R^5$ is methyl).
74) Yet another embodiment of this invention relates to the compounds of formula I as defined in one of embodiments 1) to 7) and 63) to 68) wherein $R^4$ and $R^5$ form together a —$CH_2CH_2CH_2$— group.
75) A particular embodiment of this invention relates to the compounds of formula I as defined in one of embodiments 1) to 7) wherein:
A is —$CH_2$— or #—$CH_2NH$—* (and notably —$CH_2$—);
one of $R^1$ and $R^4$ is independently halogen or $(C_1$-$C_3)$alkyl (and notably chlorine or methyl) and the other is H or each of $R^1$ and $R^4$ is independently halogen (and notably each of $R^1$ and $R^4$ is chlorine);
each of $R^2$ and $R^3$ is H; and
$R^5$ is methyl.
76) Another particular embodiment of this invention relates to the compounds of formula I as defined in one of embodiments 1) to 7) wherein:
A is —$CH_2CH_2$—;
one of $R^1$ and $R^4$ is independently halogen or $(C_1$-$C_3)$alkyl (and notably chlorine or methyl) and the other is H or each of $R^1$ and $R^4$ is independently halogen (and notably each of $R^1$ and $R^4$ is chlorine);
each of $R^2$ and $R^3$ is H; and
$R^5$ is methyl.

77) Yet another particular embodiment of this invention relates to the compounds of formula I as defined in one of embodiments 1) to 7) wherein:
A is —CH$_2$NHCH$_2$—;
one of R$^1$ and R$^4$ is independently halogen or (C$_1$-C$_3$)alkyl (and notably chlorine or methyl) and the other is H or each of R$^1$ and R$^4$ is independently halogen (and notably each of R$^1$ and R$^4$ is chlorine);
each of R$^2$ and R$^3$ is H; and
R$^5$ is methyl.

78) According to one embodiment of this invention, the compounds of formula I according to one of embodiments 1 to 77) will be such that they have the stereochemistry shown hereafter

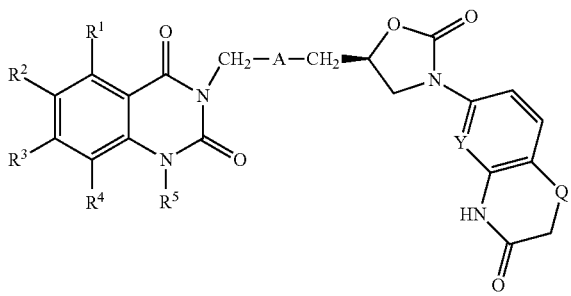

79) According to another embodiment of this invention, the compounds of formula I according to one of embodiments 1 to 77) will be such that they have the stereochemistry shown hereafter

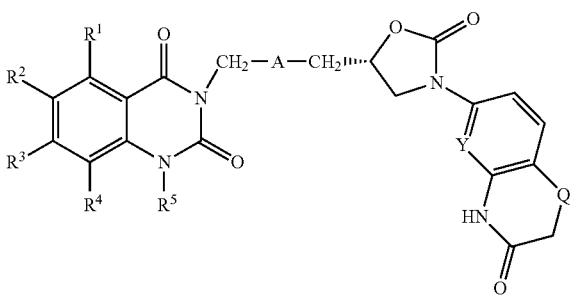

80) Another embodiment of this invention relates to compounds of formula I as defined in one of embodiments 1) to 79) as well as to isotopically labelled, especially $^2$H (deuterium) labelled compounds of formula I as defined in one of embodiments 1) to 79), which compounds are identical to the compounds of formula I as defined in one of embodiments 1) to 79) except that one or more atoms has or have each been replaced by an atom having the same atomic number but an atomic mass different from the atomic mass usually found in nature. Isotopically labelled, especially $^2$H (deuterium) labelled compounds of formula I and salts (in particular pharmaceutically acceptable salts) thereof are thus within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one variant of the invention, the compounds of formula I are not isotopically labelled, or they are labelled only with one or more deuterium atoms. Isotopically labelled compounds of formula I may be prepared in analogy to the methods described hereinafter, but using the appropriate isotopic variation of suitable reagents or starting materials.

81) Particularly preferred are the following compounds of formula I as defined in Embodiment 1

3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;
1-methyl-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione;
1-methyl-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;
3-{3-[(R)-2-oxo-3-(3-oxo-3,4-dihydro-2H-benzo[1,4]thiazin-6-yl)-oxazolidin-5-yl]-propyl}-1-propyl-1H-quinazoline-2,4-dione;
5-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;
1,5-dimethyl-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;
5-methyl-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;
5-methyl-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione;
5-methyl-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione;
6-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;
7-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;
8-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;
8-methyl-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;
8-methyl-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione;
8-methyl-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione;
5-chloro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;
5-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;
5-chloro-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;
5-chloro-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione;

5-chloro-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione;

8-chloro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

8-chloro-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione;

8-chloro-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione;

8-chloro-3-{3-[(S)-2-oxo-3-(3-oxo-3,4-dihydro-2H-pyrido[3,2-b][1,4]oxazin-6-yl)-oxazolidin-5-yl]-propyl}-1H-quinazoline-2,4-dione;

6-chloro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

6-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

7-chloro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

7-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

8-chloro-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;

8-chloro-1-methyl-3-(2-{2-[(R)-2-oxo-3-(3-oxo-3,4-dihydro-2H-benzo[1,4]thiazin-6-yl)-oxazolidin-5-yl]-ethylamino}-ethyl)-1H-quinazoline-2,4-dione;

8-chloro-1-methyl-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;

8-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

5-methoxy-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

6-methoxy-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

7-methoxy-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;

8-methoxy-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

3-{3-[(S)-2-oxo-3-(3-oxo-3,4-dihydro-2H-benzo[1,4]thiazin-6-yl)-oxazolidin-5-yl]-propyl}-6-pyrrolidin-1-yl-1H-quinazoline-2,4-dione;

6,7-difluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

6,7-dimethoxy-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

5,8-dichloro-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;

2-{3-[(R)-2-oxo-3-(3-oxo-3,4-dihydro-2H-benzo[1,4]thiazin-6-yl)-oxazolidin-5-yl]-propyl}-6,7-dihydro-5H-pyrido[3,2,1-ij]quinazoline-1,3-dione;

3-{3-[(S)-2-oxo-3-(3-oxo-3,4-dihydro-2H-benzo[1,4]thiazin-6-yl)-oxazolidin-5-yl]-propyl}-1H-benzo[g]quinazoline-2,4-dione;

1-cyclopropyl-6,7-difluoro-8-methoxy-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;

2-{3-[(S)-2-oxo-3-(3-oxo-3,4-dihydro-2H-benzo[1,4]thiazin-6-yl)-oxazolidin-5-yl]-propyl}-6,7-dihydro-5H-pyrido[3,2,1-ij]quinazoline-1,3-dione;

2-{3-[(S)-2-oxo-3-(3-oxo-3,4-dihydro-2H-pyrido[3,2-b][1,4]oxazin-6-yl)-oxazolidin-5-yl]-propyl}-6,7-dihydro-5H-pyrido[3,2,1-ij]quinazoline-1,3-dione;

7-bromo-1-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

1-methyl-3-{3-[(R)-2-oxo-3-(3-oxo-3,4-dihydro-2H-benzo[1,4]thiazin-6-yl)-oxazolidin-5-yl]-propyl}-7-vinyl-1H-quinazoline-2,4-dione;

3-{4-[2-oxo-3-(3-oxo-3,4-dihydro-2H-benzo[1,4]thiazin-6-yl)-oxazolidin-5-yl]-butyl}-1H-quinazoline-2,4-dione;

3-{2-hydroxy-4-[(S)-2-oxo-3-(3-oxo-3,4-dihydro-2H-benzo[1,4]oxazin-6-yl)-oxazolidin-5-yl]-butyl}-1-methyl-1H-quinazoline-2,4-dione;

3-{(R)-2-hydroxy-4-[(R)-2-oxo-3-(3-oxo-3,4-dihydro-2H-pyrido[3,2-b][1,4]thiazin-6-yl)-oxazolidin-5-yl]-butyl}-1-methyl-1H-quinazoline-2,4-dione;

1-methyl-3-{4-[(R)-2-oxo-3-(3-oxo-3,4-dihydro-2H-pyrido[3,2-b][1,4]thiazin-6-yl)-oxazolidin-5-yl]-butyl}-1H-quinazoline-2,4-dione;

1-methyl-3-{4-[(R)-2-oxo-3-(3-oxo-3,4-dihydro-2H-pyrido[3,2-b][1,4]oxazin-6-yl)-oxazolidin-5-yl]-butyl}-1H-quinazoline-2,4-dione;

3-(2-{[(R)-2-oxo-3-(3-oxo-3,4-dihydro-2H-pyrido[3,2-b][1,4]thiazin-6-yl)-oxazolidin-5-ylmethyl]-amino}-ethyl)-1H-quinazoline-2,4-dione;

3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione;

1-methyl-3-(2-{[(R)-2-oxo-3-(3-oxo-3,4-dihydro-2H-pyrido[3,2-b][1,4]thiazin-6-yl)-oxazolidin-5-ylmethyl]-amino}-ethyl)-1H-quinazoline-2,4-dione;

1-methyl-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione;

1,5-dimethyl-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione;

1,5-dimethyl-3-(2-{[(S)-2-oxo-3-(3-oxo-3,4-dihydro-2H-pyrido[3,2-b][1,4]thiazin-6-yl)-oxazolidin-5-ylmethyl]-amino}-ethyl)-1H-quinazoline-2,4-dione;

5-methyl-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione;

8-methyl-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione;

8-chloro-1-methyl-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione;

8-chloro-1-methyl-3-(2-{[(S)-2-oxo-3-(3-oxo-3,4-dihydro-2H-pyrido[3,2-b][1,4]thiazin-6-yl)-oxazolidin-5-ylmethyl]-amino}-ethyl)-1H-quinazoline-2,4-dione;

(E)-3-[1-methyl-2,4-dioxo-3-(2-{2-[2-oxo-3-(3-oxo-3,4-dihydro-2H-benzo[1,4]thiazin-6-yl)-oxazolidin-5-yl]-ethylamino}-ethyl)-1,2,3,4-tetrahydro-quinazolin-7-yl]-acrylic acid methyl ester;

8-chloro-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione;

(E)-3-[1-methyl-2,4-dioxo-3-(2-{[(S)-2-oxo-3-(3-oxo-3,4-dihydro-2H-benzo[1,4]thiazin-6-yl)-oxazolidin-5-ylmethyl]-amino}-ethyl)-1,2,3,4-tetrahydro-quinazolin-7-yl]-acrylic acid methyl ester;

2-(2-{[(R)-2-oxo-3-(3-oxo-3,4-dihydro-2H-benzo[1,4]thiazin-6-yl)-oxazolidin-5-ylmethyl]-amino}-ethyl)-6,7-dihydro-5H-pyrido[3,2,1-ij]quinazoline-1,3-dione;

2-(2-{[(S)-2-oxo-3-(3-oxo-3,4-dihydro-2H-pyrido[3,2-b][1,4]thiazin-6-yl)-oxazolidin-5-ylmethyl]-amino}-ethyl)-6,7-dihydro-5H-pyrido[3,2,1-ij]quinazoline-1,3-dione;

N-[2-(1-methyl-2,4-dioxo-1,4-dihydro-2H-quinazolin-3-yl)-ethyl]-N-[(R)-2-oxo-3-(3-oxo-3,4-dihydro-2H-pyrido[3,2-b][1,4]thiazin-6-yl)-oxazolidin-5-ylmethyl]-acetamide;

8-chloro-1-methyl-3-(2-{[(S)-2-oxo-3-(3-oxo-3,4-dihydro-2H-pyrido[3,2-b][1,4]oxazin-6-yl)-oxazolidin-5-ylmethyl]-amino}-ethyl)-1H-quinazoline-2,4-dione;

as well as the salts (in particular the pharmaceutically acceptable salts) thereof.

82) Particularly preferred are furthermore the 68 first compounds of formula I named in embodiment 81), as well as the salts (in particular the pharmaceutically acceptable salts) thereof.

83) The invention also relates to the groups of compounds of formula I selected from the group consisting of the compounds listed in embodiment 81) or 82), which groups of compounds furthermore correspond to one of embodiments 2) to 79), as well as to the salts (in particular the pharmaceutically acceptable salts) of such compounds. The invention moreover relates to any individual compound of formula I selected from the group consisting of the compounds listed in embodiment 81) or 82), and to the salts (in particular the pharmaceutically acceptable salts) of such individual compound.

The compounds of formula I according to the invention, i.e. according to one of embodiments 1) to 83) above, are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

The compounds of formula I according to the present invention are further useful for the preparation of a medicament for the treatment of infections that are mediated by bacteria such as *E. coli, Klebsiella pneumoniae* and other Enterobacteriaceae, *Acinetobacter* spp. including *Acinetobacter baumanii, Stenothrophomonas maltophilia, Neisseria meningitidis, Bacillus cereus, Bacillus anthracis, Clostridium difficile, Corynebacterium* spp., *Propionibacterium acnes* and bacteroide spp.

The compounds of formula I according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

The compounds of formula I according to this invention, or the pharmaceutically acceptable salt thereof, may be used for the preparation of a medicament, and are suitable, for the prevention or treatment of a bacterial infection.

One aspect of this invention therefore relates to the use of a compound of formula I according to one of embodiments 1) to 83), or of a pharmaceutically acceptable salt thereof, for the manufacture of a medicament for the prevention or treatment of a bacterial infection. Another aspect of this invention relates to a compound of formula I according to one of embodiments 1) to 83), or of a pharmaceutically acceptable salt thereof, for the prevention or treatment of a bacterial infection.

Accordingly, the compounds of formula I according to one of embodiments 1) to 83), or the pharmaceutically acceptable salts thereof, may be used for the preparation of a medicament, and are suitable, for the prevention or treatment of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, *Clostridium difficile* infections, urinary tract infections, sexually transmitted infections, foreign body infections, osteomyelitis, lyme disease, topical infections, opthalmological infections, tuberculosis and tropical diseases (e.g. malaria), and notably for the prevention or treatment of a bacterial infection selected from the group consisting of respiratory tract infections, otitis media, meningitis, skin and soft tissue infections (whether complicated or uncomplicated), pneumonia (including hospital acquired pneumonia) and bacteremia.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient comprising the administration to said patient of a pharmaceutically active amount of a compound of formula I according to one of embodiments 1) to 83) or a pharmaceutically acceptable salt thereof.

Moreover, the compounds of formula I according to this invention may also be used for cleaning purposes, e.g. to remove pathogenic microbes and bacteria from surgical instruments, catheters and artificial implants or to make a room or an area aseptic. For such purposes, the compounds of formula I could be contained in a solution or in a spray formulation.

The compounds of formula I can be manufactured in accordance with the present invention using the procedures described hereafter.

PREPARATION OF THE COMPOUNDS OF FORMULA I

Abbreviations

The following abbreviations are used throughout the specification and the examples:
Ac acetyl
AcOH acetic acid
AD-mix α 1,4-bis(dihydroquinine)phthalazine, $K_3Fe(CN)_6$, $K_2CO_3$ and $K_2OsO_4.2H_2O$
AD-mix β 1,4-bis(dihydroquinidine)phthalazine, $K_3Fe(CN)_6$, $K_2CO_3$ and $K_2OsO_4.2H_2O$
Alloc allyloxycarbonyl
aq. aqueous
BINAP 2,2'-bis(diphenylphosphino)-1,1'-binaphthyl
Boc tert-butoxycarbonyl
Bs 4-bromobenzenesulfonyl (brosylate)
Cbz benzyloxycarbonyl
CC column chromatography over silica gel
CDI 1,1'-carbonyldiimidazole
Cy cyclohexyl
DAD diode array detection
dba dibenzylideneacetone
DBU 1,8-diazabicyclo[5.4.0]undec-7-ene
DCC N,N'-dicyclohexylcarbodiimide
DCE 1,2-dichloroethane
DCM dichloromethane
DEAD diethyl azodicarboxylate
DIAD diisopropyl azodicarboxylate
DIPEA N,N-diisopropylethylamine
DMAP 4-dimethylaminopyridine
DME 1,2-dimethoxyethane
DMF N,N-dimethylformamide
DMSO dimethylsulfoxide
DPEPhos bis(2-diphenylphosphinophenyl)ether
DPPA diphenyl phosphoryl azide
EA ethyl acetate
EDC 1-ethyl-3-(3-dimethylaminopropyl) carbodiimide hydrochloride
ELSD evaporative light scattering detector
ESI electron spray ionisation
eq. equivalent
Et ethyl
ether diethyl ether
EtOH ethanol
Fmoc 9-fluorenylmethoxycarbonyl
HATU 2-(1H-7-azabenzotriazol-1-yl)-1,1,3,3-tetramethyl uronium hexafluorophosphate methanaminium
Hept heptane
Hex hexane
HOAT 1-hydroxy-7-aza-benzotriazole
HOBT 1-hydroxybenzotriazole
HPLC high pressure liquid chromatography
LC liquid chromatography
Me methyl
MeCN acetonitrile
MeOH methanol
MS mass spectroscopy
Ms methanesulfonyl (mesyl)
Nf nonafluorobutanesulfonyl
Ns 4-nitrobenzenesulfonyl (nosylate)
NMO N-methyl-morpholine N-oxide
org. organic
Pd/C palladium on carbon
$Pd(OH)_2$/C palladium dihydroxide on carbon
PEPPSI-IPr [1,3-bis(2,6-diisopropylphenyl)imidazol-2-ylidene](3-chloropyridyl)palladium(II) dichloride
PMB para-methoxybenzyl
$PPh_3$ triphenylphosphine
Pyr pyridine
Q-Phos 1,2,3,4,5-pentaphenyl-1'-(di-tert-butylphosphino) ferrocene
rac racemic
rt room temperature
salen 2,2'-ethylenebis(nitrilomethylidene)diphenol
sat. saturated
S-Phos 2-dicyclohexylphosphino-2',6'-dimethoxybiphenyl SK-CC01-A 2'-(dimethylamino)-2-biphenylyl-palladium(II) chloride dinorbornylphosphine complex
SK-CC02-A 2-(dimethylaminomethyl)ferrocen-1-yl-palladium(II) chloride dinorbornylphosphine complex
T3P propylphosphonic anhydride
TBAF tetra-n-butylammonium fluoride
TBDMS tert-butyldimethylsilyl
TBDPS tert-butyldiphenylsilyl
TBME tert-butyl methyl ether
tBu tert-butyl
TEA triethylamine
Tf trifluoromethanesulfonyl (triflyl)
TFA trifluoroacetic acid
THF tetrahydrofuran
TLC thin layer chromatography
TMS trimethylsilyl
$t_R$ retention time
Ts para-toluenesulfonyl
XantPhos 4,5-bis(diphenylphosphino)-9,9-dimethylxanthene
X-Phos 2-dicyclohexylphosphino-2',4',6'-triisopropylbiphenyl General Reaction Techniques General Reaction Technique 1 (Reaction with Triphosgene or CDI)

The aniline derivative is reacted with a carbonic acid derivative such as triphosgene or CDI. This reaction is preferably carried out in a dry aprotic solvent such as DCM or THF in presence of an org. base such as TEA or Pyr and at a temperature between 30° and +80° C., preferably between +25° and +80° C.

General Reaction Technique 2 (Amine Protection)

Amines are usually protected as carbamates such as Alloc, Cbz, Boc or Fmoc. The latter are obtained by reacting the amines with allyl or benzyl chloroformate, di-tert-butyl dicarbonate or FmocCl in presence of a base such as NaOH, TEA, DMAP or imidazole. They can also be protected as N-benzyl derivatives by reaction with benzyl bromide or chloride in the presence of a base such as $Na_2CO_3$ or TEA. Alternatively, N-benzyl derivatives can be obtained through reductive amination in presence of benzaldehyde and a borohydride reagent such as $NaBH_4$, $NaBH_3CN$ or $NaBH(OAc)_3$ in a solvent such as MeOH, DCE or THF. Further strategies to introduce other amine protecting groups have been described in T.W. Greene, P.G.M. Wuts, *Protecting Groups in Organic Synthesis*, 3rd Ed (1999), 494-653 (Publisher: John Wiley and Sons, Inc., New York, N.Y.).

General Reaction Technique 3 (Alcohol Protection)

The alcohols are protected as silyl ethers (usually TBDMS or TBDPS). The alcohol is reacted with the required silyl chloride reagent (TBDMSCl or TBDPSCl) in the presence of a base such as imidazole or TEA in a solvent such as DCM or DMF between 10° C. and 40° C. Further strategies to introduce other alcohol protecting groups have been described in Protecting Groups in Organic Synthesis 3$^{rd}$ Ed; 1999, 23-147; T.W. Greene, P.G.M. Wuts; (Publisher: John Wiley and Sons, Inc., New York, N.Y.).

General Reaction Technique 4 (Removal of Amino Protecting Groups)

The benzyl carbamates are deprotected by hydrogenolysis over a noble metal catalyst (e.g. Pd/C or Pd(OH)$_2$/C). The Boc group is removed under acidic conditions such as HCl in an org. solvent such as MeOH or dioxane, or TFA neat or diluted in a solvent such DCM. The Alloc group is removed in presence of tetrakis(triphenylphosphine)palladium(0) in presence of an allyl cation scavenger such as morpholine, dimedone or tributyltin hydride between 0° C. and 50° C. in a solvent such as THF.

The N-benzyl protected amines are deprotected by hydrogenolysis over a noble catalyst (e.g. Pd(OH)$_2$/C).

Further general methods to remove amine protecting groups have been described in *Protecting Groups in Organic Synthesis*, 3$^{rd}$ Ed (1999), 494-653; T.W. Greene, P.G.M. Wuts; (Publisher: John Wiley and Sons, Inc., New York, N.Y.).

General Reaction Technique 5 (Removal of Hydroxy Protecting Groups)

The silyl ether groups is removed either using fluoride anion sources such as TBAF in THF between 0° C. and +40° C. or HF in MeCN or water between 0° C. and +40° C. or using acidic conditions such as AcOH in THF/MeOH or HCl in MeOH. Further methods to remove the TBDMS and TBDPS groups are given in T.W. Greene, P.G.M. Wuts, *Protecting Groups in Organic Synthesis*, 3$^{rd}$ Ed (1999), 133-139 and 142-143 respectively (Publisher: John Wiley and Sons, Inc., New York, N.Y.). Further general methods to remove alcohol protecting groups are described in T.W. Greene, P.G.M. Wuts, Protecting Groups in Organic Synthesis, 3$^{rd}$ Ed (1999), 23-147 (Publisher: John Wiley and Sons, Inc., New York, N.Y.).

General Reaction Technique 6 (Alkylation of an Amine with a Mesylate or an Iodide)

The amine derivative is reacted with the required iodide derivatives or alcohol derivatives activated as a sulfonate (OMs, ONf, ONs, OBs, OTf, OTs) in the presence of an inorganic base such as $K_2CO_3$ or an org. base such as TEA or DIPEA in a solvent such as THF, DMF or DMSO between 0° C. and +80° C. Further details can be found in *Comprehensive Organic Transformations. A guide to Functional Group Preparations;* 2$^{11}$ Edition, R. C. Larock, Wiley-VC; New York, Chichester, Weinheim, Brisbane, Singapore, Toronto, (1999). Section Amines p.779.

General Reaction Technique 7 (Reductive Amination)

The reaction between the amine and the aldehyde or ketone is performed in a solvent system allowing the removal of the formed water through physical or chemical means (e.g. distillation of the solvent-water azeotrope or presence of drying agents such as molecular sieves, $MgSO_4$ or $Na_2SO_4$). Such solvent is typically toluene, Hex, THF, DCM or DCE or a mixture of solvents such as DCE/MeOH. The reaction can be catalyzed by traces of acid (usually AcOH). The intermediate imine is reduced with a suitable reducing agent (e.g. $NaBH_4$, $NaBH_3CN$, or $NaBH(OAc)_3$ or through hydrogenation over a noble metal catalyst such as Pd/C. The reaction is carried out between −10° C. and 110° C., preferably between 0° C. and 60° C. The reaction can also be carried out in one pot. It can also be performed in protic solvents such as MeOH or water in presence of a picoline-borane complex (*Tetrahedron* (2004), 60, 7899-7906).

General Reaction Technique 8 (Amide Formation)

The carboxylic acid (e.g acetic acid) is reacted with the required amine in the presence of an activating agent such as DCC, EDC, HOBT, HOAT, T3P, HATU or di-(N-succinimidyl)-carbonate, in a dry aprotic solvent such as DCM, MeCN or DMF between 20 and +60° C. (see G. Benz in *Comprehensive Organic Synthesis*, B. M. Trost, I. Fleming, Eds; Pergamon Press: New York (1991), vol. 6, p. 381). Alternatively, the carboxylic acid can first be activated by conversion into its corresponding acid chloride by reaction with oxalyl chloride or thionyl chloride neat or in a solvent such as DCM between −20° and +60° C. The carboxylic acid can also be activated as an anhydride. Further activating agents can be found in *Comprehensive Organic Transformations. A guide to Functional Group Preparations;* $2^{nd}$ Edition, R. C. Larock, Wiley-VC; New York, Chichester, Weinheim, Brisbane, Singapore, Toronto, 1999; Section nitriles, carboxylic acids and derivatives, p. 1941-1949.

General Reaction Technique 9 (Suzuki Coupling)

The aromatic halide (typically a bromide) is reacted with the required boronic acid derivative or its boronate ester equivalent (e.g. pinacol ester) in the presence of a palladium catalyst and a base such as $K_2CO_3$, $Cs_2CO_3$, $K_3PO_4$, tBuONa or tBuOK between 20 and 120° C. in a solvent such as toluene, THF, dioxane, DME or DMF, usually in the presence of water (20 to 50%). Examples of typical palladium catalysts are triarylphosphine palladium complexes such as $Pd(PPh_3)_4$. These catalysts can also be prepared in situ from a common palladium source such as $Pd(OAc)_2$ or $Pd_2(dba)_3$ and a ligand such as trialkylphosphines (e.g. $PCy_3$ or $P(tBu)_3$), dialkylphosphinobiphenyls (e.g. S-Phos) or ferrocenylphosphines (e.g. Q-phos). Alternatively, one can use a commercially available precatalyst based on palladacycle (e.g. SK-CC01-A) or N-heterocyclic carbene complexes (e.g. PEPPSI™-IPr). The reaction can also be performed by using the corresponding aromatic triflate. Further variations of the reaction are described in *Chem. Rev.* (1995), 95, 2457-2483, *Synthesis* (2004), 2419-2440, *Aldrichimica Acta* (2006), 39, 17-24 and 97-111, *Acc. Chem. Res.* (2008), 41, 1555-1564, and references cited therein.

General Reaction Technique 10 (Dihydroxylation)

The diol is obtained by dihydroxylation of the corresponding ethylenic derivative using a catalytic amount of osmium tetroxide in the presence a co-oxidant such as NMO in an aq. solvent such as an acetone-water or DCM-water mixture (see Cha, *Chem. Rev.* (1995), 95, 1761-1795).

General Reaction Technique 11 (Activation of an Alcohol)

The alcohol is reacted with MsCl, TfCl, NfCl, NsCl, BsCl or TsCl in the presence of an org. base such as TEA, DIPEA or Pyr in a dry aprotic solvent such as DCM, THF or Pyr between −10° C. and rt. Alternatively, the alcohol can also be reacted with $Ms_2O$ or $Tf_2O$. The activated intermediate can be further transformed into its corresponding iodo or bromo derivative by reaction of the activated alcohol with NaI or NaBr in a solvent such as acetone.

General Reaction Technique 12 (Formation of Azides)

The activated alcohol (activated as a sulfonate) or the corresponding halogenide derivative is reacted with sodium azide in presence of an org. base such as DIPEA or TEA or an inorganic base such as $Na_2CO_3$ in a solvent such as DMSO or DMF between 20 and 100° C. Alternatively, the azide can also be obtained by activation of the alcohol under Mitsunobu conditions in presence of $PPh_3$ and DEAD or DIAD in a solvent such as THF, DMF, DCM or DME between 20 and +60° C. as reviewed in *Synthesis* (1981), 1-28. Alternatively, the alcohol is directly reacted with DPPA in presence of a base such as TEA or DBU in a solvent such as THF between 20 and +60° C. as described in *J. Org. Chem.* (1993), 58, 5886-5888.

General Reaction Technique 13 (Formation of Phthalimides)

The activated alcohol (activated either as a sulfonate) or the corresponding halogenide derivative is reacted with potassium phthalimide in a solvent such as DMSO or DMF between 20 and 100° C.

General Reaction Technique 14 (Formation of Amines)

The azides are hydrogenated over a noble metal catalyst such as Pd/C in a solvent such as MeOH or EA. In case the molecule is containing an unsaturated double or triple bond, the reduction can be performed using $PPh_3$ in the presence of water as described in *J. Med. Chem.* (1993), 36, 2558-68. Besides, the phthalimide derivatives are treated between 50 and 120° C. with a hydrazine derivative such as hydrazine hydrate, methylhydrazine or an amine such as $N^1,N^1$-dimethylpropane-1,3-diamine in a solvent such as MeOH or EtOH. Further general methods have been described in *Protecting Groups in Organic Synthesis*, $3^{rd}$ Ed (1999), 564-566; T.W. Greene, P.G.M. Wuts (Publisher: John Wiley and Sons, Inc., New York).

General Reaction Technique 15 (Heck Reaction)

The unsaturated halide or triflate is reacted with an alkene and a strong base such as TEA, $K_2CO_3$, $Cs_2CO_3$ or NaOAc and an organopalladium catalyst such as tetrakis(triphenylphosphine)palladium(0), palladium chloride or palladium(II) acetate in a solvent such as DMF. The ligand is $PPh_3$, $P(o-tolyl)_3$ or BINAP. Further details can be obtained in R. F. Heck, *Org. React.* (1982), 27, 345-390 or A. de Meijere, F. E. Meyer, Jr., *Angew. Chem. Int. Ed. Engl.* (1994), 33(23-24), 2379-2411.

General Reaction Technique 16 (Goldberg-Type Coupling)

The aromatic halide is reacted with the required amide or lactam in presence of a copper catalyst such as CuI, a 1,2-diamine ligand such as N,N'-dimethylethylenediamine or trans-N,N'-dimethyl-1,2-cyclohexanediamine, a base such as $K_2CO_3$ or $K_3PO_4$ between 20° C. and 120° C. in a solvent such as toluene, THF, dioxane or DMF, as described in J. Am. Chem. Soc. (2002), 124, 7421-7428.

General Reaction Technique 17 (Buchwald-Hartwig Amination)

The aromatic halide is reacted with the required amine in presence of a palladium catalyst, a base such as $K_2CO_3$, $Cs_2CO_3$, $K_3PO_4$, tBuONa or tBuOK between 20° C. and 120° C. and in a solvent such as toluene, THF, dioxane, DME or DMF. Examples of typical palladium catalysts are triarylphosphine palladium complexes such as $Pd(PPh_3)_4$. These catalysts can also be prepared in situ from a common palladium source such as $Pd(OAc)_2$ or $Pd_2(dba)_3$ and a ligand such as trialkylphosphines (e.g. $PCy_3$ or $P(tBu)_3$), dialkylphosphinobiphenyls (e.g. X-Phos), chelating diphosphines (e.g. BINAP, XantPhos) or ferrocenylphosphines (e.g. Q-phos). Alternatively, one can use a commercially available precatalyst based on palladacycle (e.g. SK-CC02-A) or N-heterocyclic carbene complexes (e.g. PEPPSI™-IPr). The reaction can also be performed by using the corresponding aromatic triflate. Further variations of the reaction are described in *J. Org. Chem.* (2000), 65, 1144-1157, *Angew. Chem. Int. Ed.* (2005), 44, 1371-1375, *Aldrichimica Acta* (2006), 39, 17-24 and 97-111, *Angew. Chem. Int. Ed.* (2008), 47, 6338-6361, and references cited therein.

General Preparation Methods

PREPARATION OF THE COMPOUNDS OF FORMULA I

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) to g) hereafter describe general methods for preparing compounds of formula I. If not indicated otherwise, the generic groups $R^1$, $R^2$, $R^3$, $R^4$, $R^5$, $R^6$, A, Q and Y are as defined for formula I. General synthetic methods used repeatedly throughout the text below are referenced to and described in the above section entitled "General reaction techniques". Other abbreviations used are defined in the experimental section. In some instances the generic groups U, W, A and Y might be incompatible with the assembly illustrated in the procedures and schemes below and so will require the use of protecting groups. The use of protecting groups is well known in the art (see for example "*Protective Groups in Organic Synthesis*", T.W. Greene, P.G.M. Wuts, Wiley-Interscience, 1999).

The compounds of formula I can be obtained by:

a) ring closing the compounds of formula II

II wherein $R^1$, $R^2$, $R^3$, $R^4$, $R^5$, A, Q and Y have the same meaning as in formula I and $R^a$ represents an alkyl group such as methyl in the presence of NaH at rt; or b) reacting the compounds of formula III

III wherein $R^1$, $R^2$, $R^3$, $R^4$, $R^5$, Q and Y have the same meaning as in formula I and A' is —CH$_2$—, —CH$_2$CH$_2$—, #—CH$_2$N(PG$^1$)—*, —CH$_2$N(PG$^1$)CH$_2$— or #—CH(OPG$^2$)CH$_2$—* wherein PG$^1$ is Cbz or Boc and PG$^2$ is TMS, TBDMS or TBDPS with the carbonic acid derivatives of formula IV

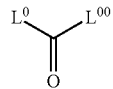

IV wherein $L^0$ and $L^{00}$ are both halogen, OCCl$_3$, imidazolyl or succinimidyloxy, or $L^0$ is halogen and $L^{00}$ is OCCl$_3$ using general reaction technique 1, whereby in case A' is #—CH$_2$N(PG$^1$)—* or —CH$_2$N(PG$^1$)CH$_2$—, the group PG$^1$ can be removed thereafter using general reaction technique 4 in case A' is #—CH(OPG$^2$)CH$_2$—*, the group PG$^2$ can be removed thereafter using general reaction technique 5; or c) reacting the compounds of formula V

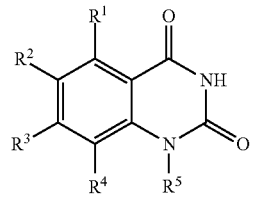

V wherein $R^1$, $R^2$, $R^3$ and $R^4$ have the same meaning as in formula I and $R^5$ does not represent H with compounds of formula VI

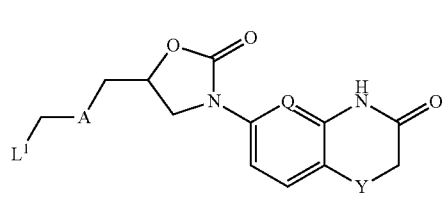

VI wherein A, Q and Y have the same meaning as in formula I and $L^1$ represents a sulfonate group such as OMs, OTs or OTf or a halogen such as iodine using general reaction technique 6 in presence of an inorganic base such as K$_2$CO$_3$ between +25° and +100° C.; or d) reacting the compounds of formula VII

VII wherein $R^1$, $R^2$, $R^3$, $R^4$ and $R^5$ have the same meaning as in formula I with compounds of formula VIII

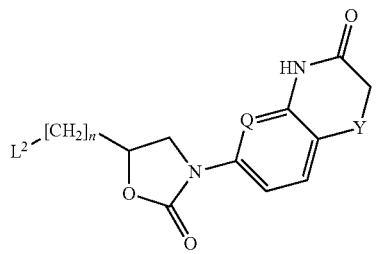

wherein Q and Y have the same meaning as in formula I, n represents 1 or 2 and $L^2$ represents a halogen such as iodine or a sulfonate group such as OMs, OTs or OTf using general reaction technique 6 in presence of an org. base such as DIPEA; or e) reacting the compounds of formula IX

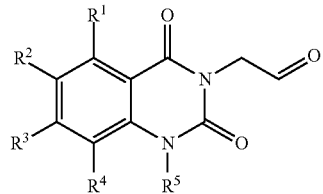

wherein $R^1$, $R^2$, $R^3$, $R^4$ and $R^5$ have the same meaning as in formula I with the compounds of formula X

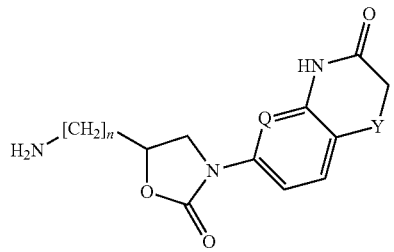

wherein Q and Y have the same meaning as in formula I and n represents 1 or 2 using general reaction technique 7; or f) reacting the compounds of formula XI

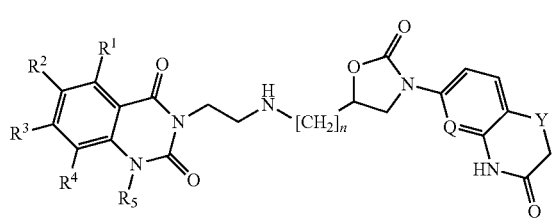

wherein $R^1$, $R^2$, $R^3$, $R^4$, $R^5$, Q and Y have the same meaning as in formula I and n represents 1 or 2 with acetic acid or an activated form thereof using general reaction technique 8; or g) reacting the compounds of formula XII

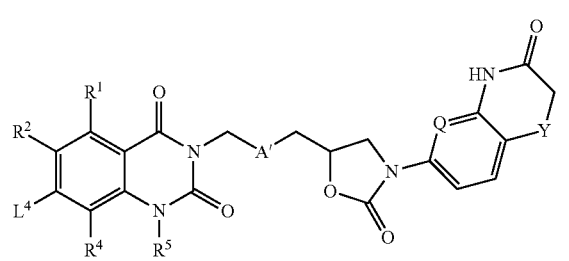

wherein $R^1$, $R^2$, $R^4$, $R^5$, Q and Y have the same meaning as in formula I, A' is —$CH_2$—, —$CH_2CH_2$—, #—CH($OPG^2$)$CH_2$—*, #—$CH_2N(PG^3)$—* or —$CH_2N(PG^3)$$CH_2$— wherein $PG^2$ is TMS, TBDMS or TBDPS, $PG^3$ is Alloc, Cbz or Boc and $L^4$ represents a halogen such as bromine with vinyl boronic anhydride pyridine complex using general reaction technique 9 or with an alkyl acrylate using general reaction technique 15, whereby in case A' is #—CH($OPG^2$)$CH_2$—*, the group $PG^2$ can be removed thereafter using general reaction technique 5 and in case A' is #—$CH_2N(PG^3)$—* or —$CH_2N(PG^3)$$CH_2$—, the group $PG^3$ can be removed thereafter using general reaction technique 4.

The compounds of formula I thus obtained may, if desired, be converted into their salts, and notably into their pharmaceutically acceptable salts.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine, diethylamine) and eluent B (hexane), at a flow rate of 0.8 to 150 ml/min. Whenever the compounds of formula I are obtained in the form of mixtures of diasteromers they may be separated by an appropriate combination of silica gel chromatography, HPLC and crystallization techniques.

PREPARATION OF THE SYNTHESIS INTERMEDIATES

Compounds of Formula II

The compounds of formula II can be prepared by reacting the compounds of formula III as defined previously with a compound of formula XIII $$ClCOOR^a \qquad \text{XIII}$$

wherein $R^a$ represents alkyl such as methyl or ethyl.

Compounds of Formula III

The compounds of formula III can be prepared as summarised in Scheme 1 hereafter.

Scheme 1

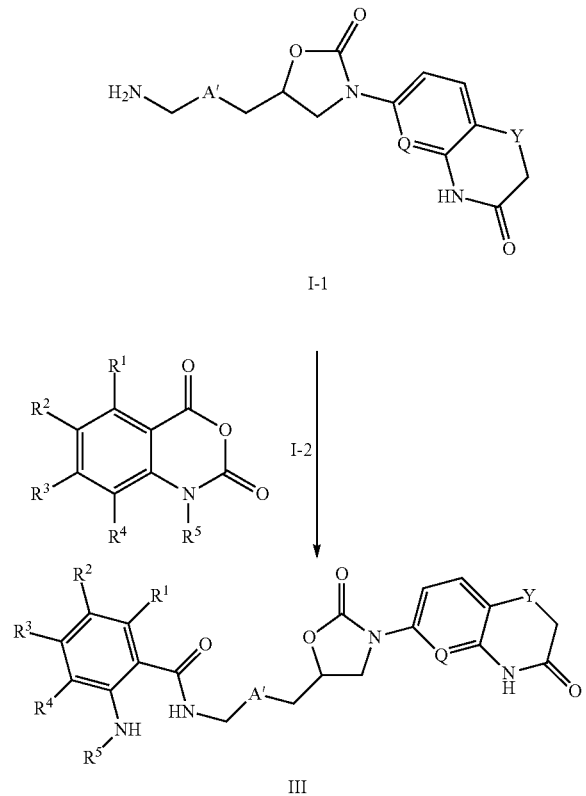

III

In Scheme 1, $R^1$, $R^2$, $R^3$, $R^4$, $R^5$, Q and Y have the same meaning as in formula I and A' is —CH$_2$—, —CH$_2$CH$_2$—, #—CH$_2$N(PG$^1$)—*, —CH$_2$N(PG$^1$)CH$_2$— or #—CH(OPG$^2$)CH$_2$—* wherein PG$^1$ is Cbz or Boc and PG$^2$ is TMS, TBDMS or TBDPS.

The amino derivatives of formula I-1 can be reacted (Scheme 1) with the isatoic anhydrides of formula I-2 in a solvent such as THF between +20° C. and +70° C.

Compounds of Formulae IV and XIII

These compounds are commercially available.

Compounds of Formulae V and VII

The compounds of formulae V and VII can be prepared as summarised in Scheme 2 hereafter.

Scheme 2

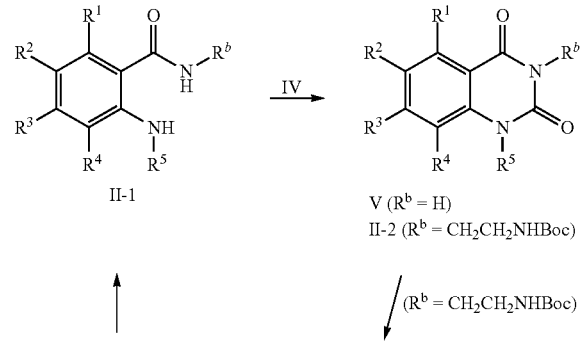

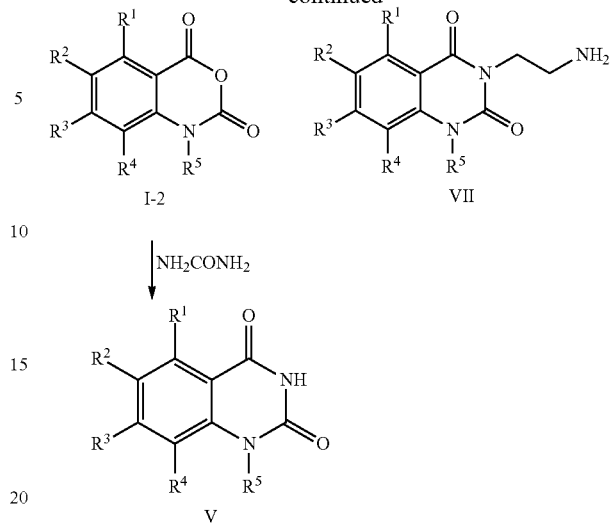

In Scheme 2, $R^1$, $R^2$, $R^3$, $R^4$ and $R^5$ have the same meaning as in formula I and $R^b$ represents H, 2-(tert-butoxycarbonylamino)ethyl or 2-aminoethyl.

The isatoic anhydride derivatives of formula I-2 can be reacted (Scheme 2) with the corresponding amine derivatives of formula $R^b NH_2$ wherein $R^b$ represents H or 2-(tert-butoxycarbonylamino)ethyl. The resulting amides of formula II-1 wherein $R^b$ represents H or 2-(tert-butoxycarbonylamino)ethyl can then be reacted with the carbonic acid derivative of formula IV as defined previously using general reaction technique 1. The compounds of formula II-2 wherein $R^b$ represents 2-(tert-butoxycarbonylamino)ethyl can further be reacted with TFA using general reaction technique 4. The compounds of formula V can also be obtained by reacting the compounds of formula I-2 with urea between 150 and 250° C.

Compounds of Formula IX

The compounds of formula IX can be prepared as summarised in Scheme 3 hereafter.

Scheme 3

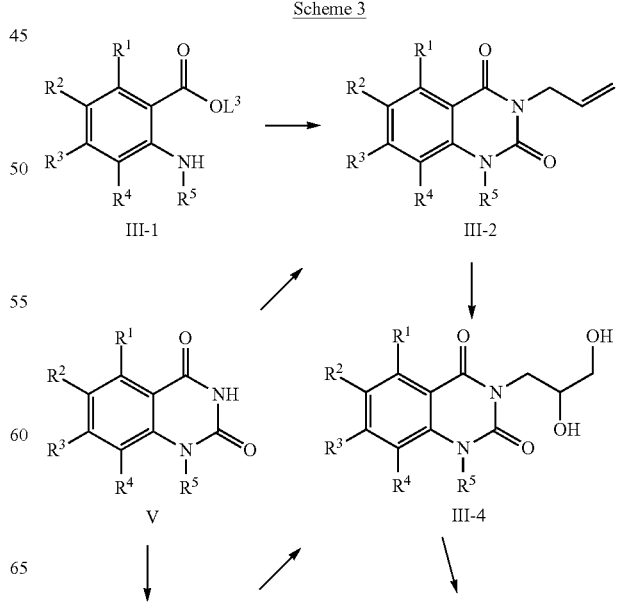

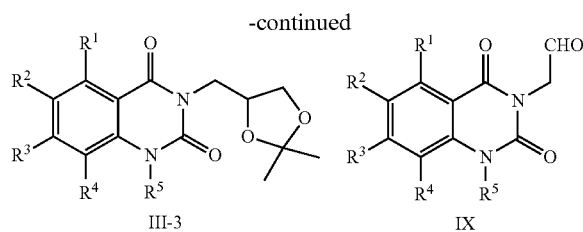

In Scheme 3, $R^1$, $R^2$, $R^3$ and $R^4$ have the same meaning as in formula I, $R^5$ is not H and $L^3$ represents alkyl such as methyl or ethyl.

The quinazolinedione derivatives of formula V can be reacted (Scheme 3) with allyl bromide in presence of a base such as $Cs_2CO_3$. Alternatively the compounds of formula III-2 can also be obtained by reacting the ester derivatives of formula III-1 with allyl isocyanate. The resulting derivatives of formula III-2 can be dihydroxylated using general reaction technique 10, affording the intermediates of formula III-4 which can further be converted into the aldehydes of formula IX by treatment with $NaIO_4$ in a water/MeOH mixture. Alternatively the compounds of formula III-4 can be prepared from the compounds of formula III-3, obtained by alkylation of the compounds of formula V with 4-(bromomethyl)-2,2-dimethyl-1,3-dioxolane, followed by removal of the acetonide protecting group under acidic conditions (e.g. using aq. HCl).

Compounds of Formulae I-I, VI, VIII and X

The compounds of formulae I-1, VI, VIII and X can be prepared as summarised in Scheme 4 hereafter.

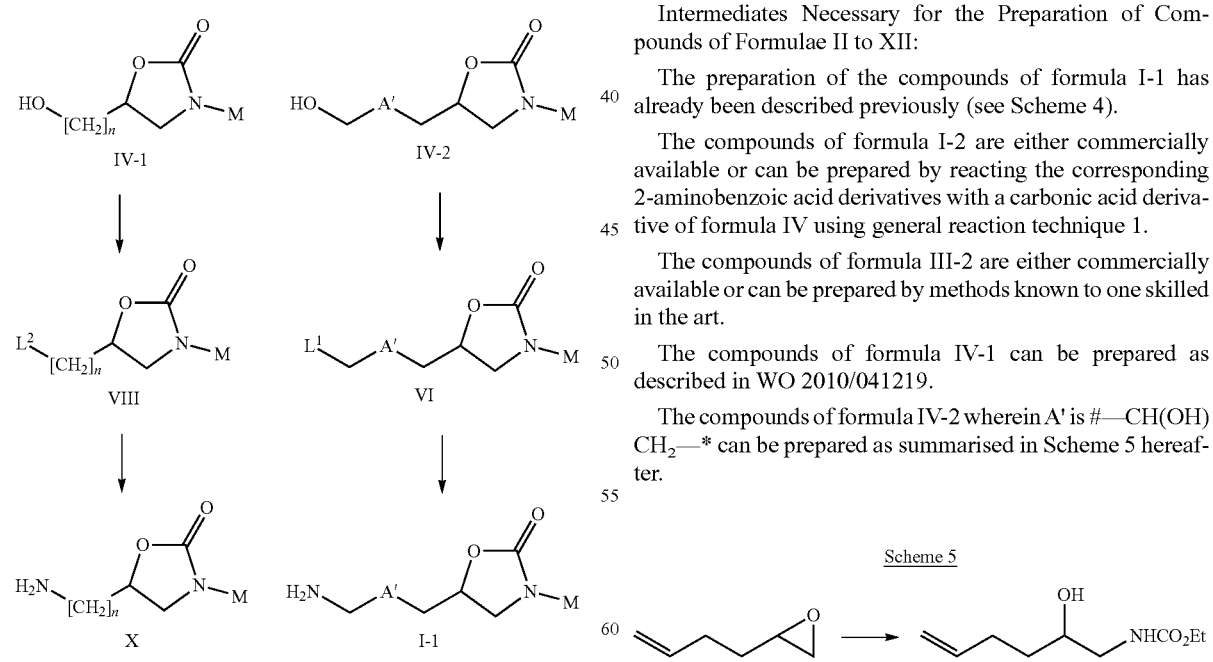

In Scheme 4, $L^1$, $L^2$ and n have the same meaning as in formulae VI, VIII and X, Q and Y have the same meanings as in formula I, A' is —$CH_2$—, —$CH_2CH_2$—, #—CH(OH)$CH_2$—*, #—$CH_2N(PG^1)$—* or —$CH_2N(PG^1)CH_2$— wherein $PG^1$ is Cbz or Boc and M represents the group The alcohols of formulae IV-1 and IV-2 can be sequentially transformed (Scheme 4) into their corresponding sulfonates of formulae VIII and VI using general reaction technique 11 and into the corresponding amines derivatives of formula X and I-1 using general reaction techniques 12 to 14. Alternatively the compounds of formulae VI and VIII wherein $L^1$ and $L^2$ represent a sulfonate such as OMs, OTs or OTf can be transformed into their corresponding iodide derivatives of formulae VI and VIII wherein $L^1$ and $L^2$ represent iodine before further transformation into the compounds of formulae I-1 and X respectively using general reaction techniques 12, 13 and 14.

Compounds of Formulae XI and XII

The compounds of formula XI correspond to compounds of formula I wherein A represents #—$CH_2NH$—* or —$CH_2NHCH_2$— and can be prepared according to one of the general preparation methods a) to c).

The compounds of formula XII correspond to compounds of formula I wherein $R^3$ is halogen and the possibly present free amino or alcohol function is protected. These compounds can be prepared according to one of the general preparation methods a) to c) preceded, if necessary, by a protection step according to general reaction technique 2 or 3.

Intermediates Necessary for the Preparation of Compounds of Formulae II to XII:

The preparation of the compounds of formula I-1 has already been described previously (see Scheme 4).

The compounds of formula I-2 are either commercially available or can be prepared by reacting the corresponding 2-aminobenzoic acid derivatives with a carbonic acid derivative of formula IV using general reaction technique 1.

The compounds of formula III-2 are either commercially available or can be prepared by methods known to one skilled in the art.

The compounds of formula IV-1 can be prepared as described in WO 2010/041219.

The compounds of formula IV-2 wherein A' is #—CH(OH)$CH_2$—* can be prepared as summarised in Scheme 5 hereafter.

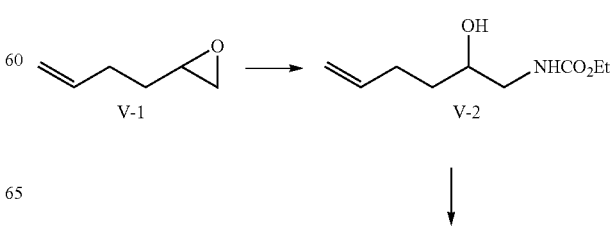

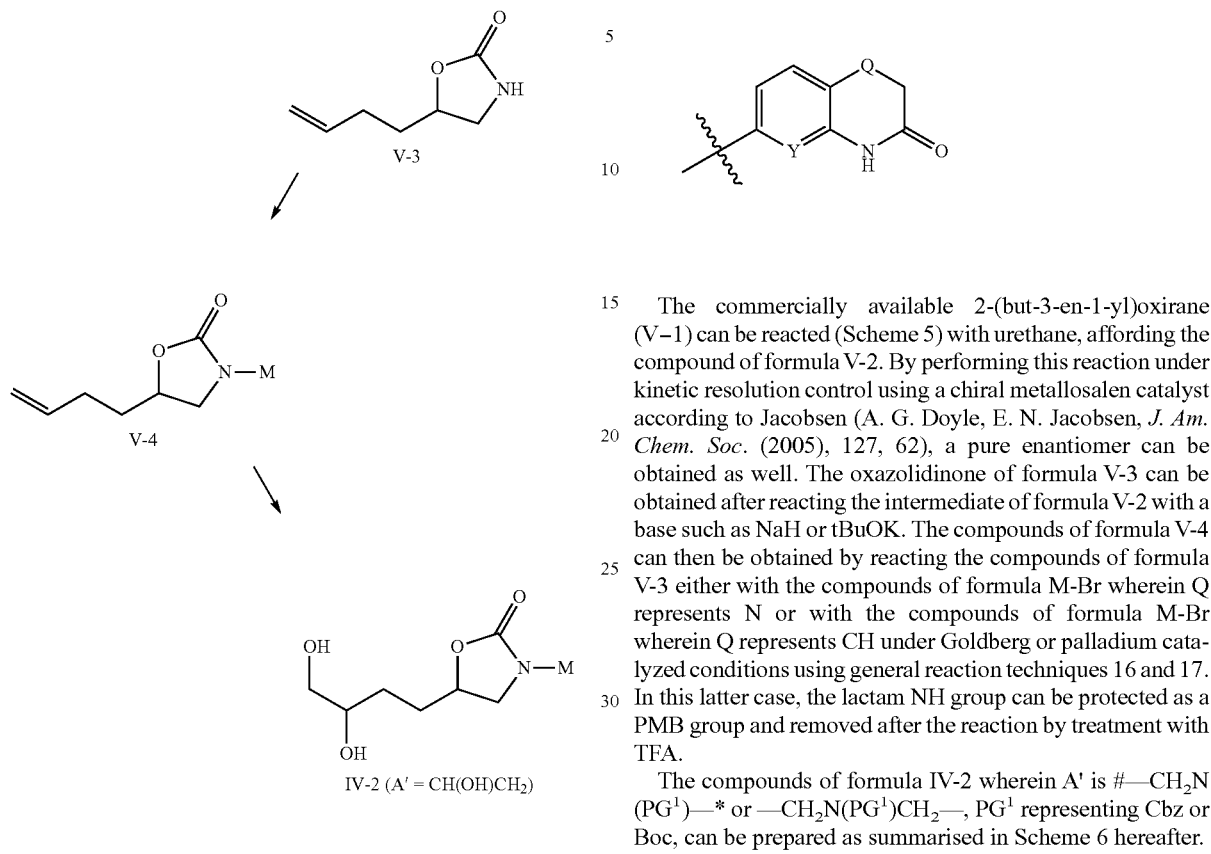

In Scheme 5, Q and Y have the same meaning as in formula I and M represents the group The commercially available 2-(but-3-en-1-yl)oxirane (V-1) can be reacted (Scheme 5) with urethane, affording the compound of formula V-2. By performing this reaction under kinetic resolution control using a chiral metallosalen catalyst according to Jacobsen (A. G. Doyle, E. N. Jacobsen, *J. Am. Chem. Soc.* (2005), 127, 62), a pure enantiomer can be obtained as well. The oxazolidinone of formula V-3 can be obtained after reacting the intermediate of formula V-2 with a base such as NaH or tBuOK. The compounds of formula V-4 can then be obtained by reacting the compounds of formula V-3 either with the compounds of formula M-Br wherein Q represents N or with the compounds of formula M-Br wherein Q represents CH under Goldberg or palladium catalyzed conditions using general reaction techniques 16 and 17. In this latter case, the lactam NH group can be protected as a PMB group and removed after the reaction by treatment with TFA.

The compounds of formula IV-2 wherein A' is #—CH$_2$N(PG$^1$)—* or —CH$_2$N(PG$^1$)CH$_2$—, PG$^1$ representing Cbz or Boc, can be prepared as summarised in Scheme 6 hereafter.

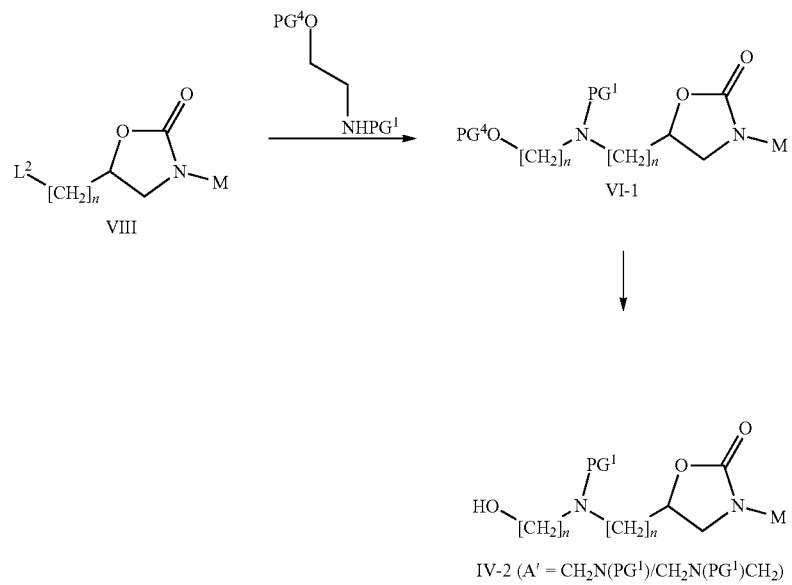

In Scheme 6, Q and Y have the same meaning as in formula I, n is 1 or 2, $L^2$ is as defined in formula VIII, $PG^1$ is Cbz or Boc, $PG^4$ represents an alcohol protecting group such as TBDMS and M represents the group

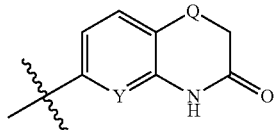

The sulfonate derivatives of formula VIII can be reacted (Scheme 6) with the protected amines of formula $PG^4O(CH_2)_2NHPG^1$, thus affording the derivatives of formula VI-1. The latter can be deprotected using general reaction technique 5, yielding the compounds of formula IV-2 wherein A' is #—$CH_2N(PG^1)$—* or —$CH_2N(PG^1)CH_2$—, $PG^1$ representing Cbz or Boc.

Particular embodiments of the invention are described in the following Examples, which serve to illustrate the invention in more detail without limiting its scope in any way.

EXAMPLES

Compounds are characterized by TLC (TLC plates from Merck, Silica gel 60 $F_{254}$) or by melting point; by $^1$H-NMR (300 MHz) (Varian Oxford); or by $^1$H-NMR (400 MHz) (Bruker Advance 400). Chemical shifts δ are given in ppm relative to the solvent used; multiplicities: s=singlet, d=doublet, t=triplet, q=quadruplet, p=pentuplet, hex=hexet, hep=heptet, m=multiplet, br.=broad; coupling constants J are given in Hz. Alternatively compounds are characterized by LC-MS (Sciex API 2000 with Agilent 1100 Binary Pump with DAD and ELSD or an Agilent quadrupole MS 6140 with Agilent 1200 Binary Pump, DAD and ELSD). High resolution LC-MS data (HR LC-MS) are obtained using a SYNAPT G2 MS device (Waters) equipped with a Waters Acquity Binary pump, an Acquity UPLC PDA Detector as DAD, an Acquity UPLC BEH C 18 1.7 μm 2.1×50 mm column from Waters (thermostated in the Acquity UPLC Column Manager at 60° C.) and the following eluents:
A: $H_2O$+0.05% $HCO_2H$ and
B: MeCN+0.05% $HCO_2H$,
with the following parameters:
gradient from (98% A+2% B) to (2% A+98% B) over 3.0 min,
flow rate of 0.6 ml/min and
detection at 214 nm wavelength.

The HPLCs of LC-MS are done over a stationary phase such as a rapid resolution Zorbax SB C18 (1.8 μm) column, or a rapid resolution Zorbax Eclipse Plus C18 (1.8 μm) column. Typical HPLC conditions are a gradient of eluent A (water: MeCN 95:5 with 0.1% of formic acid, in presence or not of 5 mmol/l ammonium formate) and eluent B (MeCN:water 95:5 with 0.1% of formic acid, in the presence or absence of 5 mmol/l ammonium formate), at a flow rate of 0.8 to 5 ml/min. Racemates can be separated into their enantiomers as described before. Preferred conditions of chiral HPLC are: ChiralPak AD (4.6×250 mm, 5 μm) column, using an isocratic mixture (e.g. at a ratio of 10/90) of eluent A (EtOH, in presence of diethylamine in an amount of e.g. 0.1%) and eluent B (Hex), at rt at a flow rate of e.g. 0.8 ml/min.

Compounds are purified by CC, i.e. chromatography on Silicagel 32-63 60 Å (Brunschwig). $NH_4OH$ as used for CC is 25% aq.

General Procedures

Procedure A: Opening of an Isatoic Anhydride with an Amine

A suspension of the amine (1 mmol) and isatoic anhydride derivative (1 mmol) in THF (7 ml) is stirred at 70° C. for 3 h. The reaction mixture is allowed to reach rt and can be either directly purified by CC (Hept/EA 1:2 to 0:1 followed by EA/MeOH 19:1) or worked up before CC by partitioning it between water and EA/MeOH 9:1. The aq. layer is extracted with EA/MeOH 9:1 and the combined org. layers are washed with water, brine, dried over $MgSO_4$ and concentrated under reduced pressure.

Procedure B: Quinazolinedione Formation (Triphosgene)

A suspension of the amide (1 mmol) in dioxane (5 ml) is treated with triphosgene (0.5M in dioxane; 0.6 mmol). The reaction is stirred at 70° C. for 1.5 h. The reaction mixture is cooled to rt and treated with sat. aq. $NaHCO_3$ (2 ml) and further stirred at rt for 30 min. The resulting crystals are filtered and washed with water. The solid is collected, stirred in MeOH/ether and filtered.

Procedure C: Quinazolinedione Formation (Carbamate Closure)

A solution of the carbamate (1 mmol) in DMF (20 ml) is treated with NaH (1 mmol) and the reaction mixture is stirred at rt for 3 h. The reaction mixture is partitioned between water and EA/MeOH 9:1. The aq. layer is extracted with EA/MeOH 9:1 and the combined org. layers are washed with water, brine, dried over $MgSO_4$ and concentrated under reduced pressure. The residue is then purified by CC (Hept/EA 1:2 to 0:1 followed by EA/MeOH 19:1).

Procedure D: Anthranilic Amide Formation

The acid derivative (1 mmol) is dissolved in DMF (1 ml) and treated with CDI (1M in DMF; 1.1 mmol) for 30 min at 50° C. The solution is treated with the corresponding amine (1 mmol) and the reaction mixture is further stirred at 50° C. for 1.5 h. The reaction mixture is treated with 0.1M HCl (20 ml) and extracted with EA. The org. layer is washed with water, dried over $MgSO_4$ and concentrated under reduced pressure.

Procedure E: Alkylation of Quinazolinediones with Mesylates or Halogenides

A solution of the quinazolinedione (1.0 mmol), mesylate (1 mmol) or halogenide (1 mmol) and $Cs_2CO_3$ (1.2 mmol) in dry DMF (5 ml) is stirred at rt for 12 h. The reaction mixture is diluted with water and EA and the phases are separated. The aq. layer is extracted two more times with EA and the combined org. layers are washed with water (3×) and brine, dried over $MgSO_4$ and concentrated under reduced pressure. The residue is dissolved in EA and crystallized from TBME or purified by CC.

Procedure F: Alkylation of Amines with Iodides or Mesylate

A solution of amine (1 mmol), iodide or mesylate (1 mmol) and DIPEA (1.1 mmol) in dry DMSO is heated to 70° C. until completion of the reaction (1-3 days). After cooling, water and EA are added and the phases are separated. The aq. layer is extracted two more times with EA and the combined org. layers are washed with water (3×) and brine, dried over MgSO$_4$ and concentrated under reduced pressure. The residue is then purified by CC.

Procedure G: Reductive Amination

A solution of the amine (1 mmol) and the aldehyde (1 mmol) in DCE/MeOH (1-1 to 4-1, 10 ml) is treated with NaBH(OAc)$_3$ (2 mmol). The mixture is stirred at rt until completion of the reaction (1-4 h), diluted with DCM and treated with aq. NH$_4$OH. The phases are separated. The aq. layer is extracted two more times with DCM and the combined org. layers are washed with water and brine, dried over MgSO$_4$ and concentrated under reduced pressure. The residue is then purified by CC.

Procedure H: Mesylate Formation

TEA or DIPEA (2 eq.) and MsCl (1.2 eq.) are added at 0° C. to a solution of the alcohol (1 eq.) in DCM or DCE. The reaction is stirred 1 h at this temperature. Sat. aq. NaHCO$_3$ is then added and the mixture is extracted with DCM (3×). The combined org. layers are dried over MgSO$_4$, filtered and concentrated under reduced pressure to afford the desired mesylate which can be used as such in a further step.

Procedure I: Azide Formation

Sodium azide (1.2 eq.) is added at rt to a solution of the required mesylate (1 eq.) in DMF (3 ml). The reaction is stirred 4 h at 80° C. The reaction mixture is cooled to rt, poured into water (25 ml) and extracted with EA/MeOH(9:1; 50 ml). The aq. layer is extracted with EA/MeOH (9:1; 2×). The combined org. layers are dried over MgSO$_4$, filtered and concentrated under reduced pressure to afford the desired azide which can be used as such in a further step or purified by CC.

Procedure J: Hydrogenation

A solution of the azide derivative (1 mmol) in MeOH (10 ml) and THF (10 ml) is hydrogenated over 10% Pd/C (100 mg) for 4 h. The catalyst is filtered off, washed with THF and the filtrate is concentrated under reduced pressure. The compound is used as such in the next step.

Procedure K: Removal of PMB Ethers

A solution of PMB ether (1 eq.) in TFA (5 ml) is heated at reflux for 5 days. The solution is cooled to rt, poured into water and neutralized with aq NH$_4$OH (28%). The solid is filtered and dried under reduced pressure. The resulting crude solid is stirred in EA, filtered (3×) and dried under reduced pressure. Under these conditions the TBDMS group, when present, is also removed.

Procedure L: Dihydroxylation

A mixture of olefin (1 mmol), NMO (1.1 mmol) and potassium osmate(VI) dihydrate (0.01 mmol) in DCM (4 ml) and water (1 ml) is vigorously stirred at rt overnight. The org. layer is separated and the aq. layer is extracted with DCM/MeOH (9:1). The aq. layer is evaporated to dryness. The residue is stirred in DCM/MeOH (9:1) and filtered. The filtrate is evaporated under reduced pressure and the residue is crystallized from MeOH/ether.

Procedure M: Asymmetric Dihydroxylation (See Chem. Rev. (1994), 94, 2483)

A mixture of olefin (1 mmol) in t-BuOH/H$_2$O (1:1, 10 ml) is treated at rt with methylsulfonamide (1 eq.) and AD-mix a or 13 (1.5 g). The mixture is vigorously stirred at rt until completion of reaction, Na$_2$S$_2$O$_3$ (1.5 g) is added and the mixture is diluted with EA (30 ml). The phases are separated and the aq. phase is extracted once more with EA. The combined org. layers are washed with water and brine, dried over MgSO$_4$ and concentrated. The residue is purified by CC.

Procedure N: Hydrolytic Kinetic Resolution of an Epoxide (S,S) or (R,R)-(salen)Co II (0.03 mmol), 4-nitrobenzoic acid (0.06 mmol) and TBME (2 ml) are stirred for 15 min at rt. The resulting solution is sequentially treated with urethane (0.5 mmol) and 1,2-epoxy-5-hexene (1 mmol). The reaction mixture is further stirred at rt for one day. The reaction mixture is diluted with sat. aq. NaHCO$_3$ solution and extracted with ether. The org. layer is washed with brine, dried over MgSO$_4$, filtered and evaporated under reduced pressure. The residue is purified by CC.

Procedure O: Oxazolidinone Formation

A solution of the urethane (1 mmol) in THF (4 ml) is cooled to 0° C. and treated with tBuOK (1.1 mmol). The reaction mixture is further stirred at rt for 1 h. The reaction mixture is diluted with water (5 ml) and extracted with EA (2×20 ml). The combined org. layers are washed with brine, dried over MgSO$_4$, filtered and evaporated under reduced pressure. The residue is purified by CC.

Procedure P: Cross Coupling Reaction

Dry dioxane (5 ml) is added to a mixture of 6-chloro-2H-pyrido[3,2-b]-1,4-thiazin-3(4H)-one (1 mmol; prepared according to WO 2010/041194, intermediate BK.ii), Pd(OAc)$_2$ (0.1 mmol), DPEphos (0.2 mmol), powdered potassium phosphate tribasic (2 mmol) and the oxazolidinone (1 mmol). The resulting suspension is stirred at rt and sparged with argon for 5 min. The reaction mixture is further stirred at 80° C. for 48 h, allowed to reach rt, filtered through a plug of Celite and the plug is washed with EA. The filtrate is diluted with water/brine and the aq. layer is extracted with EA (3×20 ml). The combined org. layers are washed with brine, dried over MgSO$_4$, filtered and evaporated under reduced pressure. The residue is purified by CC.

Procedure Q: Periodate Cleavage

A solution of the diol (1 mmol) in acetone (5 ml) is treated at rt with a solution of NaIO$_4$ (1.2 mmol) in water (2.5 ml). After stirring at rt for 1 h, the reaction mixture is filtered and the filtrate is diluted with EA, washed with water and brine, dried over MgSO$_4$, filtered and evaporated under reduced pressure.

Procedure R: Quinazolinedione Formation from Isatoic Anhydride Derivatives and Urea A mixture of urea (1.5 mmol) and the 2H-3,1-benzoxazine-2,4(1H)-dione derivative (1 mmol; "isatoic anhydride derivative") is heated at 200° C. for 30 min, then at 240° C. for 5 min. The reaction mixture is allowed to reach rt and is diluted with 0.1N NaOH and EA. The aq. layer is separated and acidified with 37% HCl (to pH 1) and extracted with EA. The resulting org. layer which occasionally contains some solid material is filtered before drying over MgSO$_4$. The org. layer is filtered and evaporated under reduced pressure. The total yield consisted of the filtered solid and the residue from the evaporation.

Procedure S: Reaction of N-Alkyl Isatoic Anhydrides with Boc-Ethylenediamine A solution of the N-alkylisatoic anhydride derivative (1 mmol) and N-Boc-ethylenediamine (1.1 mmol) in THF (6 ml) is stirred at 70° C. for 5 h. The mixture is allowed to cool to rt, concentrated under reduced and partitioned between EA/MeOH 9:1 and water. The aq. layer is washed 3 times with EA/MeOH 9:1 and the combined org. layers are washed with water (2×) and brine, dried over MgSO$_4$ and concentrated under reduced pressure. The crude product is purified by CC.

Procedure T: Quinazolinedione Formation with CDI

A solution of anthranilamide derivative (1 mmol) in THF (5 ml) is treated with CDI (2 mmol) and DBU (2 mmol) and stirred at 50° C. for 5 h. The reaction mixture is allowed to reach rt, diluted with water and extracted with EA/MeOH 9:1. The aq layer is extracted with EA/MeOH 9:1 and the combined org. layers are washed with brine, dried over MgSO$_4$ and concentrated under reduced pressure.

Procedure U: Boc Cleavage

Procedure U1

A solution of the Boc carbamate (1 mmol) in DCM (5 ml) is treated with TFA (23 mmol) and stirred at rt for 4 h. The reaction mixture was concentrated under reduced pressure and the residue was partitioned between DCM/MeOH 9:1 and diluted aq. NH$_4$OH. The aq layer was extracted with DCM/MeOH 9:1 and the combined org. layers are washed with brine, dried over MgSO$_4$ and concentrated under reduced pressure The crude product was purified by CC (DCM/MeOH 19:1, 9:1).

Procedure U2

A solution of the Boc carbamate (1 mmol) in dioxane (15 ml) is treated with 4M HCl in dioxane (7 ml) and stirred at rt for 2-4 h. The reaction mixture was filtered and the solid was washed with DCM/MeOH 9:1, affording the corresponding hydrochloride salt. The free base can be obtained by treating the solid with a base such an excess of aq. NH$_4$OH followed by partitioning between DCM/MeOH 9:1 and water. The aq. layer was extracted with DCM/MeOH 9:1 and the combined org. layers are washed with brine, dried over MgSO$_4$ and concentrated under reduced pressure The crude product was purified by CC (DCM/MeOH 19:1).

Procedure V: Mitsunobu Reaction

To a solution of alcohol (1 mmol) and PPh$_3$ (1.1 mmol) in THF (2 ml/mmol) cooled to 0° C., the quinazolidione derivative (1 mmol) and DIAD (1.2 mmol) are added dropwise and the mixture warmed to rt over 1 h and stirred at this temperature until completion of reaction. The mixture is concentrated under reduced pressure and the residue purified by CC.

Procedure W: Boc Protection

Boc$_2$O (1.05 mmol) and TEA (1.5 mmol) are added at rt to a solution of the corresponding amine (1.0 mmol) in THF. The reaction mixture is stirred at rt for 1 h, concentrated to dryness and purified by CC.

Preparations

Preparation A: 6-[(S)-5-(3-amino-propyl)-2-oxo-oxazolidin-3-yl]-4H-benzo[1,4]thiazin-3-one The compound was prepared in analogy to the method used for 6-[(R)-5-(3-amino-propyl)-2-oxo-oxazolidin-3-yl]-4H-benzo[1,4]thiazin-3-one (described in WO 2010/041219), using however (S,S)-salen-Co(III)-OTs instead of (R,R)-salen-Co(III)-OTs in the hydrolytic kinetic resolution step. The analytical data of all the intermediates and of the title compound ($^1$H NMR and MS) were identical to those of the enantiomers reported in WO 2010/041219.

$^1$H NMR (DMSO-d$_6$) δ: 7.24-7.38 (m, 2H), 7.02-7.11 (m, 1H), 4.59-4.73 (m, 1H), 4.02-4.14 (m, 1H), 3.56-3.67 (m, 1H), 3.41 (s, 2H), 2.52-2.60 (m, 2H), 1.66-1.79 (m, 2H), 1.32-1.54 (m, 2H).

Preparation B: 6-[(S)-5-(3-amino-propyl)-2-oxo-oxazolidin-3-yl]-4H-pyrido[3,2-b][1,4]thiazin-3-one

B.i. 6-[(S)-5-(3-hydroxy-propyl)-2-oxo-oxazolidin-3-yl]-4H-pyrido[3,2-b][1,4]thiazin-3-one The title compound was prepared in analogy to the method used for its (R)-enantiomer described in WO 2010/041194, using however (S,S)-salen-Co(III)-OTs instead of (R,R)-salen-Co(III)-OTs in the hydrolytic kinetic resolution step. The analytical data of all the intermediates and of the title compound ($^1$H NMR and MS) were identical to those of the enantiomers reported in WO 2010/041194.

$^1$H NMR (DMSO-d$_6$) δ: 8.82 (br. s, 1H), 7.74 (d, J=8.5 Hz, 1H), 7.49 (d, J=8.5 Hz, 1H), 4.53-4.65 (m, 1H), 4.16 (dd, J=8.5, 10.5 Hz, 1H), 3.69 (dd, J=7.2, 10.6 Hz, 1H), 3.56 (td, J=0.9, 6.3 Hz, 2H), 2.80 (br. s, 2H), 1.72-1.83 (m, 2H), 1.50-1.71 (m, 2H).

B.ii. Methanesulfonic acid 3-[(S)-2-oxo-3-(3-oxo-3,4-dihydro-2H-pyrido[3,2-b][1,4]thiazin-6-yl)-oxazolidin-5-yl]-propyl ester Starting from intermediate B.i (6.1 g, 19.7 mmol) and MsCl (1.84 ml, 23.7 mmol) and using Procedure H, the title compound was obtained as a beige solid (7.70 g; 100% yield). MS (ESI, m/z): 388.4 [M+H$^+$].

B.iii. 6-[(S)-5-(3-azido-propyl)-2-oxo-oxazolidin-3-yl]-4H-pyrido[3,2-b][1,4]thiazin-3-one Starting from intermediate B.ii (7.59 g, 19.6 mmol) and NaN$_3$ (1.53 g, 23.5 mmol) and using Procedure I, the title compound was obtained as a beige solid (5.70 g; 87% yield).

$^1$H NMR (CDCl$_3$) δ: 7.89 (d, J=8.5 Hz, 1H), 7.82 (br. s, 1H), 7.62 (d, J=8.5 Hz, 1H), 4.59-4.77 (m, 1H), 4.20-4.31 (m, 1H), 3.71-3.83 (m, 1H), 3.47 (s, 2H), 3.31-3.46 (m, 2H), 1.81-1.97 (m, 3H), 1.68-1.81 (m, 1H).

B.iv. 6-[(S)-5-(3-amino-propyl)-2-oxo-oxazolidin-3-yl]-4H-pyrido[3,2-b][1,4]thiazin-3-one Starting from intermediate B.iii (5.70 g, 17.0 mmol) and using Procedure J, the title compound was obtained as a colourless solid (5.30 g; 100% yield).
MS (ESI, m/z): 309.3 [M+H$^+$].

Preparation C: 6-[(R)-5-(3-amino-propyl)-2-oxo-oxazolidin-3-yl]-4H-pyrido[3,2-b][1,4]oxazin-3-one C.i. 6-[(R)-5-(3-hydroxy-propyl)-2-oxo-oxazolidin-3-yl]-4H-pyrido[3,2-b][1,4]oxazin-3-one Starting from 6-[(5R)-5-(3-hydroxypropyl)-2-oxo-3-oxazolidinyl]-4-[(4-methoxyphenyl)methyl]-2H-pyrido[3,2-b]-1,4-oxazin-3(4H)-one (prepared according to WO 2010/041194) and using Procedure K, the title compound was obtained as a greenish solid (3.08 g; 95% yield).
MS (ESI, m/z): 294.5 [M+H$^+$].

C.ii. Methanesulfonic acid 3-[(R)-2-oxo-3-(3-oxo-3,4-dihydro-2H-pyrido[3,2-b][1,4]oxazin-6-yl)-oxazolidin-5-yl]-propyl ester Starting from intermediate C.i and using Procedure H, the title compound was obtained as a colourless solid (0.475 g; 94% yield).
MS (ESI, m/z): 372.0 [M+H$^+$].

C.iii. 6-[(R)-5-(3-azido-propyl)-2-oxo-oxazolidin-3-yl]-4H-pyrido[3,2-b][1,4]oxazin-3-one Starting from intermediate C.ii and using Procedure I, the title compound was obtained as a colourless solid (0.390 g; 98% yield).
$^1$H NMR (DMSO-d$_6$) δ: 11.16 (s, 1H), 7.57 (d, J=8.5 Hz, 1H), 7.41 (d, J=8.7 Hz, 1H), 4.61-4.75 (m, 1H), 4.59 (s, 2H), 4.14-4.25 (m, 1H), 3.70 (dd, J=7.1, 10.1 Hz, 1H), 3.39 (t, J=6.8 Hz, 2H), 1.49-1.86 (m, 4H).

C.iv. 6-[(R)-5-(3-amino-propyl)-2-oxo-oxazolidin-3-yl]-4H-pyrido[3,2-b][1,4]oxazin-3-one Starting from intermediate C.iii and using Procedure J, the title compound was obtained as an off-white solid (0.231 g; 67% yield).
MS (ESI, m/z): 293.0 [M+H$^+$].

Preparation D: 6-[(S)-5-(3-amino-propyl)-2-oxo-oxazolidin-3-yl]-4H-pyrido[3,2-b][1,4]oxazin-3-one D.i. Methanesulfonic acid 3-[(S)-2-oxo-3-(3-oxo-3,4-dihydro-2H-pyrido[3,2-b][1,4]oxazin-6-yl)-oxazolidin-5-yl]-propyl ester Starting from 6-[(S)-5-(3-hydroxy-propyl)-2-oxo-oxazolidin-3-yl]-4H-pyrido[3,2-b][1,4]oxazin-3-one (prepared in analogy to step C.i, using however (R,R)-(salen)Co II) and using Procedure H, the title compound was obtained as a colourless solid (4.5 g; 63% yield).
MS (ESI, m/z): 371.8 [M+H$^+$].

D.ii. 6-[(S)-5-(3-azido-propyl)-2-oxo-oxazolidin-3-yl]-4H-pyrido[3,2-b][1,4]oxazin-3-one Starting from intermediate D.i and using Procedure I, the title compound was obtained as a colourless solid (0.210 g; 83% yield).
MS (ESI, m/z): 317.1 [M+H$^+$].

D.iii. 6-[(S)-5-(3-amino-propyl)-2-oxo-oxazolidin-3-yl]-4H-pyrido[3,2-b][1,4]oxazin-3-one Starting from intermediate D.ii and using Procedure J, the title compound was obtained as a colourless solid (0.170 g; 92% yield).
MS (ESI, m/z): 293.0 [M+H$^+$].

Preparation E: 7-bromo-1-methyl-1H-quinazoline-2,4-dione

Starting from 7-bromo-1-methyl-1H-benzo[d][1,3]oxazine-2,4-dione (6.44 mmol; prepared according to WO 2007/070359) and using Procedure R, the title compound was obtained as a colourless solid (800 mg, 49% yield).
MS (ESI, m/z): 169.1/171.2 [M+H$^+$].

Preparation F: rac-6-[5-(4-amino-butyl)-2-oxo-oxazolidin-3-yl]-4H-benzo[1,4]thiazin-3-one F.i. rac-Methanesulfonic acid 4-[2-oxo-3-(3-oxo-3,4-dihydro-2H-benzo[1,4]thiazin-6-yl)-oxazolidin-5-yl]-butyl ester Starting from rac-6-[5-(4-hydroxy-butyl)-2-oxo-oxazolidin-3-yl]-4H-benzo[1,4]thiazin-3-one (2.2 g; prepared according to WO 2010/041194, example BPiii) and using procedure H, the title intermediate was obtained as a beige solid (2.96 g; 100% yield).
$^1$H NMR (DMSO-d$_6$) δ: 10.54 (br. s, 1H), 7.25-7.36 (m, 2H), 7.07 (dd, J=2.3, 8.6 Hz, 1H), 4.58-4.75 (m, 1H), 4.20 (t, J=6.3 Hz, 2H), 4.08 (t, J=8.6 Hz, 1H), 3.63 (dd, J=7.2, 8.7 Hz, 1H), 3.41 (s, 2H), 3.15 (s, 3H), 1.64-1.81 (m, 2H), 1.37-1.57 (m, 2H), 1.15 (td, J=1.2, 7.1 Hz, 2H).

F.ii. rac-6-[5-(4-azido-butyl)-2-oxo-oxazolidin-3-yl]-4H-benzo[1,4]thiazin-3-one Starting from intermediate F.i and using Procedure I, the title intermediate was obtained as a beige solid (1.90 g; 80% yield).
$^1$H NMR (DMSO-d$_6$) δ: 10.53 (s, 1H), 7.25-7.36 (m, 2H), 7.07 (dd, J=2.4, 8.6 Hz, 1H), 4.59-4.72 (m, 1H), 4.08 (t, J=8.7 Hz, 1H), 3.62 (dd, J=7.1, 8.8 Hz, 1H), 3.41 (s, 2H), 3.34 (t, J=6.7 Hz, 2H), 1.67-1.80 (m, 2H), 1.51-1.64 (m, 2H), 1.35-1.50 (s, 2H).

F.iii. rac-6-[5-(4-amino-butyl)-2-oxo-oxazolidin-3-yl]-4H-benzo[1,4]thiazin-3-one Starting from intermediate F.ii and using Procedure J, the title intermediate was obtained as a beige solid (1.65 g; 94% yield).
$^1$H NMR (DMSO-d$_6$) δ: 7.24-7.39 (m, 2H), 7.01-7.12 (m, 1H), 4.56-4.71 (m, 1H), 4.00-4.14 (m, 1H), 3.56-3.70 (m, 1H), 3.41 (s, 2H), 3.30-3.41 (m, 2H), 1.58-1.81 (m, 2H), 1.27-1.47 (m, 4H).

Preparation G: (RS)-2-hydroxy-4-ORS)-2-oxo-3-(3-oxo-3,4-dihydro-2H-benzo[b][1,4]oxazin-6-yl)oxazolidin-5-yl)butyl methanesulfonate G.i. (RS)-6-(5-(but-3-en-1-yl)-2-oxooxazolidin-3-yl)-2H-benzo[b][1,4]oxazin-3 (4H)-one A suspension of methyltriphenylphosphonium bromide (2.03 g) in THF (6 ml) was treated with tBuOK (638 mg) and the reaction mixture was further stirred at rt for 1 h. The mixture was cooled to 0° C. and treated with a suspension of 3-[(S)-2-oxo-3-(3-oxo-3,4-dihydro-2H-benzo[1,4]oxazin-6-yl)-oxazolidin-5-yl]-propionaldehyde (1.50 g; prepared according to WO 2010/041194, example AV) in THF (11 ml). The reaction mixture was stirred at 0° C. for 30 min and allowed to reach rt. The reaction mixture was diluted with water and the org. layer was separated. The aq. layer was extracted with EA. The combined org. extracts were washed with brine, dried over MgSO$_4$, filtered and concentrated under reduced pressure. The residue was purified by CC (Hex/EA 4:1), affording a yellow solid (1.25 g; 84% yield).
$^1$H NMR (CDCl$_3$) δ: 8.02 (br., 1H), 7.42 (d, J=2.5 Hz, 1H), 6.95 (m, 1H), 6.79 (dd, J=8.8, 2.5 Hz, 1H), 5.95-5.85 (m, 1H), 5.15-5.05 (m, 2H), 4.8-4.6 (m, 1H), 4.59 (s, 2H), 4.04 (m, 1H), 3.62 (m, 1H), 2.27 (s, 2H), 2.0-1.75 (m, 2H).

G.ii. 6-((RS)-5-((RS)-3,4-dihydroxybutyl)-2-oxoox-azolidin-3-yl)-2H-benzo[b][1,4]oxazin-3 (4H)-one Starting from intermediate G.i and using Procedure L, the title intermediate was obtained as a beige solid (370 mg; 27% yield).
MS (ESI, m/z): 323.2 [M+H$^+$].

G.iii. (RS)-2-hydroxy-4-((RS)-2-oxo-3-(3-oxo-3,4-dihydro-2H-benzo[b][1,4]oxazin-6-yl)oxazolidin-5-yl)butyl methanesulfonate Starting from intermediate G.ii and using Procedure H, the title intermediate was obtained as a beige foam (440 mg; 100% yield, mixture of isomers).
$^1$H NMR (DMSO-d$_6$) δ: 10.71 (s, 1H), 7.32 (m, 1H), 6.92 (m, 2H), 4.92 (m, 1H), 4.68 (m, 1H), 4.52 (s, 2H), 4.39 (m, 2H), 4.09 (m, 1H), 3.95 (br., 1H), 3.65 (m, 1H), 3.24 (s, 3H), 1.83 (m, 4H).

Preparation H: methanesulfonic acid (RS)-2-hydroxy-4-[(R)-2-oxo-3-(3-oxo-3,4-dihydro-2H-pyrido[3,2-b][1,4]thiazin-6-yl)-oxazolidin-5-yl]-butyl ester H.i. ((R)-2-hydroxy-hex-5-enyl)-carbamic acid ethyl ester Starting from 1,2-epoxy-5-hexene (7.32 g) and using Procedure N (with (S,S)-(Salen)Co II), the title compound was obtained, after purification by CC (Hept/EA 3:1, 2:1 and 1:1), as a brown oil (31.17 g, 40% yield).
$^1$H NMR (CDCl$_3$) δ: 5.95-5.75 (m, 1H), 5.1-4.90 (m, 3H), 4.10-4.00 (m, 2H), 3.72 (m, 1H), 3.34 (m, 1H), 3.06 (m, 1H), 2.44 (br., 1H), 2.25-2.10 (m, 2H), 1.54 (m, 2H), 1.24 (m, 3H).

H.ii. (RS)-5-but-3-enyl-oxazolidin-2-one

Starting from intermediate H.i and using Procedure 0, the title compound was obtained as a beige semisolid (18.53 g; 92% yield).
$^1$H NMR (CDCl$_3$) δ: 6.16 (br. s, 1H), 5.69-5.88 (m, 1H), 4.96-5.11 (m, 1H), 5.00-5.04 (m, 1H), 4.56-4.69 (m, 1H), 3.66 (td, J=0.6, 8.5 Hz, 1H), 3.23 (td, J=0.8, 8.6 Hz, 1H), 2.07-2.31 (m, 2H), 1.81-1.98 (m, 1H), 1.64-1.79 (m, 1H).

H.iii. (RS)-5-(but-3-en-1-yl)-3-(3-oxo-3,4-dihydro-2H-pyrido[3,2-b][1,4]thiazin-6-yl)oxazolidin-2-one Starting from intermediate H.ii and using Procedure P, the title compound was obtained as a yellowish solid (810 mg, 53%) after purification by CC (Hept/EA 1:1, 0:1).

$^1$H NMR (CDCl$_3$) δ: 7.93 (d, J=8.5 Hz, 1H), 7.80 (br. s, 1H), 7.57-7.66 (m, 2H), 7.02 (d, J=8.0 Hz, 1H), 5.79-5.92 (m, 1H), 4.64-4.74 (m, 1H), 4.25 (dd, J=8.5, 10.4 Hz, 1H), 3.80 (dd, J=7.2, 10.5 Hz, 1H), 3.52 (s, 2H), 2.21-2.39 (m, 2H), 1.93-2.05 (m, 1H), 1.78-1.91 (m, 1H).

H.iv. 6-[(RS)-5-((R)-3,4-dihydroxy-butyl)-2-oxo-oxazolidin-3-yl]-4H-pyrido[3,2-b][1,4]thiazin-3-one Starting from intermediate H.iii and using Procedure M, the title intermediate was obtained as a beige solid (360 mg; 40% yield).
$^1$H NMR (DMSO-d$_6$) δ: 10.86 (s, 1H), 7.80 (m, 1H), 7.69 (m, 1H), 4.67-4.79 (m, 1H), 4.49-4.56 (m, 2H), 4.18-4.25 (m, 1H), 3.69-3.77 (m, 1H), 3.54 (s, 2H), 3.42-3.49 (m, 1H), 3.36-3.43 (m, 1H), 3.20-3.28 (m, 1H), 1.81-1.95 (m, 1H), 1.66-1.82 (m, 1H), 1.48-1.62 (m, 1H), 1.26-1.41 (m, 1H).

H.v. Methanesulfonic acid (RS)-2-hydroxy-4-[(R)-2-oxo-3-(3-oxo-3,4-dihydro-2H-pyrido[3,2-b][1,4]thiazin-6-yl)-oxazolidin-5-yl]-butyl ester Starting from intermediate H.iv and using Procedure H, the title intermediate was obtained as a colourless solid (280 mg; 65% yield).
$^1$H NMR (DMSO-d$_6$) δ: 10.85 (s, 1H), 7.78 (m, 1H), 7.66 (m, 1H), 4.87-4.98 (m, 1H), 4.64-4.81 (m, 1H), 4.31-4.50 (m, 2H), 4.15-4.26 (m, 1H), 3.65-3.78 (m, 1H), 3.51 (s, 2H), 3.44 (s, 3H), 1.69-1.95 (m, 4H).

Preparation I: (R)-4-(2-oxo-3-(3-oxo-3,4-dihydro-2H-pyrido[3,2-b][1,4]thiazin-6-yl)oxazolidin-5-yl) butyl methanesulfonate I.i. [(R)-6-(tert-butyl-dimethyl-silanyloxy)-2-hydroxy-hexyl]-carbamic acid ethyl ester Starting from rac-tert-butyl-dimethyl-(4-oxiranyl-butoxy)-silane (50.0 g, prepared according to WO 2008/126024) and using Procedure N (with (S,S)-(salen)Co II), the title compound was obtained, after purification by CC (Hept/EA 4:1, 1:1, 0:1), as a brown oil (24.32 g, 35% yield).
$^1$H NMR (CDCl$_3$) δ: 5.03 (br. s, 1H), 4.12 (q, J=7.1 Hz, 2H), 3.64-3.76 (m, 1H), 3.61 (t, J=5.8 Hz, 2H), 3.28-3.43 (m, 1H), 2.97-3.12 (m, 1H), 1.34-1.61 (m, 6H), 1.17-1.31 (m, 4H), 0.89 (s, 9H), 0.04 (s, 6H).

I.ii. (R)-5-[4-(tert-butyl-dimethyl-silanyloxy)-butyl]-oxazolidin-2-one

Starting from intermediate I.i and using Procedure 0, the title intermediate was obtained as a dark brown solid (17.75 g; 85% yield).
$^1$H NMR (CDCl$_3$) δ: 5.43 (br. s, 1H), 4.56-4.70 (m, 1H), 3.60-3.69 (m, 1H), 3.58-3.63 (m, 2H), 3.19-3.26 (m, 1H), 1.35-1.90 (m, 6H), 0.89 (s, 9H), 0.04 (s, 6H).

I.iii. (5R)-3-(3-oxo-3,4-dihydro-2H-pyrido[3,2-b][1,4]thiazin-6-yl)-5-(4-tert-butyl-dimethyl-silanyloxy-butyl)oxazolidin-2-one Starting from intermediate I.ii and 6-chloro-2H-pyrido[3,2-b]-1,4-thiazin-3(4H)-one (prepared according to WO 2010/041194, intermediate BKii) and using Procedure P, the title intermediate was obtained as a beige solid (6.55 g; 82% yield).

¹H NMR (CDCl₃) δ: 7.91 (d, J=8.6 Hz, 1H), 7.80 (br. s, 1H), 7.61 (d, J=8.5 Hz, 1H), 4.57-4.70 (m, 1H), 4.22 (dd, J=8.4, 10.4 Hz, 1H), 3.75 (dd, J=7.2, 10.5 Hz, 1H), 3.58-3.69 (m, 3H), 3.47 (s, 2H), 1.35-1.97 (m, 6H), 0.89 (s, 9H), 0.05 (s, 6H).

I.iv. 6-[(R)-5-(4-hydroxy-butyl)-2-oxo-oxazolidin-3-yl]-4H-pyrido[3,2-b][1,4]thiazin-3-one A solution of intermediate I.iii (15 mmol) in THF (150 ml) was treated with TBAF (1M in THF, 22.4 ml) at rt for 2 h. The reaction mixture was evaporated under reduced pressure and the residue was partitioned between water and EA. The aq. layer was extracted with EA and the combined org. layers were washed with water (2×) and brine, dried over MgSO₄ and concentrated under reduced pressure. The residue was sequentially stirred in TBME/MeOH then in Hept/EA, affording a beige solid (1.94 g; 40% yield).
¹H NMR (CDCl₃) δ: 7.90 (d, J=8.5 Hz, 1H), 7.80 (br. s, 1H), 7.61 (d, J=8.5 Hz, 1H), 4.58-4.72 (m, 1H), 4.23 (dd, J=8.5, 10.5 Hz, 1H), 3.77 (dd, J=7.2, 10.5 Hz, 1H), 3.64-3.73 (m, 2H), 3.47 (s, 2H), 1.46-1.97 (m, 7H).

I.v. (R)-4-(2-oxo-3-(3-oxo-3,4-dihydro-2H-pyrido[3,2-b][1,4]thiazin-6-yl)oxazolidin-5-yl)butyl methanesulfonate Starting from intermediate I.iv and using Procedure H, the title intermediate was obtained as an off-white solid (0.67 g; 100% yield).
¹H NMR (CDCl₃) δ: 7.89 (d, J=8.6 Hz, 1H), 7.80 (br. s, 1H), 7.62 (d, J=8.6 Hz, 1H), 4.58-4.72 (m, 1H), 4.20-4.30 (m, 3H), 3.77 (dd, J=7.2, 10.5 Hz, 1H), 3.47 (s, 2H), 3.02 (s, 3H), 1.60-1.94 (m, 6H).

Preparation J: methanesulfonic acid 4-[(R)-2-oxo-3-(3-oxo-3,4-dihydro-2H-pyrido[3,2-b][1,4]oxazin-6-yl)-oxazolidin-5-yl]-butyl ester Starting from 6-[(R)-5-(4-hydroxy-butyl)-2-oxo-oxazolidin-3-yl]-4H-pyrido[3,2-b][1,4]oxazin-3-one (obtained in analogy to steps I.i to I.iv of preparation I, using however 6-bromo-4-[(4-methoxyphenyl)methyl]-2H-pyrido[3,2-b]-1,4-oxazin-3(4H)-one (prepared according to WO 2009/104159) instead of 6-chloro-2H-pyrido[3,2-b]-1,4-thiazin-3 (4H)-one in the third step), and subjecting the intermediate obtained after the fourth step to Procedure H, the title compound was obtained as a colourless solid (0.50 g; 80% yield).
MS (ESI, m/z): 386.1 [M+H⁺].

Preparation K: 3-(2-amino-ethyl)-1-methyl-1H-quinazoline-2,4-dione

K.i. [2-(2-methylamino-benzoylamino)-ethyl]-carbamic acid tert-butyl ester

Starting from N-methylisatoic anhydride and N-Boc-ethylenediamine and using Procedure S, the title compound was obtained as a slightly brown solid (903 mg; quantitative).
MS (ESI, m/z): 294.5 [M+H⁺].

K.ii. [2-(2-methylamino-benzoylamino)-ethyl]-carbamic acid tert-butyl ester

Starting from intermediate K.i and using Procedure T, the title intermediate was obtained as a colourless solid (396 mg; 50% yield).
MS (ESI, m/z): 320.3 [M+H⁺].

K.iii. 3-(2-amino-ethyl)-1-methyl-1H-quinazoline-2,4-dione

Starting from intermediate K.ii and using Procedure U2, the title intermediate was obtained as a colourless solid (214 mg; 82% yield).
MS (ESI, m/z): 220.2 [M+H⁺].

Preparation L: (1-methyl-2,4-dioxo-1,4-dihydro-2H-quinazolin-3-yl)-acetaldehyde

L.i. 3-allyl-1-methyl-1H-quinazoline-2,4-dione

Starting from 1-methylquinazoline-2,4(1H,3H)-dione and allyl bromide and using Procedure E, the title intermediate was obtained as a colourless solid (0.125 g; 58% yield).
¹H NMR (CDCl₃) δ: 8.03 (dd, J=7.9, 1.6 Hz, 1H), 7.77 (m, 1H), 7.44 (d, J=8.4 Hz, 1H), 7.29 (m, 1H), 5.85 (m, 1H), 5.12 (m, 1H), 5.07 (t, J=1.5 Hz, 1H), 4.53 (dt, J=5.3, 1.5 Hz, 2H), 3.50 (s, 3H).

L.ii. rac-3-(2,3-dihydroxy-propyl)-1-methyl-M-quinazoline-2,4-dione

Starting from intermediate L.i and using Procedure L, the title intermediate was obtained as a yellowish foam (95 mg; 82% yield).
¹H NMR (CDCl₃) δ: 8.19 (dd, J=1.5, 7.9 Hz, 1H), 7.65-7.74 (m, 1H), 7.18-7.31 (m, 2H), 4.22-4.39 (m, 2H), 3.97-4.09 (m, 1H), 3.60 (s, 3H), 3.54-3.62 (m, 2H), 3.37-3.48 (m, 1H), 3.04-3.20 (m, 1H).

L.iii. (1-methyl-2,4-dioxo-1,4-dihydro-2H-quinazolin-3-yl)-acetaldehyde

Starting from intermediate L.ii and using Procedure Q, the title intermediate was obtained as a colourless solid (57 mg; 69% yield).
¹H NMR (CDCl₃) δ: 9.67 (s, 1H), 8.20-8.25 (m, 1H), 7.69-7.75 (m, 1H), 7.26-7.33 (m, 1H), 7.22-7.26 (m, 1H), 4.95 (s, 2H), 3.62 (s, 3H).

Preparation M: (1,5-dimethyl-2,4-dioxo-1,4-dihydro-2H-quinazolin-3-yl)-acetaldehyde M.i. 1,5-dimethyl-1H-quinazoline-2,4-dione Starting from 1,5-dimethyl-2H-3,1-benzoxazine-2,4(1H)-dione (prepared according to WO 98/42688) and urea and using Procedure R, the title compound was obtained as an off-white solid (681 mg, 57% yield).
MS (ESI, m/z): 381.28 [2M+H⁺].

M.ii. 3-allyl-1,5-dimethyl-1H-quinazoline-2,4-dione

Starting from intermediate M.i and allyl bromide and using Procedure E, the title intermediate was obtained as a colourless solid (0.461 g; 88% yield).
MS (ESI, m/z): 231.3 [M+H⁺].

M.iii. rac-3-(2,3-dihydroxy-propyl)-1-methyl-1H-quinazoline-2,4-dione

Starting from intermediate M.ii and using Procedure L, the title intermediate was obtained as a beige solid (47 mg; 91% yield).
MS (ESI, m/z): 265.3 [M+H⁺].

M.iv. (1,5-dimethyl-2,4-dioxo-1,4-dihydro-2H-quinazolin-3-yl)-acetaldehyde

Starting from intermediate M.iii and using Procedure Q, the title intermediate was obtained as a colourless solid (32 mg; 79% yield).
MS (ESI, m/z): 233.3 [M+H$^+$].

Preparation N: 6-((S)-5-aminomethyl-2-oxo-oxazolidin-3-yl)-4H-pyrido[3,2-b][1,4]thiazin-3-one

N.i. 6-((R)-5-azidomethyl-2-oxo-oxazolidin-3-yl)-4H-pyrido[3,2-b][1,4]thiazin-3-one Starting from methanesulfonic acid (R)-2-oxo-3-(3-oxo-3,4-dihydro-2H-pyrido[3,2-b][1,4]thiazin-6-yl)-oxazolidin-5-ylmethyl ester (prepared according to WO 2010/041194) and using Procedure I, the title compound was obtained as a beige solid (2.0 g; 90% yield).
$^1$H NMR (CDCl$_3$) δ: 7.90 (d, J=8.5 Hz, 1H), 7.80 (br. s, 1H), 7.64 (d, J=8.5 Hz, 1H), 4.72-4.83 (m, 1H), 4.16-4.25 (m, 1H), 3.99 (dd, J=6.2, 10.7 Hz, 1H), 3.54-3.75 (m, 2H), 3.48 (s, 2H).

N.ii. 6-((S)-5-aminomethyl-2-oxo-oxazolidin-3yl)-4H-pyrido[3,2-b][1,4]thiazin-3-one A solution of intermediate N.i (2.0 g) in THF (25 ml) was treated with PPh$_3$ (1.88 g) and water (1.18 ml) and further stirred at 60° C. for 3 h. The reaction mixture was partially concentrated under reduced pressure and the residue was taken up in DCM and water. The org. layer was extracted with 1N HCl. The resulting acidic layer was basified with diluted NH$_4$OH and extracted twice with DCM/MeOH. The combined org. layers were washed with brine, dried over MgSO$_4$ and concentrated under reduced pressure. The residue was stirred in ether to give a colourless solid (1.6 g; 87% yield).
$^1$H NMR (DMSO-d$_6$) δ: 7.77 (m, 1H), 7.68 (m, 1H), 4.54-4.67 (m, 1H), 4.03-4.16 (m, 1H), 3.87 (dd, J=6.5, 10.2 Hz, 1H), 3.51 (s, 2H), 2-71-2.88 (m, 2H).

Preparation O: 3-(2-amino-ethyl)-5-methyl-1H-quinazoline-2,4-dione

O.i. [2-(2-amino-6-methyl-benzoylamino)-ethyl]-carbamic acid tert-butyl ester Starting from 5-methylisatoic anhydride and N-Boc-ethylenediamine and using Procedure S, the title intermediate was obtained as a colourless solid (188 mg; 80% yield).
$^1$H NMR (DMSO-d$_6$) δ: 8.15-8.10 (m, 1H), 6.90 (m, 1H), 6.70-6.80 (m, 1H), 6.50 (m, 1H), 6.38 (m, 1H), 4.82 (s, 2H), 3.22 (m, 2H), 3.09 (m, 2H), 2.12 (s, 3H), 1.36 (s, 9H).

O.ii. [2-(5-methyl-2,4-dioxo-1,4-dihydro-2H-quinazolin-3-yl)-ethyl]-carbamic acid tert-butyl ester Starting from intermediate O.i and using Procedure T, the title intermediate was obtained as a colourless foam (125 mg; 65% yield).
MS (ESI, m/z): 318.0 [M+H$^+$].

O.iii. 3-(2-amino-ethyl)-5-methyl-1H-quinazoline-2,4-dione

Starting from intermediate O.ii and using procedure U2, the title intermediate was obtained as a colourless solid (59 mg; 79% yield).
MS (ESI, m/z): 220.3 [M+H$^+$].

Preparation P: 3-(2-amino-ethyl)-8-methyl-1H-quinazoline-2,4-dione

P.i. [2-(2-amino-3-methyl-benzoylamino)-ethyl]-carbamic acid tert-butyl ester Starting from 8-methylisatoic anhydride and N-Boc-ethylenediamine and using Procedure S, the title intermediate was obtained as a colourless solid (236 mg; 100% yield).
MS (ESI, m/z): 294.2 [M+H$^+$].

P.ii. [2-(8-methyl-2,4-dioxo-1,4-dihydro-2H-quinazolin-3-yl)-ethyl]-carbamic acid tert-butyl ester Starting from intermediate P.i and using Procedure T, the title intermediate was obtained as a colourless foam (274 mg; 100% yield).
MS (ESI, m/z): 318.0 [M+H$^+$].

P.iii. 3-(2-amino-ethyl)-8-methyl-1H-quinazoline-2,4-dione

Starting from intermediate P.ii and using Procedure U2, the title intermediate was obtained as a colourless solid (111 mg; 63% yield).
MS (ESI, m/z): 220.3 [M+H$^+$].

Preparation Q: (8-chloro-1-methyl-2,4-dioxo-1,4-dihydro-2H-quinazolin-3-yl)-acetaldehyde

Q.i. 8-chloro-1-methyl-1H-quinazoline-2,4-dione

Starting from 8-chloro-1-methyl-2H-3,1-benzoxazine-2,4(1H)-dione and using Procedure R, the title intermediate was obtained as a light yellow solid (1.58 g; 40% yield).
$^1$H NMR (DMSO-d$_6$) δ: 11.70 (s, 1H), 7.97 (dd, J=7.7, 1.7 Hz, 1H), 7.81 (dd, J=7.9, 1.7 Hz, 1H), 7.26 (t, J=7.8 Hz, 1H), 3.64 (s, 3H).

Q.ii. 8-chloro-3-((RS)-2,2-dimethyl-[1,3]dioxolan-4-ylmethyl)-1-methyl-1H-quinazoline-2,4-dione Starting from intermediate Q.i and 2,2,-dimethyl-1,3-dioxolane-4-methanol and using Procedure V, the title intermediate was obtained as a light yellow solid (1.40 g; 48% yield).
$^1$H NMR (DMSO-d$_6$) δ: 8.02 (dd, J=7.8, 1.7 Hz, 1H), 7.84 (dd, J=7.8, 1.6 Hz, 1H), 7.29 (t, J=7.8 Hz, 1H), 4.28 (m, 1H), 4.14 (m, 1H), 3.94 (m, 2H), 3.76 (dd, J=8.7, 5.1 Hz, 1H), 3.66 (m, 3H), 1.31 (s, 3H), 1.20 (s, 3H).

Q.iii. (8-chloro-1-methyl-2,4-dioxo-1,4-dihydro-2H-quinazolin-3-yl)-acetaldehyde A solution of intermediate Q.ii (1.39 g) in dioxane (12 ml) was stirred in 3N HCl (3 ml) for 30 min. The pH of the solution was adjusted with 3N NaOH (3 ml) and the reaction mixture was treated with a solution of NaIO$_4$ (1.10 g) in water (10 ml). The temperature of the reaction was kept below +30°

C. by intermittent cooling with an ice-water bath. The reaction mixture was further stirred at rt for 30 min. The reaction mixture was extracted with water and EA. The org. layer was washed with brine, dried over MgSO$_4$ and concentrated under reduced pressure. The residue was then stirred in TBME, affording a colourless solid (0.856 g; 79% yield).
MS (ESI, m/z): 253.3 [M+H$^+$].

Preparation R: 3-(2-amino-ethyl)-8-chloro-1H-quinazoline-2,4-dione

R.i.
[2-(2-amino-3-chloro-benzoylamino)-ethyl]-carbamic acid tert-butyl ester

Starting from 8-chloro-1-methyl-2H-3,1-benzoxazine-2,4 (1H)-dione and N-Boc-ethylenediamine and using Procedure S, the title intermediate was obtained as a colourless solid (264 mg; 84% yield).
MS (ESI, m/z): 314.0 [M+H$^+$].

R.ii. [2-(8-chloro-2,4-dioxo-1,4-dihydro-2H-quinazolin-3-yl)-ethyl]-carbamic acid tert-butyl ester Starting from intermediate R.i and using Procedure T, the title intermediate was obtained as a colourless solid (145 mg; 53% yield).
MS (ESI, m/z): 338.0 [M+H$^+$].

R.iii. 3-(2-amino-ethyl)-8-chloro-1H-quinazoline-2, 4-dione

Starting from intermediate R.ii and using Procedure U2, the title intermediate was obtained as a colourless solid (91 mg; 90% yield).
MS (ESI, m/z): 240.2 [M+H$^+$].

Preparation S: (E)-3-[1-methyl-2,4-dioxo-3-(2-oxo-ethyl)-1,2,3,4-tetrahydro-quinazolin-7-yl]-acrylic acid methyl ester S.i. 7-bromo-1-methyl-1H-quinazoline-2,4-dione Starting from 7-bromo-1-methyl-1H-benzo[d][1,3]oxazine-2,4-dione (prepared according to WO 2007/070359) and using Procedure R, the title intermediate was obtained as a light yellow solid (14.5 g; 59% yield).
$^1$H NMR (DMSO-d$_6$) δ: 11.54 (s, 1H), 7.86 (d, J=8.4 Hz, 1H), 7.62 (d, J=1.7 Hz, 1H), 7.42 (dd, J=8.3, 1.7 Hz, 1H), 3.41 (s, 3H).

S.ii. rac-7-bromo-3-(2,2-dimethyl-[1,3]dioxolan-4-ylmethyl)-1-methyl-1H-quinazoline-2,4-dione Starting from intermediate S.i and 2,2-dimethyl-1,3-dioxolane-4-methanol and using Procedure V, the title intermediate was obtained as a colourless solid (7.50 g; 36% yield).
$^1$H NMR (DMSO-d$_6$) δ: 8.05 (m, 1H), 7.37 (m, 1H), 7.15 (m, 1H), 4.46 (m, 2H), 4.05 (m, 2H), 3.85 (m, 1H), 3.56 (s, 3H), 1.46 (s, 3H), 1.31 (s, 3H).

S.iii. rac-(E)-3-[3-(2,2-dimethyl-[1,3]dioxolan-4-ylmethyl)-1-methyl-2,4-dioxo-1,2,3,4-tetrahydro-quinazolin-7-yl]-acrylic acid methyl ester To a suspension of intermediate S.ii (500 mg), Pd(OAc)$_2$ (10.4 mg) and tri-(ortho-tolyl)-phosphine (41.2 mg) in DMF (6.75 ml) were added TEA (0.566 ml) and methyl acrylate (0.617 ml). The mixture was stirred at 120° C. for 1.5 h. The reaction mixture was concentrated in vacuo and the residue was partitioned between EA and water. The layers were separated and the aq. layer was extracted twice with EA. The combined org. layers were washed with water, brine and dried over MgSO$_4$, concentrated under reduced pressure and the residue was stirred in ether, affording a beige solid (0.470 g; 93% yield).
$^1$H NMR (CDCl$_3$) δ: 8.22 (d, J=8.2 Hz, 1H), 7.73 (d, J=16.0 Hz, 1H), 7.41 (dd, J=1.4, 8.2 Hz, 1H), 7.25 (m, 1H), 6.57 (d, J=16.0 Hz, 1H), 4.40-4.57 (m, 2H), 4.00-4.12 (m, 2H), 3.85-3.90 (m, 1H), 3.84 (s, 3H), 3.62 (s, 3H), 1.47 (s, 3H), 1.32 (s, 3H).

S.iv. (E)-3-[1-methyl-2,4-dioxo-3-(2-oxo-ethyl)-1,2,3,4-tetrahydro-quinazolin-7-yl]-acrylic acid methyl ester A solution of intermediate S.iii (450 mg) in dioxane (4 ml) was stirred in 3N HCl (0.8 ml) for 30 min. The pH of the solution was adjusted with 3N NaOH (0.8 ml) and the reaction mixture was treated with a solution of NaIO$_4$ (308 mg) in water (3 ml). The temperature of the reaction was kept below +30° C. by intermittent cooling with an ice-water bath. The reaction mixture was further stirred at rt for 30 min, diluted with water and filtered affording 340 mg (93%) of a colourless solid.
MS (ESI, m/z): 303.3 [M+H$^+$].

Preparation T: 1,3-dioxo-6,7-dihydro-1H,5H-pyrido [3,2,1-ij]quinazolin-2-yl)-acetaldehyde T.i. 2-allyl-6,7-dihydro-5H-pyrido[3,2,1-ij]quinazoline-1,3-dione Starting from 6,7-dihydropyrido[3,2,1-ij]quinazoline-1,3 (2H,5H)-dione (prepared according to WO 2010/079206) and allyl bromide and using Procedure E, the title intermediate was obtained as a colourless solid (0.393 g; 89% yield).
MS (ESI, m/z): 243.3 [M+H$^+$].

T.ii. rac-2-(2,3-dihydroxy-propyl)-6,7-dihydro-5H-pyrido[3,2,1-ij]quinazoline-1,3-dione Starting from intermediate T.i and using Procedure L, the title intermediate was obtained as a black solid (0.415 g; 96% yield).
MS (ESI, m/z): 277.3 [M+H$^+$].

T.iii. 1,3-dioxo-6,7-dihydro-1H,5H-pyrido[3,2,1-ij] quinazolin-2-yl)-acetaldehyde Starting from intermediate T.ii and using Procedure Q, the title compound was obtained as a grey solid (0.345 g; 98% yield).
MS (ESI, m/z): 245.3 [M+H$^+$].

Examples of Compounds According to the Invention

Example 1

3-{3-[(S)-2-oxo-3-(3-oxo-3,4-dihydro-2H-benzo[1,4]thiazin-6-yl)-oxazolidin-5-yl]-propyl}-1H-quinazoline-2,4-dione 1.i. 2-amino-N-{3-[(S)-2-oxo-3-(3-oxo-3,4-dihydro-2H-benzo[1,4]thiazin-6-yl)-oxazolidin-5-yl]-propyl}-benzamide Starting from the compound of Preparation A and isatoic anhydride and using Procedure A, the title compound was obtained as a colourless solid (390 mg; 91% yield).
MS (ESI, m/z): 427.2 [M+H$^+$].

1.ii. 3-{3-[(S)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 1.i and using Procedure B, the title compound was obtained as a colourless solid (42 mg; 40% yield).

$^1$H NMR (DMSO-d$_6$) δ: 11.40 (s, 1H), 10.52 (s, 1H), 7.92 (dd, J=1.2, 7.8 Hz, 1H), 7.60-7.68 (m, 1H), 7.25-7.32 (m, 3H), 7.15-7.2 (m, 2H), 7.06 (dd, J=2.3, 8.6 Hz, 1H), 4.69 (m, 1H), 4.05 (t, J=8.6 Hz, 1H), 3.90-3.97 (m, 2H), 3.63 (dd, J=7.3, 8.8 Hz, 1H), 3.40 (s, 2H), 1.74 (m, 4H).

HR LC-MS: MS (ESI, m/z): 453.1245 [M+H$^+$]; t$_R$=1.32 min.

Example 2

1-methyl-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione

2.i. 2-methylamino-N-{3-[(S)-2-oxo-3-(3-oxo-3,4-dihydro-2H-pyrido[3,2-b][1,4]thiazin-6-yl)-oxazolidin-5-yl]-propyl}-benzamide Starting from the compound of Preparation B and N-methyl isatoic anhydride and using Procedure A, the title compound was obtained as a colourless solid (123 mg; 51% yield).

MS (ESI, m/z): 442.2 [M+H$^+$].

2.ii. 1-methyl-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione Starting from intermediate 2.i and using Procedure B, the title compound was obtained as a light pink solid (17 mg; 61% yield).

$^1$H NMR (DMSO-d$_6$) δ: 10.83 (br s, 1H), 8.04 (dd, J=1.3, 7.8 Hz, 1H), 7.71-7.81 (m, 2H), 7.61-7.68 (m, 1H), 7.43 (d, J=8.4 Hz, 1H), 7.29 (t, J=7.5 Hz, 1H), 4.63-4.79 (m, 1H), 4.13-4.23 (m, 1H), 4.00 (t, J=6.8 Hz, 2H), 3.69 (dd, J=7.2, 10.2 Hz, 1H), 3.50 (s, 5H), 1.57-1.87 (m, 4H).

MS (ESI, m/z): 468.3 [M+H$^+$].

Example 3

1-methyl-3-{3-[(S)-2-oxo-3-(3-oxo-3,4-dihydro-2H-benzo[1,4]-thiazin-6-yl)-oxazolidin-5-yl]-propyl}-1H-quinazoline-2,4-dione

3.i. 2-methylamino-N-{3-[(S)-2-oxo-3-(3-oxo-3,4-dihydro-2H-benzo[1,4]thiazin-6-yl)-oxazolidin-5-yl]-propyl}-benzamide Starting from the compound of Preparation A and N-methyl isatoic anhydride and using Procedure A, the title compound was obtained as a colourless solid (144 mg; 92% yield).

MS (ESI, m/z): 441.4 [M+H$^+$].

3.ii. Methyl-(2-{3-[(S)-2-oxo-3-(3-oxo-3,4-dihydro-2H-benzo[1,4]thiazin-6-yl)-oxazolidin-5-yl]-propyl-carbamoyl}-phenyl)-carbamic acid methyl ester A solution of intermediate 3.i (141 mg; 0.32 mmol) in THF (4 ml) and DCM/MeOH 9:1 (2 ml) was treated with TEA (0.09 ml, 0.64 mmol) and triphosgene (190 mg, 0.64 mmol). After stirring for 3 h at 65° C., the reaction mixture was quenched with sat. aq. NaHCO$_3$ and extracted with DCM/MeOH 9:1. The org. layer was separated, dried over MgSO$_4$ concentrated and purified by CC (Hept/EA 1:2 to 0:1), affording a colourless foam (154 mg, 97% yield).

MS (ESI, m/z): 499.4 [M+H$^+$].

3.iii. 1-methyl-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 3.ii and using Procedure C, the title compound was obtained as a light yellow solid (33 mg; 27% yield).

$^1$H NMR (DMSO-d$_6$) δ: 10.53 (br. s, 1H), 8.01-8.07 (m, 1H), 7.71-7.81 (m, 1H), 7.44 (d, J=8.5 Hz, 1H), 7.24-7.33 (m, 3H), 7.03-7.09 (m, 1H), 4.60-4.74 (m, 1H), 3.94-4.10 (m, 3H), 3.57-3.66 (m, 1H), 3.51 (s, 3H), 3.41 (s, 2H), 1.61-1.85 (m, 4H).

MS (ESI, m/z): 467.5 [M+H$^+$].

Example 4

3-{3-[(R)-2-oxo-3-(3-oxo-3,4-dihydro-2H-benzo[1,4]-thiazin-6-yl)-oxazolidin-5-yl]-propyl}-1-propyl-1H-quinazoline-2,4-dione

4.i. N-{3-[(R)-2-oxo-3-(3-oxo-3,4-dihydro-2H-benzo[1,4]thiazin-6-yl)-oxazolidin-5-yl]-propyl}-2-propylamino-benzamide Starting from 6-[(R)-5-(3-amino-propyl)-2-oxo-oxazolidin-3-yl]-4H-benzo[1,4]thiazin-3-one (described in WO 2010/041219) and N-propylisatoic anhydride and using Procedure A, the title compound was obtained as a beige solid (77 mg; 67% yield).

MS (ESI, m/z): 469.3 [M+H$^+$].

4.ii. 3-{3-[(R)-2-oxo-3-(3-oxo-3,4-dihydro-2H-benzo[1,4]thiazin-6-yl)-oxazolidin-5-yl]-propyl}-1-propyl-1H-quinazoline-2,4-dione:

Starting from intermediate 4.i and using Procedure B, the title compound was obtained as a brown solid (27 mg; 36% yield).

$^1$H NMR (DMSO-d$_6$) δ: 10.54 (br. s, 1H), 7.92-8.00 (m, 1H), 7.53-7.63 (m, 1H), 7.25-7.37 (m, 3H), 7.13-7.22 (m, 1H), 7.02-7.10 (m, 1H), 4.59-4.80 (m, 1H), 4.04-4.15 (m, 1H), 3.82-3.94 (m, 2H), 3.60-3.73 (m, 1H), 3.46-3.54 (m, 2H), 3.41 (s, 2H), 1.52-1.91 (m, 6H), 1.07 (t, J=7.0 Hz, 3H).

HR LC-MS: MS (ESI, m/z): 495.1697 [M+H$^+$]; t$_R$=1.66 min.

Example 5

5-methyl-3-{3-[(R)-2-oxo-3-(3-oxo-3,4-dihydro-2H-benzo[1,4]-thiazin-6-yl)-oxazolidin-5-yl]-propyl}-1H-quinazoline-2,4-dione

5.i. 2-amino-6-methyl-N-{3-[(R)-2-oxo-3-(3-oxo-3,4-dihydro-2H-benzo[1,4]thiazin-6-yl)-oxazolidin-5-yl]-propyl}-benzamide Starting from 2-amino-6-methylbenzoic acid and 6-[(R)-5-(3-amino-propyl)-2-oxo-oxazolidin-3-yl]-4H-benzo[1,4]

thiazin-3-one (described in WO 2010/041219) and using Procedure D, the title compound was obtained as a beige solid (180 mg; 77% yield).
MS (ESI, m/z): 441.4 [M+H$^+$].

5.ii. 5-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 5.i and using Procedure B, the title compound was obtained as a beige solid (38 mg; 54% yield).
$^1$H NMR (DMSO-d$_6$) δ: 7.43 (t, J=8.0 Hz, 1H), 7.24-7.36 (m, 2H), 7.04-7.11 (m, 1H), 7.00 (d, J=7.8 Hz, 1H), 6.89-6.96 (m, 1H), 4.60-4.75 (m, 1H), 4.01-4.11 (m, 1H), 3.86-3.96 (m, 2H), 3.58-3.68 (m, 1H), 3.41 (s, 2H), 2.66 (s, 3H), 1.54-1.85 (m, 4H).
HR LC-MS: MS (ESI, m/z): 467.1396 [M+H$^+$]; t$_R$=1.46 min.

Example 6

1,5-dimethyl-3-{3-[(S)-2-oxo-3-(3-oxo-3,4-dihydro-2H-benzo[1,4]-thiazin-6-yl)-oxazolidin-5-yl]-propyl}-1H-quinazoline-2,4-dione

6.i. (S)-2-methyl-6-(methylamino)-N-(3-(2-oxo-3-(3-oxo-3,4-dihydro-2H-benzo[b][1,4]thiazin-6-yl)oxazolidin-5-yl)propyl)benzamide Starting from the compound of Preparation A and 1,5-dimethyl-2H-3,1-benzoxazine-2,4(1H)-dione (prepared according to WO 98/42688) and using Procedure A, the title compound was obtained as a beige solid (70 mg; 56% yield).
MS (ESI, m/z): 455.3 [M+H$^+$].

6.ii. 1,5-dimethyl-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 6.i and using Procedure B, the title compound was obtained as a colourless solid (16 mg; 25% yield).
$^1$H NMR (DMSO-d$_6$) δ: 10.53 (br. s, 1H), 7.39-7.51 (m, 1H), 7.24-7.38 (m, 2H), 7.02-7.17 (m, 3H), 4.65-4.80 (m, 1H), 4.04-4.18 (m, 1H), 3.60-3.73 (m, 1H), 3.50-3.60 (m, 2H), 3.42 (s, 2H), 3.36 (s, 3H), 2.61 (s, 3H), 1.80-1.93 (m, 2H), 1.63-1.80 (m, 2H).
HR LC-MS: MS (ESI, m/z): 481.1548 [M+H$^+$]; t$_R$=1.70 min.

Example 7

5-methyl-3-{3-[(S)-2-oxo-3-(3-oxo-3,4-dihydro-2H-benzo[1,4]-thiazin-6-yl)-oxazolidin-5-yl]-propyl}-1H-quinazoline-2,4-dione

7.i. 2-amino-6-methyl-N-{3-[(S)-2-oxo-3-(3-oxo-3,4-dihydro-2H-benzo[1,4]thiazin-6-yl)-oxazolidin-5-yl]-propyl}-benzamide Starting from the compound of Preparation A and 5-methyl-1H-benzo[d][1,3]oxazine-2,4-dione and using Procedure A, the title compound was obtained as a yellow foam (203 mg; 92% yield).
MS (ESI, m/z): 441.0 [M+H$^+$].

7.ii. 5-methyl-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 7.i and using Procedure B, the title compound was obtained as a brown solid (18 mg; 20% yield).
HR LC-MS: MS (ESI, m/z): 467.1397 [M+H$^+$]; t$_R$=1.46 min.

Example 8

5-methyl-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione

8.i. 2-amino-6-methyl-N-{3-[(S)-2-oxo-3-(3-oxo-3,4-dihydro-2H-pyrido[3,2-b][1,4]thiazin-6-yl)-oxazolidin-5-yl]-propyl}-benzamide Starting from the compound of Preparation B and 5-methyl-1H-benzo[d][1,3]oxazine-2,4-dione and using Procedure A, the title compound was obtained as a yellowish foam (167 mg; 76% yield).
MS (ESI, m/z): 442.0 [M+H$^+$].

8.ii. 5-methyl-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione Starting from intermediate 8.i and using Procedure B, the title compound was obtained as a pink solid (65 mg; 77% yield).
HR LC-MS: MS (ESI, m/z): 468.1342 [M+H$^+$]; t$_R$=1.48 min.

Example 9

5-methyl-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione

9.i. 2-amino-6-methyl-N-{3-[(R)-2-oxo-3-(3-oxo-3,4-dihydro-2H-pyrido[3,2-b][1,4]oxazin-6-yl)-oxazolidin-5-yl]-propyl}-benzamide Starting from the compound of Preparation C and 5-methyl-1H-benzo[d][1,3]oxazine-2,4-dione and using Procedure A, the title compound was obtained as a colourless solid (112 mg; 88% yield).
MS (ESI, m/z): 426.0 [M+H$^+$].

9.ii. 5-methyl-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione Starting from intermediate 9.i and using Procedure B, the title compound was obtained as a colourless solid (41 mg; 46% yield).
$^1$H NMR (DMSO-d$_6$) δ: 7.49 (d, J=8.5 Hz, 1H), 7.40 (t, J=7.8 Hz, 1H), 7.32 (d, J=8.6 Hz, 1H), 6.97 (d, J=8.1 Hz, 1H), 6.89 (d, J=7.3 Hz, 1H), 4.61-4.75 (m, 1H), 4.51 (s, 2H), 4.11-4.24 (m, 1H), 3.85-3.94 (m, 2H), 3.69 (dd, J=7.2, 10.1 Hz, 1H), 2.65 (s, 3H), 1.54-1.85 (m, 4H).
HR LC-MS: MS (ESI, m/z): 452.1575 [M+H$^+$]; t$_R$=1.40 min.

Example 10

6-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione

10.i. 2-amino-5-methyl-N-{3-[(R)-2-oxo-3-(3-oxo-3,4-dihydro-2H-benzo[1,4]thiazin-6-yl)-oxazolidin-5-yl]-propyl}-benzamide Starting from 2-amino-5-methylbenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (130 mg; 56% yield).

MS (ESI, m/z): 441.3 [M+H$^+$].

10.ii. 6-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 10.i and using Procedure B, the title compound was obtained as a beige solid (45 mg; 64% yield).

$^1$H NMR (DMSO-d$_6$) δ: 7.62 (dd, J=0.4, 1.3 Hz, 1H), 7.22-7.36 (m, 3H), 7.03-7.11 (m, 1H), 6.90-6.98 (m, 1H), 4.59-4.76 (m, 1H), 4.00-4.11 (m, 1H), 3.87-3.97 (m, 2H), 3.57-3.68 (m, 1H), 3.15 (s, 2H), 2.27 (s, 3H), 1.56-1.82 (m, 4H).

HR LC-MS: MS (ESI, m/z): 467.1392 [M+H$^+$]; t$_R$=1.41 min.

Example 11

7-methyl-3-{3-[(R)-2-oxo-3-(3-oxo-3,4-dihydro-2H-benzo[1,4]-thiazin-6-yl)-oxazolidin-5-yl]-propyl}-1H-quinazoline-2,4-dione

11.i. 2-amino-4-methyl-N-{3-[(R)-2-oxo-3-(3-oxo-3,4-dihydro-2H-benzo[1,4]thiazin-6-yl)-oxazolidin-5-yl]-propyl}-benzamide Starting from 2-amino-4-methylbenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (116 mg; 82% yield).

MS (ESI, m/z): 441.3 [M+H$^+$].

11.ii. 7-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 11.i and using Procedure B, the title compound was obtained as a pink solid (65 mg; 61% yield).

$^1$H NMR (DMSO-d$_6$) δ: 11.34 (br. s, 1H), 10.52 (br. s, 1H), 7.80 (d, J=8.0 Hz, 1H), 7.21-7.41 (m, 2H), 6.99-7.12 (m, 2H), 6.95 (s, 1H), 4.61-4.78 (m, 1H), 4.01-4.13 (m, 1H), 3.86-3.98 (m, 2H), 3.55-3.70 (m, 1H), 3.41 (s, 2H), 2.35 (s, 3H), 1.50-1.97 (m, 4H).

HR LC-MS: MS (ESI, m/z): 467.1386 [M+H$^+$]; t$_R$=1.40 min.

Example 12

8-methyl-3-{3-[(R)-2-oxo-3-(3-oxo-3,4-dihydro-2H-benzo[1,4]-thiazin-6-yl)-oxazolidin-5-yl]-propyl}-1H-quinazoline-2,4-dione

12.i. 2-amino-4-methyl-N-{3-[(R)-2-oxo-3-(3-oxo-3,4-dihydro-2H-benzo[1,4]thiazin-6-yl)-oxazolidin-5-yl]-propyl}-benzamide Starting from 2-amino-3-methylbenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (234 mg; 100% yield).

MS (ESI, m/z): 441.3 [M+H$^+$].

12.ii. 8-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 12.i and using Procedure B, the title compound was obtained as a beige solid (5 mg; 7% yield).

$^1$H NMR (DMSO-d$_6$) δ: 10.64 (br. s, 1H), 10.53 (br. s, 1H), 7.76-7.84 (m, 1H), 7.44-7.53 (m, 1H), 7.25-7.34 (m, 2H), 7.02-7.16 (m, 2H), 4.58-4.78 (m, 1H), 4.01-4.11 (m, 1H), 3.91-4.01 (m, 2H), 3.56-3.69 (m, 1H), 3.41 (s, 2H), 2.34 (s, 3H), 1.61-1.84 (m, 4H).

HR LC-MS: MS (ESI, m/z): 467.1395 [M+H$^+$]; t$_R$=1.41 min.

Example 13

8-methyl-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione

13.i. 2-amino-3-methyl-N-{3-[(S)-2-oxo-3-(3-oxo-3,4-dihydro-2H-benzo[1,4]thiazin-6-yl)-oxazolidin-5-yl]-propyl}-benzamide Starting from the compound of Preparation A and 8-methyl-1H-benzo[d][1,3]oxazine-2,4-dione and using Procedure A, the title compound was obtained as a colourless solid (109 mg; 82% yield).

MS (ESI, m/z): 441.1 [M+H$^+$].

13.ii. 8-methyl-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 13.i and using Procedure B, the title compound was obtained as a pink solid (76 mg; 82% yield).

$^1$H NMR (DMSO-d$_6$) δ: 10.64 (br. s, 1H), 10.52 (br. s, 1H), 7.75-7.84 (m, 1H), 7.44-7.51 (m, 1H), 7.24-7.34 (m, 2H), 7.02-7.15 (m, 2H), 4.62-4.77 (m, 1H), 4.06 (t, J=8.7 Hz, 1H), 3.91-4.01 (m, 2H), 3.63 (dd, J=7.1, 8.6 Hz, 1H), 3.41 (s, 2H), 2.34 (s, 3H), 1.62-1.86 (m, 4H).

HR LC-MS: MS (ESI, m/z): 467.1392 [M+H$^+$]; t$_R$=1.41 min.

Example 14

8-methyl-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione:

14.i. 2-amino-3-methyl-N-{3-[(S)-2-oxo-3-(3-oxo-3,4-dihydro-2H-pyrido[3,2-b][1,4]thiazin-6-yl)-oxazolidin-5-yl]-propyl}-benzamide Starting from the compound of Preparation B and 8-methyl-1H-benzo[d][1,3]oxazine-2,4-dione and using Procedure A, the title compound was obtained as a colourless solid (85 mg; 64% yield).
MS (ESI, m/z): 442.1 [M+H$^+$].

14.ii. 8-methyl-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione Starting from intermediate 14.i and using Procedure B, the title compound was obtained as a colourless solid (81 mg; 96% yield).
HR LC-MS: MS (ESI, m/z): 468.1349 [M+H$^+$]; $t_R$=1.43 min.

Example 15

8-methyl-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione

15.i. 2-amino-3-methyl-N-{3-[(R)-2-oxo-3-(3-oxo-3,4-dihydro-2H-pyrido[3,2-b][1,4]oxazin-6-yl)-oxazolidin-5-yl]-propyl}-benzamide Starting from the compound of Preparation C and 8-methyl-1H-benzo[d][1,3]oxazine-2,4-dione and using Procedure A, the title compound was obtained as a colourless foam (62 mg; 49% yield).
MS (ESI, m/z): 426.1 [M+H$^+$].

15.ii. 8-methyl-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione Starting from intermediate 15.i and using Procedure B, the title compound was obtained as a colourless solid (41 mg; 71% yield).
HR LC-MS: MS (ESI, m/z): 452.1568 [M+H$^+$]; $t_R$=1.34 min.

Example 16

5-chloro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione

16.i. 2-amino-6-chloro-N-{3-[(R)-2-oxo-3-(3-oxo-3,4-dihydro-2H-benzo[1,4]thiazin-6-yl)-oxazolidin-5-yl]-propyl}-benzamide Starting from 2-amino-6-chlorobenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (100 mg; 46% yield).
MS (ESI, m/z): 461.1 [M+H$^+$].

16.ii. 5-chloro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 16.i and using Procedure B, the title compound was obtained as a beige solid (28 mg; 38% yield).
$^1$H NMR (DMSO-d$_6$) δ: 11.50 (br. s, 1H), 10.53 (br. s, 1H), 7.50-7.60 (m, 1H), 7.24-7.37 (m, 2H), 7.16-7.24 (m, 1H), 7.02-7.16 (m, 2H), 4.60-4.79 (m, 1H), 4.00-4.12 (m, 1H), 3.84-3.95 (m, 2H), 3.57-3.69 (m, 1H), 3.41 (s, 2H), 1.55-1.87 (m, 4H).
HR LC-MS: MS (ESI, m/z): 487.0841 [M+H$^+$]; $t_R$=1.41 min.

Example 17

5-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione

17.i. 2-amino-6-fluoro-N-{3-[(R)-2-oxo-3-(3-oxo-3,4-dihydro-2H-benzo[1,4]thiazin-6-yl)-oxazolidin-5-yl]-propyl}-benzamide Starting from 2-amino-6-fluorobenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (190 mg; 83% yield).
MS (ESI, m/z): 445.1 [M+H$^+$].

17.ii. 5-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 17.i and using Procedure B, the title compound was obtained as a beige solid (13 mg; 18% yield).
$^1$H NMR (DMSO-d$_6$) δ: 11.53 (br. s, 1H), 10.53 (br. s, 1H), 7.53-7.68 (m, 1H), 7.23-7.39 (m, 2H), 7.07 (dd, J=2.3, 8.6 Hz, 1H), 6.87-7.00 (m, 2H), 4.61-4.75 (m, 1H), 4.06 (t, J=8.7 Hz, 1H), 3.84-3.95 (m, 2H), 3.56-3.68 (m, 1H), 3.41 (s, 2H), 1.51-1.88 (m, 4H).
HR LC-MS: MS (ESI, m/z): 471.1136 [M+H$^+$]; $t_R$=1.30 min.

Example 18

5-chloro-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione

18.i. 2-amino-6-chloro-N-{3-[(S)-2-oxo-3-(3-oxo-3,4-dihydro-2H-benzo[1,4]thiazin-6-yl)-oxazolidin-5-yl]-propyl}-benzamide Starting from the compound of Preparation A and 5-chloro-1H-benzo[d][1,3]oxazine-2,4-dione and using Procedure A, the title compound was obtained as a colourless foam (78 mg; 56% yield).
MS (ESI, m/z): 461.0 [M+H$^+$].

18.ii. 5-chloro-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 18.i and using Procedure B, the title compound was obtained as a yellowish solid (21 mg; 29% yield).

¹H NMR (DMSO-d₆) δ: 11.52 (br. s, 1H), 10.53 (br. s, 1H), 7.54 (t, J=8.1 Hz, 1H), 7.25-7.36 (m, 2H), 7.21 (dd, J=0.8, 7.9 Hz, 1H), 7.13 (dd, J=0.8, 8.2 Hz, 1H), 7.07 (dd, J=2.3, 8.5 Hz, 1H), 4.60-4.75 (m, 1H), 4.06 (t, J=8.7 Hz, 1H), 3.85-3.96 (m, 2H), 3.58-3.79 (m, 1H), 3.41 (s, 2H), 1.58-1.82 (m, 4H).

HR LC-MS: MS (ESI, m/z): 487.0845 [M+H⁺]; $t_R$=1.41 min.

Example 19

5-chloro-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione 19.i. 2-amino-6-chloro-N-{3-[(S)-2-oxo-3-(3-oxo-3,4-dihydro-2H-pyrido[3,2-b][1,4]thiazin-6-yl)-oxazolidin-5-yl]-propyl}-benzamide Starting from the compound of Preparation B and 5-chloro-1H-benzo[d][1,3]oxazine-2,4-dione and using Procedure A, the title compound was obtained as a colourless foam (79 mg; 57% yield).

MS (ESI, m/z): 462.0 [M+H⁺].

19.ii. 5-chloro-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione Starting from intermediate 19.i and using Procedure B, the title compound was obtained as a colourless solid (24 mg; 38% yield).

HR LC-MS: MS (ESI, m/z): 488.0796 [M+H⁺]; $t_R$=1.43 min.

Example 20

5-chloro-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione 20.i. 2-amino-6-chloro-N-{3-[(R)-2-oxo-3-(3-oxo-3,4-dihydro-2H-pyrido[3,2-b][1,4]oxazin-6-yl)-oxazolidin-5-yl]-propyl}-benzamide Starting from the compound of Preparation C and 5-chloro-1H-benzo[d][1,3]oxazine-2,4-dione and using Procedure A, the title compound was obtained as a colourless solid (84 mg; 63% yield).

MS (ESI, m/z): 446.0 [M+H⁺].

20.ii. 5-chloro-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione Starting from intermediate 20.i and using Procedure B, the title compound was obtained as a colourless solid (58 mg; 72% yield).

¹H NMR (DMSO-d₆) δ: 11.51 (br. s, 1H), 11.16 (br. s, 1H), 7.50-7.60 (m, 2H), 7.36-7.43 (m, 1H), 7.21 (dd, J=0.7, 7.8 Hz, 1H), 7.12 (dd, J=0.8, 8.2 Hz, 1H), 4.62-4.77 (m, 1H), 4.58 (s, 2H), 4.12-4.23 (m, 1H), 3.83-3.96 (m, 2H), 3.70 (dd, J=7.2, 10.1 Hz, 1H), 1.53-1.86 (m, 4H).

HR LC-MS: MS (ESI, m/z): 472.103 [M+H⁺]; $t_R$=1.34 min.

Example 21

8-chloro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione 21.i. 2-amino-3-chloro-N-{3-[(R)-2-oxo-3-(3-oxo-3,4-dihydro-2H-benzo[1,4]thiazin-6-yl)-oxazolidin-5-yl]-propyl}-benzamide Starting from 6-[(R)-5-(3-amino-propyl)-2-oxo-oxazolidin-3-yl]-4H-benzo[1,4]thiazin-3-one (described in WO 2010/041219) and 8-chloro-1H-benzo[d][1,3]oxazine-2,4-dione and using Procedure A, the title compound was obtained as a colourless solid (97 mg; 70% yield).

MS (ESI, m/z): 461.1 [M+H⁺].

21.ii. 8-chloro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 21.i and using Procedure B, the title compound was obtained as a colourless solid (56 mg; 57% yield).

¹H NMR (DMSO-d₆) δ: 10.94 (br. s, 1H), 10.53 (br. s, 1H), 7.92 (dd, J=1.4, 7.9 Hz, 1H), 7.78 (dd, J=1.4, 7.9 Hz, 1H), 7.25-7.34 (m, 2H), 7.20 (t, J=7.9 Hz, 1H), 7.06 (dd, J=2.4, 8.6 Hz, 1H), 4.60-4.76 (m, 1H), 4.06 (t, J=8.6 Hz, 1H), 3.90-4.00 (m, 2H), 3.62 (dd, J=7.2, 8.8 Hz, 1H), 3.41 (s, 2H), 1.58-1.86 (m, 4H).

HR LC-MS: MS (ESI, m/z): 487.0844 [M+H⁺]; $t_R$=1.44 min.

Example 22

8-chloro-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione 22.i. 2-amino-3-chloro-N-{3-[(S)-2-oxo-3-(3-oxo-3,-dihydro-2H-pyrido[3,2-b][1,4]thiazin-6-yl)-oxazolidin-5-yl]-propyl}-benzamide Starting from the compound of Preparation B and 8-chloro-1H-benzo[d][1,3]oxazine-2,4-dione and using Procedure A, the title compound was obtained as a colourless solid (71 mg; 51% yield).

MS (ESI, m/z): 462.1 [M+H⁺].

22.ii. 8-chloro-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione Starting from intermediate 22.i. and using procedure B, the title compound was obtained as a colourless solid (40 mg; 59% yield).

¹H NMR (DMSO-d₆) δ: 10.93 (br. s, 1H), 10.83 (br. s, 1H), 7.92 (dd, J=1.4, 7.9 Hz, 1H), 7.72-7.83 (m, 2H), 7.62-7.69 (m, 1H), 7.20 (t, J=7.9 Hz, 1H), 4.63-4.80 (m, 1H), 4.13-4.24 (m, 1H), 3.90-4.00 (m, 2H), 3.69 (dd, J=7.0, 10.3 Hz, 1H), 3.50 (s, 2H), 1.58-1.91 (m, 4H).

HR LC-MS: MS (ESI, m/z): 488.0793 [M+H⁺]; $t_R$=1.47 min.

Example 23

8-chloro-3-{3-[(R)-2-oxo-3-(3-oxo-3,4-dihydro-2H-pyrido[3,2-b][1,4]oxazine-6-yl)-oxazolidin-5-yl]-propyl}-1H-quinazoline-2,4-dione

23.i. 2-amino-3-chloro-N-{3-[(R)-2-oxo-3-(3-oxo-3,4-dihydro-2H-pyrido[3,2-b][1,4]oxazine-6-yl)-oxazolidin-5-yl]-propyl}-benzamide Starting from the compound of Preparation C and 8-chloro-1H-benzo[d][1,3]oxazine-2,4-dione and using Procedure A, the title compound was obtained as a colourless solid (110 mg; 82% yield).

MS (ESI, m/z): 446.1 [M+H$^+$].

23.ii. 8-chloro-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione Starting from intermediate 23.i and using Procedure B, the title compound was obtained as a colourless solid (82 mg; 76% yield).

$^1$H NMR (DMSO-d$_6$) δ: 11.16 (br. s, 1H), 10.93 (br. s, 1H), 7.92 (dd, J=1.3 Hz, 8.0 Hz, 1H), 7.78 (dd, J=1.4, 7.9 Hz, 1H), 7.56 (m, 1H), 7.39 (m, 1H), 7.20 (t, J=7.9 Hz, 1H), 4.60-4.78 (m, 1H), 4.58 (s, 2H), 4.12-4.23 (m, 1H), 3.88-4.00 (m, 2H), 3.69 (dd, J=7.1, 10.1 Hz, 1H), 1.54-1.86 (m, 4H).

HR LC-MS: MS (ESI, m/z): 472.1031 [M+H$^+$]; t$_R$=1.37 min.

Example 24

8-chloro-3-{3-[(S)-2-oxo-3-(3-oxo-3,4-dihydro-2H-pyrido[3,2-b][1,4]oxazine-6-yl)-oxazolidin-5-yl]-propyl}-1H-quinazoline-2,4-dione

24.i. 2-amino-3-chloro-N-{3-[(S)-2-oxo-3-(3-oxo-3,4-dihydro-2H-pyrido[3,2-b][1,4]oxazine-6-yl)-oxazolidin-5-yl]-propyl}-benzamide Starting from the compound of Preparation D and 8-chloro-1H-benzo[d][1,3]oxazine-2,4-dione and using Procedure A, the title compound was obtained as a colourless solid (100 mg; 75% yield).

MS (ESI, m/z): 446.1 [M+H$^+$].

24.ii. 8-chloro-3-{3-[(S)-2-oxo-3-(3-oxo-3,4-dihydro-2H-pyrido[3,2-b][1,4]oxazin-6-yl)-oxazolidin-5-yl]-propyl}-1H-quinazoline-2,4-dione Starting from intermediate 24.i and using Procedure B, the title compound was obtained as a colourless solid (67 mg; 68% yield).

$^1$H NMR (DMSO-d$_6$) δ: 11.16 (br. s, 1H), 10.93 (br. s, 1H), 7.92 (dd, J=1.3, 7.9 Hz, 1H), 7.78 (dd, J=1.4, 7.9 Hz, 1H), 7.56 (d, J=8.5 Hz, 1H), 7.39 (d, J=8.7 Hz, 1H), 7.20 (t, J=7.9 Hz, 1H), 4.60-4.75 (m, 1H), 4.58 (s, 2H), 4.12-4.22 (m, 1H), 3.90-3.99 (m, 2H), 3.69 (dd, J=7.1, 10.1 Hz, 1H), 1.58-1.86 (m, 4H).

HR LC-MS: MS (ESI, m/z): 472.1033 [M+H$^+$]; t$_R$=1.37 min.

Example 25

6-chloro-3-{3-[(R)-2-oxo-3-(3-oxo-3,4-dihydro-2H-benzo[1,4]-thiazin-6-yl)-oxazolidin-5-yl]-propyl}-1H-quinazoline-2,4-dione

25.i. 2-amino-5-chloro-N-{3-[(R)-2-oxo-3-(3-oxo-3,4-dihydro-2H-benzo[1,4]thiazin-6-yl)-oxazolidin-5-yl]-propyl}-benzamide Starting from 2-amino-5-chlorobenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (158 mg; 73% yield).

MS (ESI, m/z): 461.1 [M+H$^+$].

25.ii. 6-chloro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 25.i and using Procedure B, the title compound was obtained as a beige solid (10 mg; 14% yield).

$^1$H NMR (DMSO-d$_6$) δ: 7.60 (d, J=2.5 Hz, 1H), 7.21-7.34 (m, 3H), 7.07 (dd, J=2.3, 8.5 Hz, 1H), 6.86 (d, J=8.9 Hz, 1H), 4.59-4.78 (m, 1H), 4.06 (t, J=8.6 Hz, 1H), 3.84-3.95 (m, 2H), 3.56-3.65 (m, 1H), 3.41 (s, 2H), 1.50-1.85 (m, 4H).

HR LC-MS: MS (ESI, m/z): 487.0846 [M+H$^+$]; t$_R$=1.49 min.

Example 26

6-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione

26.i. 2-amino-5-fluoro-N-{3-[(R)-2-oxo-3-(3-oxo-3,4-dihydro-2H-benzo[1,4]thiazin-6-yl)-oxazolidin-5-yl]-propyl}-benzamide Starting from 2-amino-5-fluorobenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (160 mg; 70% yield).

MS (ESI, m/z): 445.1 [M+H$^+$].

26.ii. 6-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 26.i and using Procedure B, the title compound was obtained as a grey solid (10 mg; 14% yield).

$^1$H NMR (DMSO-d$_6$) δ: 10.53 (br. s, 1H), 7.60 (dd, J=2.9, 8.7 Hz, 1H), 7.47-7.58 (m, 1H), 7.25-7.36 (m, 2H), 7.19 (dd, J=4.5, 9.0 Hz, 1H), 7.06 (dd, J=2.3, 8.6 Hz, 1H), 4.60-4.76 (m, 1H), 4.06 (t, J=8.7 Hz, 1H), 3.89-3.97 (m, 2H), 3.62 (dd, J=7.2, 8.9 Hz, 1H), 3.41 (s, 2H), 1.60-1.85 (m, 4H).

HR LC-MS: MS (ESI, m/z): 471.1148 [M+H$^+$]; t$_R$=1.37 min.

Example 27

7-chloro-3-{3-[(R)-2-oxo-3-(3-oxo-3,4-dihydro-2H-benzo[1,4]-thiazin-6-yl)-oxazolidin-5-yl]-propyl}-1H-quinazoline-2,4-dione

27.i. 2-amino-4-chloro-N-{3-[(R)-2-oxo-3-(3-oxo-3,4-dihydro-2H-benzo[1,4]thiazin-6-yl)-oxazolidin-5-yl]-propyl}-benzamide Starting from 2-amino-4-chlorobenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (110 mg; 51% yield).

MS (ESI, m/z): 461.1 [M+H⁺].

27.ii. 7-chloro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 27.i and using Procedure B, the title compound was obtained as a beige solid (9 mg; 12% yield).

$^1$H NMR (DMSO-d$_6$) δ: 7.66 (d, J=8.4 Hz, 1H), 7.23-7.37 (m, 2H), 7.02-7.12 (m, 1H), 6.81-6.87 (m, 1H), 6.62-6.73 (m, 1H), 4.60-4.78 (m, 1H), 3.99-4.12 (m, 1H), 3.84-3.96 (m, 2H), 3.55-3.67 (m, 1H), 3.41 (s, 2H), 1.54-1.81 (m, 4H).

HR LC-MS: MS (ESI, m/z): 487.0846 [M+H⁺]; t$_R$=1.47 min.

Example 28

7-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione

28.i. 2-amino-4-fluoro-N-{3-[(R)-2-oxo-3-(3-oxo-3,4-dihydro-2H-benzo[1,4]thiazin-6-yl)-oxazolidin-5-yl]-propyl}-benzamide Starting from 2-amino-4-fluorobenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (130 mg; 78% yield).

MS (ESI, m/z): 445.1 [M+H¹].

28.ii. 7-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 28.i and using Procedure B, the title compound was obtained as a beige solid (32 mg; 45% yield).

$^1$H NMR (DMSO-d$_6$) δ: 10.52 (br. s, 1H), 7.84-7.99 (m, 1H), 7.22-7.39 (m, 2H), 7.02-7.11 (m, 1H), 6.87-6.99 (m, 1H), 6.77-6.86 (m, 1H), 4.61-4.76 (m, 1H), 3.98-4.16 (m, 1H), 3.85-3.96 (m, 2H), 3.56-3.68 (m, 1H), 3.41 (s, 2H), 1.54-1.89 (m, 4H).

HR LC-MS: MS (ESI, m/z): 471.1144 [M+H¹]; t$_R$=1.37 min.

Example 29

8-chloro-3-{3-[(S)-2-oxo-3-(3-oxo-3,4-dihydro-2H-benzo[1,4]-thiazin-6-yl)-oxazolidin-5-yl]-propyl}-1H-quinazoline-2,4-dione

29.i. (S)-2-amino-3-chloro-N-(3-(2-oxo-3-(3-oxo-3,4-dihydro-2H-benzo[b][1,4]thiazin-6-yl)oxazolidin-5-yl)propyl)benzamide Starting from 2-amino-3-chlorobenzoic acid and the compound of Preparation A and using Procedure D, the title compound was obtained as a yellowish solid (100 mg; 74% yield).

MS (ESI, m/z): 461.1 [M+H¹].

29.ii. 8-chloro-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 30.i. and using procedure B, the title compound was obtained as a colourless solid (37 mg; 70% yield).

$^1$H NMR (DMSO-d$_6$) δ: 10.51 (br. s, 1H), 7.57-7.68 (m, 1H), 7.20-7.43 (m, 3H), 7.00-7.13 (m, 1H), 6.59 (t, J=7.6 Hz, 1H), 4.60-4.76 (m, 1H), 3.98-4.15 (m, 1H), 3.85-3.97 (m, 2H), 3.56-3.66 (m, 1H), 3.41 (s, 2H), 1.46-1.92 (m, 4H).

MS (ESI, m/z): 487.084 [M+H⁺]; t$_R$=1.44 min.

Example 30

8-chloro-1-methyl-3-(2-{2-[(R)-2-oxo-3-(3-oxo-3,4-dihydro-2H-benzo[1,4]thiazin-6-yl)-oxazolidin-5-yl]-ethylamino}-ethyl)-1H-quinazoline-2,4-dione Starting from 6-[(5R)-5-(2-aminoethyl)-2-oxo-3-oxazolidinyl]-2H-1,4-benzothiazin-3(4H)-one (prepared according to WO 2009/104147) and the compound of Preparation Q and using Procedure G, the title compound was obtained as a colourless solid (53 mg; 31% yield).

$^1$H NMR (DMSO-d$_6$) δ: 10.53 (br. s, 1H), 8.01 (dd, J=1.6, 7.8 Hz, 1H), 7.80 (dd, J=1.6, 7.9 Hz, 1H), 7.22-7.35 (m, 3H), 7.04 (dd, J=2.3, 8.5 Hz, 1H), 4.61-4.75 (m, 1H), 3.95-4.08 (m, 3H), 3.60-3.71 (m, 4H), 3.41 (s, 2H), 2.57-2.80 (m, 4H), 1.70-1.82 (m, 2H).

HR LC-MS: MS (ESI, m/z): 530.1275 [M+H⁺]; t$_R$=1.04 min.

Example 31

8-chloro-1-methyl-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione The compound of Preparation A and 8-chloro-1-methyl-1H-benzo[d][1,3]oxazine-2,4-dione were reacted using Procedure A. After stirring for 2 h at 50° C., the reaction was treated with two equivalents of triphosgene and further stirred at 60° C. for 7 h. The reaction mixture was further processed as described in Procedure B, affording a pink solid (27 mg; 28% yield).

$^1$H NMR (DMSO-d$_6$) δ: 10.50 (br. s, 1H), 7.99-8.06 (m, 1H), 7.79-7.87 (m, 1H), 7.24-7.36 (m, 3H), 7.03-7.11 (m, 1H), 4.61-4.76 (m, 1H), 4.01-4.11 (m, 1H), 3.91-4.01 (m, 2H), 3.68 (s, 3H), 3.56-3.67 (m, 1H), 3.41 (s, 2H), 1.62-1.86 (m, 4H).

HR LC-MS: MS (ESI, m/z): 501.1005 [M+H$^+$]; $t_R$=1.64 min.

Example 32

8-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione 32.i. 2-amino-3-fluoro-N-{3-[(R)-2-oxo-3-(3-oxo-3,4-dihydro-2H-benzo[1,4]thiazin-6-yl)-oxazolidin-5-yl]-propyl}-benzamide Starting from 2-amino-3-fluorobenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (80 mg; 56% yield).
MS (ESI, m/z): 445.2 [M+H$^+$].

32.ii. 8-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 32.i and using Procedure B, the title compound was obtained as a beige solid (43 mg; 58% yield).
$^1$H NMR (DMSO-d$_6$) δ: 10.52 (br. s, 1H), 7.54-7.63 (m, 1H), 7.18-7.42 (m, 3H), 7.02-7.12 (m, 1H), 6.72-6.86 (m, 1H), 4.59-4.80 (m, 1H), 4.00-4.14 (m, 1H), 3.87-3.98 (m, 2H), 3.56-3.68 (m, 1H), 3.40 (s, 2H), 1.53-1.88 (m, 4H).
HR LC-MS: MS (ESI, m/z): 471.1131 [M+H$^+$]; $t_R$=1.34 min.

Example 33

5-methoxy-3-{3-[(R)-2-oxo-3-(3-oxo-3,4-dihydro-2H-benzo[1,4]-thiazin-6-yl)-oxazolidin-5-yl]-propyl}-1H-quinazoline-2,4-dione 33.i. 2-amino-6-methoxy-N-{3-[(R)-2-oxo-3-(3-oxo-3,4-dihydro-2H-benzo[1,4]thiazin-6-yl)-oxazolidin-5-yl]-propyl}-benzamide Starting from 2-amino-6-methoxybenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (170 mg; 78% yield).
MS (ESI, m/z): 457.4 [M+H$^+$].

33.ii. 5-methoxy-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 33.i and using Procedure B, the title compound was obtained as a beige solid (50 mg; 69% yield).
$^1$H NMR (DMSO-d$_6$) δ: 11.23 (br. s, 1H), 10.52 (br. s, 1H), 7.51 (t, J=8.3 Hz, 1H), 7.31 (m, 2H), 7.00-7.11 (m, 1H), 6.65-6.77 (m, 2H), 4.60-4.76 (m, 1H), 4.00-4.13 (m, 1H), 3.82-3.92 (m, 2H), 3.81 (s, 3H), 3.57-3.67 (m, 1H), 3.41 (s, 2H), 1.45-1.90 (m, 4H).
HR LC-MS: MS (ESI, m/z): 483.1349 [M+H$^+$]; $t_R$=1.21 min.

Example 34

6-methoxy-3-{3-[(R)-2-oxo-3-(3-oxo-3,4-dihydro-2H-benzo[1,4]-thiazin-6-yl)-oxazolidin-5-yl]-propyl}-1H-quinazoline-2,4-dione 34.i. 2-amino-5-methoxy-N-{3-[(R)-2-oxo-3-(3-oxo-3,4-dihydro-2H-benzo[1,4]thiazin-6-yl)-oxazolidin-5-yl]-propyl}-benzamide Starting from 2-amino-5-methoxybenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (180 mg; 82% yield).
MS (ESI, m/z): 457.4 [M+H$^+$].

34.ii. 6-methoxy-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 34.i and using Procedure B, the title compound was obtained as a beige solid (43 mg; 59% yield).
$^1$H NMR (DMSO-d$_6$) δ: 7.24-7.36 (m, 3H), 7.15 (dd, J=3.0, 8.9 Hz, 1H), 7.07 (dd, J=2.3, 8.6 Hz, 1H), 7.01 (m, 1H), 4.59-4.77 (m, 1H), 4.06 (t, J=8.6 Hz, 1H), 3.89-3.98 (m, 2H), 3.74 (s, 3H), 3.57-3.67 (m, 1H), 3.41 (s, 2H), 1.56-1.85 (m, 4H).
HR LC-MS: MS (ESI, m/z): 483.1348 [M+H$^+$]; $t_R$=1.34 min.

Example 35

7-methoxy-3-{3-[(S)-2-oxo-3-(3-oxo-3,4-dihydro-2H-benzo[1,4]-thiazin-6-yl)-oxazolidin-5-yl]-propyl}-1H-quinazoline-2,4-dione 35.i. (S)-7-methoxy-3-(3-(2-oxo-3-(3-oxo-3,4-dihydro-2H-benzo[b][1,4]thiazin-6-yl)oxazolidin-5-yl)propyl)quinazoline-2,4(1H,3H)-dione Starting from 2-amino-4-methoxybenzoic acid and the product of Preparation A and using Procedure D, the title compound was obtained as a beige solid (75 mg; 50% yield).
MS (ESI, m/z): 457.4 [M+H$^+$].

35.ii. 7-methoxy-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 35.i and using Procedure B, the title compound was obtained as a beige solid (33 mg; 42% yield).
$^1$H NMR (DMSO-d$_6$) δ: 11.29 (br. s, 1H), 10.52 (br. s, 1H), 7.83 (d, J=8.8 Hz, 1H), 7.24-7.36 (m, 2H), 7.01-7.11 (m, 1H), 6.73-6.81 (m, 1H), 6.59-6.63 (m, 1H), 4.58-4.75 (m, 1H), 4.01-4.14 (m, 1H), 3.85-3.95 (m, 2H), 3.80 (s, 3H), 3.56-3.68 (m, 1H), 3.55 (s, 2H), 1.58-1.84 (m, 4H).
HR LC-MS: MS (ESI, m/z): 483.1338 [M+H$^+$]; $t_R$=1.35 min.

Example 36

8-methoxy-3-{3-[(R)-2-oxo-3-(3-oxo-3,4-dihydro-2H-benzo[1,4]-thiazin-6-yl)-oxazolidin-5-yl]-propyl}-1H-quinazoline-2,4-dione

36.i. 2-amino-3-methoxy-N-{3-[(R)-2-oxo-3-(3-oxo-3,4-dihydro-2H-benzo[1,4]thiazin-6-yl)-oxazolidin-5-yl]-propyl}-benzamide Starting from 2-amino-3-methoxybenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (179 mg; 82% yield).

MS (ESI, m/z): 457.4 [M+H$^+$].

36.ii. 8-methoxy-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 36.i. and using procedure B, the title compound was obtained as a beige solid (73 mg; 100% yield).

$^1$H NMR (DMSO-d$_6$) δ: 7.21-7.43 (m, 3H), 6.95-7.11 (m, 2H), 6.76-6.88 (m, 1H), 4.59-4.77 (m, 1H), 3.99-4.12 (m, 1H), 3.84-3.99 (m, 2H), 3.78 (s, 3H), 3.55-3.66 (m, 1H), 3.41 (s, 2H), 1.51-1.89 (m, 4H).

HR LC-MS: MS (ESI, m/z): 483.1338 [M+H$^+$]; $t_R$=1.37 min.

Example 37

3-{3-[(S)-2-oxo-3-(3-oxo-3,4-dihydro-2H-benzo[1,4]-thiazin-6-yl)-oxazolidin-5-yl]-propyl}-6-pyrrolidin-1-yl-1H-quinazoline-2,4-dione

37.i. (S)-2-amino-N-(3-(2-oxo-3-(3-oxo-3,4-dihydro-2H-benzo[b][1,4]thiazin-6-yl)oxazolidin-5-yl)propyl)-5-(pyrrolidin-1-yl)benzamide Starting from 2-amino-5-pyrrolidin-1-yl-benzoic acid and the compound of Preparation A and using Procedure D, the title compound was obtained as a brown foam (56 mg; 33% yield).

MS (ESI, m/z): 496.2 [M+H$^+$].

37.ii. 3-{3-[(S)-2-oxo-3-(3-oxo-3,4-dihydro-2H-benzo[1,4]thiazin-6-yl)-oxazolidin-5-yl]-propyl}-6-pyrrolidin-1-yl-1H-quinazoline-2,4-dione Starting from intermediate 37.i and using Procedure B, the title compound was obtained as a beige solid (21 mg; 36% yield).

$^1$H NMR (DMSO-d$_6$) δ: 11.06 (br. s, 1H), 10.52 (br. s, 1H), 7.25-7.35 (m, 2H), 6.95-7.10 (m, 3H), 6.92 (d, J=2.6 Hz, 1H), 4.60-4.76 (m, 1H), 4.00-4.11 (m, 1H), 3.89-3.99 (m, 2H), 3.62 (dd, J=7.2, 8.9 Hz, 1H), 3.41 (s, 2H), 3.17-3.25 (m, 4H), 1.89-2.01 (m, 4H), 1.61-1.83 (m, 4H).

HR LC-MS: MS (ESI, m/z): 522.1803 [M+H$^+$]; $t_R$=1.56 min.

Example 38

6,7-difluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione

38.i. (R)-6,7-difluoro-3-(3-(2-oxo-3-(3-oxo-3,4-dihydro-2H-benzo[b][1,4]thiazin-6-yl)oxazolidin-5-yl)propyl)quinazoline-2,4 (1H, 3H)-dione Starting from 2-amino-4,5-difluorobenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (76 mg; 57% yield).

MS (ESI, m/z): 463.2 [M+H$^+$].

38.ii. 6,7-difluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 38.i and using Procedure B, the title compound was obtained as a brown solid (23 mg; 31% yield).

$^1$H NMR (DMSO-d$_6$) δ: 11.50 (br. s, 1H), 10.50 (br. s, 1H), 7.79-7.97 (m, 1H), 7.22-7.40 (m, 3H), 7.00-7.17 (m, 1H), 4.59-4.77 (m, 1H), 4.00-4.15 (m, 1H), 3.84-3.99 (m, 2H), 3.55-3.68 (m, 1H), 3.41 (s, 2H), 1.53-1.92 (m, 4H).

HR LC-MS: MS (ESI, m/z): 489.1051 [M+H$^+$]; $t_R$=1.44 min.

Example 39

6,7-dimethoxy-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione

39.i. (R)-6,7-dimethoxy-3-(3-(2-oxo-3-(3-oxo-3,4-dihydro-2H-benzo[b][1,4]thiazin-6-yl)oxazolidin-5-yl)propyl)quinazoline-2,4 (1H, 3H)-dione Starting from 2-amino-4,5-dimethoxybenzoic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a brown solid (123 mg; 87% yield).

MS (ESI, m/z): 487.4 [M+H$^+$].

39.ii. 6,7-dimethoxy-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 39.i and using Procedure B, the title compound was obtained as a brown solid (45 mg; 43% yield).

$^1$H NMR (DMSO-d$_6$) δ: 11.20 (br. s, 1H), 10.53 (br. s, 1H), 7.20-7.43 (m, 3H), 6.98-7.13 (m, 1H), 6.60-6.73 (m, 1H), 4.57-4.82 (m, 1H), 3.99-4.17 (m, 1H), 3.87-3.98 (m, 1H), 3.81 (s, 3H), 3.77 (s, 3H), 3.68-3.78 (m, 1H), 3.56-3.68 (m, 1H), 3.41 (s, 2H), 1.47-1.97 (m, 4H).

HR LC-MS: MS (ESI, m/z): 513.1445 [M+H$^+$]; $t_R$=1.28 min.

Example 40

5,8-dichloro-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione

40.i. (S)-2-amino-3,6-dichloro-N-(3-(2-oxo-3-(3-oxo-3,4-dihydro-2H-benzo[b][1,4]thiazin-6-yl)oxazolidin-5-yl)propyl)benzamide Starting from the compound of Preparation A and 5,8-dichloroquinazoline-2,4(1H,3H)-dione and using Procedure A, the title compound was obtained as a yellow oil (90 mg; 42% yield).
$^1$H NMR (DMSO-$d_6$) δ: 10.54 (br. s, 1H), 8.57 (t, 1H), 7.34 (d, J=2.3 Hz, 1H), 7.30 (d, J=8.5 Hz, 1H), 7.24 (d, J=8.5 Hz, 1H), 7.08 (dd, J=2.4, 8.6 Hz, 1H), 6.65 (d, J=8.6 Hz, 1H), 5.26 (br. s, 2H), 4.63-4.75 (m, 1H), 4.06-4.14 (m, 1H), 3.58-3.68 (m, 1H), 3.41 (s, 2H), 3.15 (d, J=5.2 Hz, 2H), 1.71-1.87 (m, 2H), 1.54-1.71 (m, 2H).

40.ii. 5,8-dichloro-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione Starting from intermediate 40.i and using Procedure B, the title compound was obtained as a beige solid (70 mg; 74% yield).
$^1$H NMR (DMSO-$d_6$) δ: 10.85 (br. s, 1H), 10.53 (br. s, 1H), 7.73 (d, J=8.5 Hz, 1H), 7.32 (d, J=2.4 Hz, 1H), 7.26-7.30 (m, 1H), 7.25 (d, J=8.6 Hz, 1H), 7.04-7.10 (m, 1H), 4.59-4.79 (m, 1H), 4.01-4.12 (m, 1H), 3.87-3.96 (m, 2H), 3.58-3.68 (m, 1H), 3.41 (s, 2H), 1.59-1.89 (m, 4H).
HR LC-MS: MS (ESI, m/z): 521.0449 [M+H$^+$]; $t_R$=1.53 min.

Example 41

2-{3-[(R)-2-oxo-3-(3-oxo-3,4-dihydro-2H-benzo[1,4]thiazin-6-yl)-oxazolidin-5-yl]-propyl}-6,7-dihydro-5H-pyrido[3,2,1-ij]quinazoline-1,3-dione

41.i. (R)—N-(3-(2-oxo-3-(3-oxo-3,4-dihydro-2H-benzo[b][1,4]thiazin-6-yl)oxazolidin-5-yl)propyl)-1,2,3,4-tetrahydroquinoline-8-carboxamide Starting from 1,2,3,4-tetrahydroquinoline-8-carboxylic acid and 6-[(R)-5-(3-amino-propyl)-2-oxo-oxazolidin-3-yl]-4H-benzo[1,4]thiazin-3-one (described in WO 2010/041219) and using Procedure D, the title compound was obtained as a beige solid (114 mg; 85% yield).
MS (ESI, m/z): 467.3 [M+H$^+$].

41.ii. 2-{3-[(R)-2-oxo-3-(3-oxo-3,4-dihydro-2H-benzo[1,4]thiazin-6-yl)-oxazolidin-5-yl]-propyl}-6,7-dihydro-5H-pyrido[3,2,1-ij]quinazoline-1,3-dione Starting from intermediate 41.i and using Procedure B, the title compound was obtained as a brown solid (32 mg; 30% yield).
$^1$H NMR (DMSO-$d_6$) δ: 10.54 (br. s, 1H), 7.72-7.81 (m, 1H), 7.24-7.40 (m, 3H), 7.00-7.11 (m, 2H), 4.56-4.83 (m, 1H), 4.01-4.17 (m, 1H), 3.76-3.86 (m, 2H), 3.60-3.72 (m, 1H), 3.44-3.53 (m, 2H), 3.41 (s, 2H), 2.74-2.82 (m, 2H), 1.58-2.02 (m, 6H).
HR LC-MS: MS (ESI, m/z): 493.1551 [M+H$^+$]; $t_R$=1.51 min.

Example 42

3-{3-[(S)-2-oxo-3-(3-oxo-3,4-dihydro-2H-benzo[1,4]-thiazin-6-yl)-oxazolidin-5-yl]-propyl}-1H-benzo[g]quinazoline-2,4-dione

42.i. 3-amino-naphthalene-2-carboxylic acid {3-[(S)-2-oxo-3-(3-oxo-3,4-dihydro-2H-benzo[1,4]thiazin-6-yl)-oxazolidin-5-yl]-propyl}-amide Starting from 3-amino-2-naphthoic acid and the compound of Preparation A and using Procedure D, the title compound was obtained as a beige solid (100 mg; 56% yield).
MS (ESI, m/z): 477.0 [M+H$^+$].

42.ii. 3-{3-[(S)-2-oxo-3-(3-oxo-3,4-dihydro-2H-benzo[1,4]thiazin-6-yl)-oxazolidin-5-yl]-propyl}-1H-benzo[g]quinazoline-2,4-dione Starting from intermediate 42.i and using Procedure B, the title compound was obtained as a brown solid (7 mg; 9% yield).
$^1$H NMR (DMSO-$d_6$) δ: 11.50 (br s, 1H), 10.55 (br. s, 1H), 8.70 (s, 1H), 8.12 (d, J=8.4 Hz, 1H), 7.92 (d, J=8.4 Hz, 1H), 7.57-7.65 (m, 1H), 7.55 (s, 1H), 7.43-7.50 (m, 1H), 7.35 (d, J=2.3 Hz, 1H), 7.31 (d, J=8.5 Hz, 1H), 7.09 (dd, J=2.3, 8.6 Hz, 1H), 4.68-4.79 (m, 1H), 4.06-4.14 (m, 1H), 3.98-4.06 (m, 2H), 3.67 (dd, J=7.4, 8.6 Hz, 1H), 3.44 (s, 2H), 1.66-1.91 (m, 4H).
HR LC-MS: MS (ESI, m/z): 503.1388 [M+H$^+$]; $t_R$=1.55 min.

Example 43

1-cyclopropyl-6,7-difluoro-8-methoxy-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione Starting from 1-cyclopropyl-6,7-difluoro-8-methoxy-1H-quinazoline-2,4-dione (described in *Org. Process Res. Dev.* (2007), 11(3), 441-449) and 6-[(5S)-5-[3-[(methylsulfonyl)oxy]propyl]-2-oxo-3-oxazolidinyl]-2H-1,4-benzothiazin-3(4H)-one (prepared according to WO 2010/041194) and using Procedure E, the title compound was obtained as a colourless solid (140 mg; 65% yield).
$^1$H NMR (DMSO-$d_6$) δ: 10.53 (br. s, 1H), 7.67 (dd, J=8.4, 9.9 Hz, 1H), 7.25-7.33 (m, 2H), 7.07 (dd, J=2.4, 8.6 Hz, 1H), 4.60-4.75 (m, 1H), 4.00-4.11 (m, 1H), 3.84-3.95 (m, 6H), 3.3.56-3.65 (m, 1H), 3.41 (s, 2H), 1.57-1.81 (m, 4H), 0.94-1.04 (m, 2H), 0.58-0.68 (m, 2H).
HR LC-MS: MS (ESI, m/z): 559.1464 [M+H$^+$]; $t_R$=1.73 min.

Example 44

2-{3-[(S)-2-oxo-3-(3-oxo-3,4-dihydro-2H-benzo[1,4]thiazin-6-yl)-oxazolidin-5-yl]-propyl}-6,7-dihydro-5H-pyrido[3,2,1-ij]quinazoline-1,3-dione Starting from 6,7-dihydropyrido[3,2,1-ij]quinazoline-1,3(2H,5H)-dione (prepared according to WO 01/79206) and 6-[(5S)-5-[3-[(methylsulfonyl)oxy]propyl]-2-oxo-3-oxazolidinyl]-2H-1,4-benzothiazin-3(4H)-one (prepared according to WO 2010/041194) and using Procedure E, the title compound was obtained as a colourless solid (48 mg; 25% yield).

$^1$H NMR (DMSO-d$_6$) δ: 10.52 (br. s, 1H), 7.85 (dd, J=1.4, 7.8 Hz, 1H), 7.51 (dd, J=0.5, 7.4 Hz, 1H), 7.24-7.34 (m, 2H), 7.12-7.19 (m, 1H), 7.07 (dd, J=2.3, 8.5 Hz, 1H), 4.60-4.77 (m, 1H), 4.06 (t, J=8.8 Hz, 1H), 3.89-4.02 (m, 4H), 3.63 (dd, J=7.1, 8.6 Hz, 1H), 3.41 (s, 2H), 2.81-2.91 (m, 2H), 1.90-2.04 (m, 2H), 1.62-1.82 (m, 4H).

HR LC-MS: MS (ESI, m/z): 493.1545 [M+H$^+$]; t$_R$=1.55 min.

Example 45

2-{3-[(S)-2-oxo-3-(3-oxo-3,4-dihydro-2H-pyrido[3,2-b][1,4]oxazin-6-yl)-oxazolidin-5-yl]-propyl}-6,7-dihydro-5H-pyrido[3,2,1-ij]quinazoline-1,3-dione Starting from 6,7-dihydropyrido[3,2,1-ij]quinazoline-1,3 (2H,5H)-dione (prepared according to WO 01/79206) and intermediate D.i and using Procedure E, the title compound was obtained as a light blue solid (21 mg; 11% yield).

$^1$H NMR (DMSO-d$_6$) δ: 7.82-7.88 (m, 1H), 7.56 (d, J=8.7 Hz, 1H), 7.48-7.53 (m, 1H), 7.37-7.41 (m, 1H), 7.16 (t, J=7.7 Hz, 1H), 4.65-4.73 (m, 1H), 4.58 (s, 2H), 4.12-4.22 (m, 1H), 3.89-4.03 (m, 4H), 3.62-3.74 (m, 1H), 2.82-2.92 (m, 2H), 1.88-2.04 (m, 2H), 1.62-1.87 (m, 4H).

HR LC-MS: MS (ESI, m/z): 478.1731 [M+H$^+$]; t$_R$=1.48 min.

Example 46

7-bromo-1-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione Starting from the compound of Preparation E and 6-[(5R)-5-[3-[(methylsulfonyl)oxy]propyl]-2-oxo-3-oxazolidinyl]-2H-1,4-benzothiazin-3(4H)-one (prepared according to WO 2010/041219) and using Procedure E, the title compound was obtained as a colourless solid (152 mg; 17% yield).

$^1$H NMR (DMSO-d$_6$) δ: 10.53 (br. s, 1H), 7.94 (d, J=8.4 Hz, 1H), 7.67 (d, J=1.7 Hz, 1H), 7.46 (dd, J=1.7, 8.4 Hz, 1H), 7.25-7.33 (m, 2H), 7.06 (dd, J=2.4, 8.6 Hz, 1H), 4.61-4.75 (m, 1H), 4.06 (t, J=8.6 Hz, 1H), 3.93-4.02 (m, 2H), 3.62 (dd, J=7.3, 8.9 Hz, 1H), 3.49 (s, 3H), 3.41 (s, 2H), 1.61-1.84 (m, 4H).

HR LC-MS: MS (ESI, m/z): 545.051 [M+H$^+$]; t$_R$=1.66 min.

Example 47

1-methyl-3-{3-[(R)-2-oxo-3-(3-oxo-3,4-dihydro-2H-benzo[1,4]-thiazin-6-yl)-oxazolidin-5-yl]-propyl}-7-vinyl-1H-quinazoline-2,4-dione A suspension of the compound of Example 46 (0.33 mmol), tetrakis(triphenylphosphine)palladium(0) complex (0.016 mmol), vinylboronic anhydride pyridine complex (0.165 mmol) and K$_2$CO$_3$ (0.33 mmol) in dioxane (2.5 ml) and water (0.8 ml) was purged with argon. The reaction mixture was stirred at 100° C. overnight. The reaction mixture was allowed cooling to rt and was diluted with water and EA. The org. layer was separated and the aq. layer was extracted with EA. The combined org. layers were washed with brine and dried over MgSO$_4$, filtered and concentrated under reduced pressure. The resulting material was sequentially crystallized from TBME/MeOH, EA/MeOH and finally DCM, affording the title compound as colourless crystals in quantitative yield.

$^1$H NMR (DMSO-d$_6$) δ: 10.55 (s, 1H), 8.00 (d, J=8.1 Hz, 1H), 7.41-7.50 (m, 2H), 7.25-7.36 (m, 2H), 7.05-7.12 (m, 1H), 6.88 (dd, J=11.0, 17.7 Hz, 1H), 6.13 (d, J=17.9 Hz, 1H), 5.47-5.54 (m, 1H), 4.59-4.80 (m, 1H), 4.02-4.11 (m, 1H), 3.95-4.02 (m, 2H), 3.58-3.67 (m, 1H), 3.54 (s, 3H), 3.42 (s, 2H), 1.61-1.86 (m, 4H).

HR LC-MS: MS (ESI, m/z): 493.1547 [M+H$^+$]; t$_R$=1.61 min.

Example 48 rac-3-{4-[2-oxo-3-(3-oxo-3,4-dihydro-2H-benzo[1,4]thiazin-6-yl)-oxazolidin-5-yl]-butyl}-1H-quinazoline-2,4-dione 48.i. rac-2-amino-N-{4-[2-oxo-3-(3-oxo-3,4-dihydro-2H-benzo[1,4]thiazin-6-yl)-oxazolidin-5-yl]-butyl}-benzamide Starting from the compound of Preparation F and isatoic anhydride and using Procedure A, the title compound was obtained as a yellowish foam (490 mg; 89% yield).

MS (ESI, m/z): 441.4 [M+H$^+$].

48.ii. rac-3-{4-[2-oxo-3-(3-oxo-3,4-dihydro-2H-benzo[1,4]thiazin-6yl)-oxazolidin-5-yl]-butyl}-1H-quinazoline-2,4-dione Starting from intermediate 48.i and using Procedure B, the title compound was obtained as a beige solid (80 mg; 75% yield).

$^1$H NMR (DMSO-d$_6$) δ: 11.39 (br. s, 1H), 10.53 (br. s, 1H), 7.91 (dd, J=1.3, 7.8 Hz, 1H), 7.59-7.67 (m, 1H), 7.34 (d, J=2.3 Hz, 1H), 7.28 (d, J=8.5 Hz, 1H), 7.11-7.24 (m, 2H), 7.06 (dd, J=2.3, 8.6 Hz, 1H), 4.57-4.72 (m, 1H), 4.06 (t, J=8.7 Hz, 1H), 3.90 (t, J=7.0 Hz, 2H), 3.64 (dd, J=7.2, 8.7 Hz, 1H), 3.41 (s, 2H), 1.69-1.81 (m, 2H), 1.56-1.69 (m, 2H), 1.33-1.48 (m, 2H).

HR LC-MS: MS (ESI, m/z): 467.1392 [M+H$^+$]; t$_R$=1.38 min.

Example 49

3-{(RS)-2-hydroxy-4-[(RS)-2-oxo-3-(3-oxo-3,4-dihydro-2H-benzo[1,4]oxazin-6-yl)-oxazolidin-5-yl]-butyl}-1-methyl-1H-quinazoline-2,4-dione Starting from 1-methylquinazoline-2,4(1H,3H)-dione and the compound of Preparation G and using Procedure E, the title compound was obtained as a beige solid (60 mg; 44% yield).

$^1$H NMR (DMSO-d$_6$) δ: 10.70 (br. s, 1H), 8.04 (dt, J=1.6, 8.0 Hz, 1H), 7.71-7.81 (m, 1H), 7.43 (d, J=8.5 Hz, 1H), 7.24-7.34 (m, 2H), 6.85-6.96 (m, 2H), 4.76-4.83 (m, 1H), 4.55-4.71 (m, 1H), 4.52 (s, 2H), 3.96-4.12 (m, 2H), 3.76-3.92 (m, 2H), 3.57-3.70 (m, 1H), 3.50 (s, 3H), 1.24-1.95 (m, 4H).

HR LC-MS: MS (ESI, m/z): 481.1718 [M+H$^+$]; t$_R$=1.22 min.

Example 50

3-{(RS)-2-hydroxy-4-[(R)-2-oxo-3-(3-oxo-3,4-dihydro-2H-pyrido[3,2-b][1,4]thiazin-6-yl)-oxazolidin-5-yl]-butyl}-1-methyl-1H-quinazoline-2,4-dione Starting from 1-methylquinazoline-2,4(1H,3H)-dione and the compound of Preparation H and using Procedure E, the title compound was obtained as a beige solid (21 mg; 15% yield).

$^1$H NMR (DMSO-d$_6$) δ: 10.84 (br. s, 1H), 7.98-8.07 (m, 1H), 7.70-7.82 (m, 2H), 7.61-7.70 (m, 1H), 7.43 (d, J=8.5 Hz, 1H), 7.24-7.32 (m, 1H), 4.80-4.88 (m, 1H), 4.59-4.75 (m, 1H), 4.12-4.26 (m, 1H), 4.01-4.10 (m, 1H), 3.76-3.91 (m, 2H), 3.65-3.76 (m, 1H), 3.50 (s, 5H), 1.24-1.94 (m, 4H).

HR LC-MS: MS (ESI, m/z): 498.1451 [M+H$^+$]; t$_R$=1.33 min.

Example 51

1-methyl-3-{4-[(R)-2-oxo-3-(3-oxo-3,4-dihydro-2H-pyrido[3,2-b][1,4]thiazin-6-yl)-oxazolidin-5-yl]-butyl}-1H-quinazoline-2,4-dione Starting from 1-methylquinazoline-2,4(1H,3H)-dione and the compound of Preparation I and using Procedure E, the title compound was obtained as a colourless solid (25 mg; 3% yield).

$^1$H NMR (DMSO-d$_6$) δ: 10.83 (br. s, 1H), 7.98-8.09 (m, 1H), 7.71-7.82 (m, 2H), 7.60-7.71 (m, 1H), 7.37-7.49 (m, 1H), 7.21-7.35 (m, 1H), 4.57-4.77 (m, 1H), 4.11-4.26 (m, 1H), 3.88-4.03 (m, 2H), 3.61-3.79 (m, 1H), 3.51 (s, 5H), 1.53-1.89 (m, 4H), 1.24-1.53 (m, 2H).

HR LC-MS: MS (ESI, m/z): 482.1503 [M+H$^+$]; t$_R$=1.54 min.

Example 52

1-methyl-3-{4-[(R)-2-oxo-3-(3-oxo-3,4-dihydro-2H-pyrido[3,2-b][1,4]oxazin-6-yl)-oxazolidin-5-yl]-butyl}-1H-quinazoline-2,4-dione Starting from 1-methylquinazoline-2,4(1H,3H)-dione and the compound of Preparation J and using Procedure E, the title compound was obtained as a colourless solid (32 mg; 13% yield).

$^1$H NMR (DMSO-d$_6$) δ: 11.15 (br. s, 1H), 8.04 (dd, J=1.5, 7.9 Hz, 1H), 7.72-7.80 (m, 1H), 7.53-7.58 (m, 1H), 7.36-7.47 (m, 2H), 7.24-7.32 (m, 1H), 4.60-4.72 (m, 1H), 4.58 (s, 2H), 4.12-4.22 (m, 1H), 3.96 (t, J=7.2 Hz, 2H), 3.69 (dd, J=7.0, 10.1 Hz, 1H), 3.50 (s, 3H), 1.56-1.82 (m, 4H), 1.28-1.50 (m, 2H).

HR LC-MS: MS (ESI, m/z): 466.1729 [M+H$^+$]; t$_R$=1.44 min.

Example 53

3-(2-{[(R)-2-oxo-3-(3-oxo-3,4-dihydro-2H-pyrido[3,2-b][1,4]thiazin-6-yl)-oxazolidin-5-ylmethyl]-amino}-ethyl)-1H-quinazoline-2,4-dione Starting from 3-(2-aminoethyl)-2,4(1H,3H)-quinazolinedione (prepared according to *J. Med. Chem.* (1992), 35(26), 4903-10) and methanesulfonic acid (S)-2-oxo-3-(3-oxo-3,4-dihydro-2H-pyrido[3,2-b][1,4]thiazin-6-yl)-oxazolidin-5-ylmethyl ester (prepared in analogy to its (R)-enantiomer, described in WO 2010/041194) and using Procedure F, the title compound was obtained as a yellow solid (21 mg; 18% yield).

$^1$H NMR (DMSO-d$_6$) δ: 11.34 (br. s, 1H), 10.79 (br. s, 1H), 7.89 (d, J=7.6 Hz, 1H), 7.55-7.78 (m, 3H), 7.07-7.21 (m, 2H), 4.61-4.76 (m, 1H), 4.09 (t, J=9.6 Hz, 1H), 3.89-4.01 (m, 2H), 3.77-3.89 (m, 1H), 3.50 (s, 2H), 2.83-2.92 (m, 2H), 2.73-2.83 (m, 2H).

HR LC-MS: MS (ESI, m/z): 469.1302 [M+H$^+$]; t$_R$=0.87 min.

Example 54

3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione Starting from 3-(2-aminoethyl)-2,4(1H,3H)-quinazolinedione (prepared according to *J. Med. Chem.* (1992), 35(26), 4903-10) and 6-((S)-5-iodomethyl-2-oxooxazolidin-3-yl)-4H-benzo[1,4]thiazin-3-one (prepared according to WO 2008/126034) and using Procedure F, the title compound was obtained as a yellow solid (23 mg; 19% yield).

$^1$H NMR (DMSO-d$_6$) δ: 11.36 (br. s, 1H), 10.52 (br. s, 1H), 7.89 (d, J=7.9 Hz, 1H), 7.56-7.67 (m, 1H), 7.31 (d, J=1.6 Hz, 1H), 7.26 (d, J=8.5 Hz, 1H), 7.10-7.20 (m, 2H), 6.99-7.06 (m, 1H), 4.59-4.75 (m, 1H), 3.89-4.08 (m, 3H), 3.68-3.78 (m, 1H), 3.41 (s, 2H), 2.86 (d, J=5.0 Hz, 2H), 2.75-2.83 (m, 2H).

HR LC-MS: MS (ESI, m/z): 468.1343 [M+H$^+$]; t$_R$=0.85 min.

Example 55

1-methyl-3-(2-{[(R)-2-oxo-3-(3-oxo-3,4-dihydro-2H-pyrido[3,2-b][1,4]thiazin-6-yl)-oxazolidin-5-ylmethyl]-amino}-ethyl)-1H-quinazoline-2,4-dione formate salt Starting from the compound of Preparation K and methanesulfonic acid (S)-2-oxo-3-(3-oxo-3,4-dihydro-2H-pyrido[3,2-b][1,4]thiazin-6-yl)-oxazolidin-5-ylmethyl ester (prepared in analogy to its (R)-enantiomer, described in WO 2010/041194) and using Procedure F, the title salt was obtained as a yellow foam after purification by HPLC (38 mg; 16% yield).

HR LC-MS: MS (ESI, m/z): 483.1455 [M+H$^+$]; t$_R$=0.93 min.

Example 56

1-methyl-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione Starting from 6-((R)-5-aminomethyl-2-oxo-oxazolidin-3-yl)-4H-benzo[1,4]thiazin-3-one (prepared according to WO 2008/126024) and the compound of Preparation L and using Procedure G, the title compound was obtained as a colourless solid (66 mg; 60% yield).

$^1$H NMR (DMSO-d$_6$) δ: 10.52 (br. s, 1H), 8.01 (dd, J=1.6, 7.8 Hz, 1H), 7.70-7.77 (m, 1H), 7.40 (d, J=8.4 Hz, 1H), 7.22-7.32 (m, 3H), 7.02 (dd, J=2.4, 8.6 Hz, 1H), 4.59-4.72 (m, 1H), 3.91-4.11 (m, 3H), 3.72 (dd, J=6.6, 8.7 Hz, 1H), 3.47 (s, 3H), 3.41 (s, 2H), 2.76-2.89 (m, 4H).

HR LC-MS: MS (ESI, m/z): 482.1502 [M+H$^+$]; t$_R$=0.91 min.

Example 57

1,5-dimethyl-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione Starting from 6-((R)-5-aminomethyl-2-oxo-oxazolidin-3-yl)-4H-benzo[1,4]thiazin-3-one (prepared according to WO 2008/126024) and the compound of Preparation M and using Procedure G, the title compound was obtained as a colourless solid (62 mg; 42% yield).

$^1$H NMR (DMSO-d$_6$) δ: 10.51 (br. s, 1H), 7.56 (t, J=8.1 Hz, 1H), 7.30 (d, J=2.3 Hz, 1H), 7.19-7.27 (m, 2H), 6.97-7.11 (m, 2H), 4.58-4.74 (m, 1H), 3.90-4.07 (m, 3H), 3.67-3.77 (m, 1H), 3.45 (s, 3H), 3.42 (s, 2H), 2.82-2.86 (m, 2H), 2.80 (t, J=6.6 Hz, 2H), 2.68 (s, 3H).

HR LC-MS: MS (ESI, m/z): 496.1664 [M+H$^+$]; t$_R$=0.99 min.

Example 58

1,5-dimethyl-3-(2-{[(S)-2-oxo-3-(3-oxo-3,4-dihydro-2H-pyrido[3,2-b][1,4]thiazin-6-yl)-oxazolidin-5-ylmethyl]-amino}-ethyl)-1H-quinazoline-2,4-dione Starting from the compound of Preparation N and the compound of Preparation M and using Procedure G, the title compound was obtained as a light yellow solid (110 g; 74% yield).

$^1$H NMR (DMSO-d$_6$) δ: 10.78 (br. s, 1H), 7.72 (m, 1H), 7.61 (m, 1H), 7.50-7.60 (m, 1H), 7.22 (d, J=8.5 Hz, 1H), 7.03 (d, J=7.5 Hz, 1H), 4.60-4.76 (m, 1H), 4.02-4.13 (m, 1H), 3.99 (t, J=6.6 Hz, 2H), 3.82 (dd, J=6.6, 10.2 Hz, 1H), 3.51 (s, 2H), 3.45 (s, 3H), 2.82-2.90 (m, 2H), 2.79 (t, J=6.5 Hz, 2H), 2.66 (s, 3H).

HR LC-MS: MS (ESI, m/z): 497.1614 [M+H$^+$]; t$_R$=1.02 min.

Example 59

5-methyl-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione The compound of Preparation O and 6-((S)-5-iodomethyl-2-oxo-oxazolidin-3-yl)-4H-benzo[1,4]thiazin-3-one (prepared according to WO 2008/126034) were reacted according to Procedure F. As the compound thus obtained was not pure enough, it was further reacted with (Boc)$_2$O using Procedure W, purified by CC (DCM/MeOH 19:1) and deprotected with 4M HCl using Procedure U. The title compound was then obtained as a yellowish oil (21 mg; 15% yield).

HR LC-MS: MS (ESI, m/z): 482.1501 [M+H$^+$]; t$_R$=0.95 min.

Example 60

8-methyl-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione The compound of Preparation P and 6-((S)-5-iodomethyl-2-oxo-oxazolidin-3-yl)-4H-benzo[1,4]thiazin-3-one (prepared according to WO 2008/126034) were reacted according to Procedure F. As the compound thus obtained was not pure enough it was reacted with (Boc)$_2$O using Procedure W, purified by CC (DCM/MeOH 19:1) and deprotected with 4M HCl using Procedure U. The title compound was then obtained as a brownish solid (58 mg; 24% yield).

HR LC-MS: MS (ESI, m/z): 482.1498 [M+H$^+$]; t$_R$=0.91 min.

Example 61

8-chloro-1-methyl-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione Starting from 6-((R)-5-aminomethyl-2-oxo-oxazolidin-3-yl)-4H-benzo[1,4]thiazin-3-one (prepared according to WO 2008/126024) and the compound of Preparation Q and using Procedure G, the title compound was obtained as a colourless solid (53 mg; 29% yield).

$^1$H NMR (DMSO-d$_6$) δ: 10.52 (br. s, 1H), 7.99 (dd, J=1.6, 7.8 Hz, 1H), 7.80 (dd, J=1.6, 7.9 Hz, 1H), 7.20-7.32 (m, 3H), 7.01 (dd, J=2.3, 8.5 Hz, 1H), 4.58-4.71 (m, 1H), 3.90-4.04 (m, 3H), 3.70 (dd, J=6.6, 8.7 Hz, 1H), 3.64 (s, 3H), 3.41 (s, 2H), 2.74-2.92 (m, 4H).

HR LC-MS: MS (ESI, m/z): 516.1111 [M+H$^+$]; t$_R$=1.02 min.

Example 62

8-chloro-1-methyl-3-(2-{[(S)-2-oxo-3-(3-oxo-3,4-dihydro-2H-pyrido[3,2-b][1,4]thiazin-6-yl)-oxazolidin-5-ylmethyl]-amino}-ethyl)-1H-quinazoline-2,4-dione Starting from the compound of Preparation N and the compound of Preparation Q and using Procedure G, the title compound was obtained as a light yellow solid (39 mg; 21% yield).

$^1$H NMR (DMSO-d$_6$) δ: 10.80 (br. s, 1H), 7.98 (dd, J=1.6, 7.8 Hz, 1H), 7.79 (dd, J=1.6, 7.9 Hz, 1H), 7.73 (m, 1H), 7.62 (m, 1H), 7.24 (t, J=7.8 Hz, 1H), 4.61-4.74 (m, 1H), 4.03-4.12 (m, 1H), 3.99 (td, J=2.2, 6.6 Hz, 2H), 3.75-3.86 (m, 1H), 3.65 (s, 3H), 3.50 (s, 2H), 2.74-2.89 (m, 4H).

HR LC-MS: MS (ESI, m/z): 517.1069 [M+H$^+$]; t$_R$=1.04 min.

Example 63 rac-(E)-3-[1-methyl-2,4-dioxo-3-(2-{2-[2-oxo-3-(3-oxo-3,4-dihydro-2H-benzo[1,4]thiazin-6-yl)-oxazolidin-5-yl]-ethylamino}-ethyl)-1,2,3,4-tetrahydro-quinazolin-7-yl]-acrylic acid methyl ester Starting from 6-[5-(2-aminoethyl)-2-oxo-3-oxazolidinyl]-2H-1,4-benzothiazin-3(4H)-one (prepared according to WO 2008/126024) and the compound of Preparation S and using Procedure G, the title compound was obtained as a light yellow solid (50 mg; 26% yield).

$^1$H NMR (CDCl$_3$) δ: 8.22 (d, J=8.1 Hz, 1H), 8.07 (br. s, 1H), 7.72 (d, J=16.0 Hz, 1H), 7.36-7.44 (m, 2H), 7.22-7.30 (m, 2H), 6.94 (dd, J=2.3, 8.5 Hz, 1H), 6.56 (d, J=16.0 Hz, 1H), 4.66-4.82 (m, 1H), 4.19-4.28 (m, 2H), 4.04 (t, J=8.6 Hz, 1H), 3.84 (s, 3H), 3.72 (dd, J=7.1, 8.9 Hz, 1H), 3.63 (s, 3H), 3.49 (s, 2H), 2.93-3.00 (m, 2H), 2.82-2.93 (m, 2H), 1.81-2.08 (m, 2H).

HR LC-MS: MS (ESI, m/z): 580.187 [M+H$^+$]; t$_R$=1.06 min.

Example 64

8-chloro-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione The compound of Preparation R and 6-((S)-5-iodomethyl-2-oxo-oxazolidin-3-yl)-4H-benzo[1,4]thiazin-3-one (prepared according to WO 2008/126034) were reacted according to Procedure F. As the compound thus obtained was not pure enough it was reacted with (Boc)$_2$O using Procedure W, purified by CC (DCM/MeOH 19:1) and deprotected with 4M HCl using Procedure U. The title compound was then obtained as a light yellow solid (70 mg; 32% yield).

$^1$H NMR (DMSO-d$_6$) δ: 10.52 (br. s, 1H), 7.84-7.94 (m, 1H), 7.72-7.83 (m, 1H), 7.23-7.35 (m, 2H), 7.13-7.23 (m, 1H), 7.00-7.10 (m, 1H), 4.60-4.80 (m, 1H), 3.89-4.12 (m, 3H), 3.67-3.81 (m, 1H), 3.42 (s, 2H), 2.78-3.04 (m, 4H), 1.15-1.30 (m, 1H).

HR LC-MS: MS (ESI, m/z): 502.0951 [M+H$^+$]; t$_R$=0.92 min.

Example 65

(E)-3-[1-methyl-2,4-dioxo-3-(2-{[(S)-2-oxo-3-(3-oxo-3,4-dihydro-2H-benzo[1,4]thiazin-6-yl)-oxazolidin-5-ylmethyl]-amino}-ethyl)-1,2,3,4-tetrahydro-quinazolin-7-yl]-acrylic acid methyl ester Starting from 6-((R)-5-aminomethyl-2-oxo-oxazolidin-3-yl)-4H-benzo[1,4]thiazin-3-one (prepared according to WO 2008/126024) and the compound of Preparation S and using Procedure G, the title compound was obtained as a light yellow solid (150 mg; 80% yield).

$^1$H NMR (CDCl$_3$) δ: 8.16 (d, J=8.1 Hz, 1H), 8.07 (br. s, 1H), 7.71 (d, J=16.0 Hz, 1H), 7.39 (dd, J=1.3, 8.2 Hz, 1H), 7.34 (d, J=2.3 Hz, 1H), 7.15-7.23 (m, 2H), 6.84 (dd, J=2.3, 8.6 Hz, 1H), 6.58 (d, J=16.0 Hz, 1H), 4.63-4.80 (m, 1H), 4.15-4.30 (m, 2H), 3.88-3.93 (m, 1H), 3.81-3.88 (m, 1H), 3.84 (s, 3H), 3.57 (s, 3H), 3.39 (s, 2H), 2.88-3.15 (m, 4H).

HR LC-MS: MS (ESI, m/z): 566.1711 [M+H$^+$]; t$_R$=1.04 min.

Example 66

2-(2-{[(R)-2-oxo-3-(3-oxo-3,4-dihydro-2H-benzo[1,4]thiazin-6-yl)-oxazolidin-5-ylmethyl]-amino}-ethyl)-6,7-dihydro-5H-pyrido[3,2,1-#]quinazoline-1,3-dione Starting from 6-((R)-5-aminomethyl-2-oxo-oxazolidin-3-yl)-4H-benzo[1,4]thiazin-3-one (prepared according to WO 2008/126024) and the compound of Preparation T and using Procedure G, the title compound was obtained as a colourless foam (47 mg; 31% yield).

$^1$H NMR (DMSO-d$_6$) δ: 10.52 (br. s, 1H), 7.82 (dd, J=1.6, 7.9 Hz, 1H), 7.45-7.51 (m, 1H), 7.30 (d, J=2.4 Hz, 1H), 7.25 (d, J=8.6 Hz, 1H), 7.09-7.16 (m, 1H), 7.02 (dd, J=2.4, 8.6 Hz, 1H), 4.59-4.73 (m, 1H), 3.85-4.10 (m, 5H), 3.73 (dd, J=6.5, 8.7 Hz, 1H), 3.41 (s, 2H), 2.75-2.93 (m, 6H), 1.87-2.00 (m, 2H).

HR LC-MS: MS (ESI, m/z): 508.1667 [M+H$^+$]; t$_R$=0.99 min.

Example 67

2-(2-{[(S)-2-oxo-3-(3-oxo-3,4-dihydro-2H-pyrido[3,2-b][1,4]thiazin-6-yl)-oxazolidin-5-ylmethyl]-amino}-ethyl)-6,7-dihydro-5H-pyrido[3,2,1-ij]quinazoline-1,3-dione Starting from the compound of Preparation N and the compound of Preparation T and using Procedure G, the title compound was obtained as a colourless foam (26 mg; 17% yield).

$^1$H NMR (DMSO-d$_6$) δ: 10.79 (br. s, 1H), 7.76-7.84 (m, 1H), 7.72 (m, 1H), 7.61 (m, 1H), 7.46 (d, J=6.8 Hz, 1H), 7.11 (t, J=7.6 Hz, 1H), 4.60-4.76 (m, 1H), 3.94-4.15 (m, 3H), 3.85-3.93 (m, 2H), 3.82 (dd, J=6.7, 10.1 Hz, 1H), 3.49 (s, 2H), 2.73-2.97 (m, 6H), 1.87-2.01 (m, 2H).

HR LC-MS: MS (ESI, m/z): 509.1609 [M+H$^+$]; t$_R$=1.01 min.

Example 68

N-[2-(1-methyl-2,4-dioxo-1,4-dihydro-2H-quinazolin-3-yl)-ethyl]-N-[(R)-2-oxo-3-(3-oxo-3,4-dihydro-2H-pyrido[3,2-b][1,4]thiazin-6-yl)-oxazolidin-5-ylmethyl]-acetamide Acetyl chloride (0.009 ml) was added to a solution of the compound of Example 55 (56 mg) and TEA (0.017 ml) in DMF (2 ml). The mixture was stirred at rt overnight. The reaction mixture was partitioned between water and EA/MeOH 9:1. The aq. layer was extracted with EA/MeOH 9:1 and the combined org. layers were washed with brine, dried over MgSO$_4$, filtered and concentrated under reduced pressure. The resulting material was purified by CC (EA/MeOH 19:1) and afforded, after stirring in ether, a slightly yellow solid (175 mg; 42% yield).

MS (ESI, m/z): 525.17 [M+H$^+$].

Example 69

8-chloro-1-methyl-3-(2-{[(S)-2-oxo-3-(3-oxo-3,4-dihydro-2H-pyrido[3,2-b][1,4]oxazin-6-yl)-oxazolidin-5-ylmethyl]-amino}-ethyl)-1H-quinazoline-2,4-dione

69.i. 6-((R)-5-azidomethyl-2-oxo-oxazolidin-3-yl)-4H-pyrido[3,2-b][1,4]oxazin-3-one Starting from methanesulfonic acid (R)-2-oxo-3-(3-oxo-3,4-dihydro-2H-pyrido[3,2-b][1,4]oxazin-6-yl)-oxazolidin-5-ylmethyl ester (prepared according to WO 2010/041194) and using Procedure I, the title compound was obtained as a beige solid (0.198 g; 100% yield).

MS (ESI, m/z): 281.03 [M+H$^+$].

69.ii. 8-chloro-1-methyl-3-(2-{[(S)-2-oxo-3-(3-oxo-3,4-dihydro-2H-pyrido[3,2-b][1,4]oxazin-6-yl)-oxazolidin-5-ylmethyl]-amino}-ethyl)-1H-quinazoline-2,4-dione A solution of the compound of Preparation Q (128 mg, 0.44 mmol, 1.1 eq.) in DCM (4 ml) was treated with PPh$_3$ (126 mg, 0.48 mmol, 1.2 eq.). The clear solution was stirred at rt for 2 h. Intermediate 69.i (101 mg, 0.4 mmol, 1 eq.) was added and the mixture stirred at 40° C. for 2 h. NaBH(OAc)$_3$ (253 mg, 1.2 mmol, 3 eq.) and MeOH (1 ml) were added. The reaction was stirred at rt overnight. The reaction mixture was partitioned between water and DCM/MeOH 9:1 and the org. phase was dried over MgSO$_4$ and concentrated. The residue was purified by CC (DCM/MeOH) followed by trituration with ether to give the desired compound as a colourless solid (35 mg).

MS (ESI, m/z): 501.26 [M+H$^+$].

Pharmacological Properties of the Invention Compounds
In Vitro Assays
Bacterial Growth Minimal Inhibitory Concentrations:
Experimental Methods:

Minimal inhibitory concentrations (MICs; mg/l) were determined in cation-adjusted MuellerHinton Broth by a microdilution method following the description given in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006.

Results:

All Example compounds were tested against several Gram positive and Gram negative bacteria.

Typical antibacterial test results are given in Table 1 hereafter (MIC in mg/l).

TABLE 1

| Example No. | MIC for S. aureus 29213 | Example No. | MIC for S. aureus 29213 |
|---|---|---|---|
| 1 | ≤0.016 | 2 | ≤0.016 |
| 3 | ≤0.016 | 4 | ≤0.25 |
| 5 | ≤0.016 | 6 | 0.031 |
| 7 | ≤0.016 | 8 | ≤0.016 |
| 9 | 0.031 | 10 | 0.063 |
| 11 | 0.063 | 12 | ≤0.016 |
| 13 | ≤0.016 | 14 | ≤0.016 |
| 15 | 0.063 | 16 | 0.031 |
| 17 | 0.125 | 18 | ≤0.016 |
| 19 | ≤0.016 | 20 | 0.125 |
| 21 | ≤0.016 | 22 | ≤0.016 |
| 23 | 0.031 | 24 | ≤0.016 |
| 25 | 0.063 | 26 | 0.031 |
| 27 | 0.063 | 28 | 0.063 |
| 29 | ≤0.016 | 30 | 0.125 |
| 31 | ≤0.016 | 32 | 0.031 |
| 33 | 0.125 | 34 | 0.063 |
| 35 | 0.125 | 36 | 0.031 |
| 37 | 0.5 | 38 | 0.063 |
| 39 | 0.25 | 40 | ≤0.016 |
| 41 | 0.25 | 42 | 0.031 |
| 43 | ≤0.016 | 44 | ≤0.016 |
| 45 | ≤0.016 | 46 | ≤0.016 |
| 47 | 0.063 | 48 | 0.031 |
| 49 | 1 | 50 | 0.125 |
| 51 | ≤0.016 | 52 | 0.063 |
| 53 | 0.5 | 54 | 1 |
| 55 | 0.031 | 56 | 0.125 |
| 57 | ≤0.016 | 58 | ≤0.016 |
| 59 | 0.25 | 60 | 0.25 |
| 61 | ≤0.016 | 62 | ≤0.016 |
| 63 | 0.031 | 64 | 0.25 |
| 65 | 0.125 | 66 | 0.031 |
| 67 | ≤0.016 | 68 | 0.25 |
| 69 | 0.031 | | |

The invention claimed is:

1. A compound of formula I

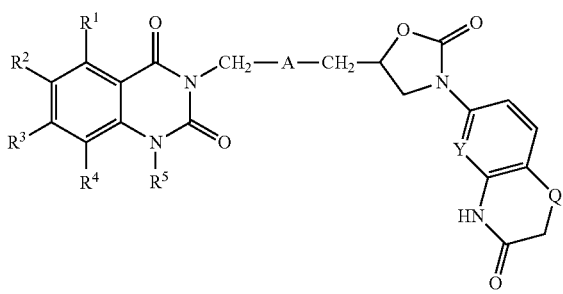

I wherein
$R^1$ is H, halogen, ($C_1$-$C_3$)alkyl or ($C_1$-$C_3$)alkoxy;
$R^2$ is H, halogen, ($C_1$-$C_3$)alkyl, ($C_1$-$C_3$)alkoxy or pyrrolidin-1-yl;
$R^3$ is H, halogen, ($C_1$-$C_3$)alkyl, ($C_1$-$C_3$)alkoxy, vinyl or 2-methoxycarbonylvinyl or $R^2$ and $R^3$ together with the two carbon atoms which bear them form a phenyl ring;
$R^4$ is H, halogen, ($C_1$-$C_3$)alkyl or ($C_1$-$C_3$)alkoxy and $R^5$ is H, ($C_1$-$C_3$)alkyl or cyclopropyl, or $R^4$ and $R^5$ form together a —$CH_2CH_2CH_2$— group;

A is the divalent group —$CH_2$—, —$CH_2CH_2$—, #-CH(OH)$CH_2$-*, #-$CH_2$N($R^6$)-* or —$CH_2$NH$CH_2$—, wherein # indicates the point of attachment to the optionally substituted (quinazoline-2,4-dione -3-yl)methyl residue and * represents the point of attachment to the substituted (oxazolidinon-4-yl)methyl residue;
$R^6$ is H or acetyl;
Y is CH or N; and
Q is O or S;
or a salt of such a compound.

2. The compound according to claim 1, wherein A is the divalent group —$CH_2$—;
or a salt of such a compound.

3. The compound according to claim 1, wherein A is the divalent group #-$CH_2$NH-*;
or a salt of such a compound.

4. The compound according to one claims 1 wherein each of $R^2$ and $R^3$ is H;
or a salt of such a compound.

5. The compound according to claim 1 wherein $R^5$ is methyl;
or a salt of such a compound.

6. The compound according to claim 1, wherein:
A is —$CH_2$—or #-$CH_2$NH-*;
one of $R^1$ and $R^4$ is independently halogen or ($C_1$-$C_3$)alkyl and the other is H or each of $R^1$ and $R^4$ is independently halogen;
each of $R^2$ and $R^3$ is H; and
$R^5$ is methyl;
or a salt of such a compound.

7. The compound according to claim 6, wherein:
A is —$CH_2$—; and
one of $R^1$ and $R^4$ is independently chlorine or methyl and the other is H or each of $R^1$ and $R^4$ is chlorine;
or a salt of such a compound.

8. The compound according to claims 1, wherein Y is CH;
or a salt of such a compound.

9. A The compound according to claim 1, wherein Y is N;
or a salt of such a compound.

10. The compound according to claim 1, wherein the compound is:
3-{3-[(S)-2-oxo-3-(3-oxo-3,4-dihydro-2H -benzo[1,4]thiazin-6-yl-oxazolidin-5-yl]-propyl}-1H-quinazoline-2,4-dione;
1-methyl-3-{3-[(S)-2-oxo-3-(3-oxo-3,4-dihydro -2H-pyrido[3,2-b][1,4]thiazin-6-yl-oxazolidin-5-yl]-propyl}-1H-quinazoline-2,4-dione;
1-methyl-3-{3-[(S)-2-oxo-3-(3-oxo-3,4-dihydro -2H-benzo[1,4]thiazin-6-yl)-oxazolidin -5-yl]-propyl}11H-quinazoline-2,4-dione;
3-{3-[(R)-2-oxo-3-(3-oxo-3,4-dihydro-2H-benzo [1,4]thiazin-6-yl)-oxazolidin-5-yl]-propyl}1-propyl-1H-quinazoline-2,4-dione;
5-methyl -3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;
1,5-dimethyl-3-{3-[(S)-2-oxo-3-(3-oxo-3,4-dihydro-2H-benzo [1,4]thiazin-6-yl)-oxazolidin-5-yl]-propyl}-1H-quinazoline-2,4-dione;
5-methyl-3-{3-[(S)-2-oxo-3-(3-oxo-3,4-dihydro -2H-benzo [1,4]thiazin-6-yl)-oxazolidin-5-yl]-propyl}-1H-quinazoline-2,4-dione;
5-methyl-3-{3-[(S)-2-oxo-3-(3-oxo-3,4-dihydro -2H-pyrido[3,2-b][1,4]thiazin-6-yl)-oxazolidin -5-yl]-propyl}-1H-quinazoline-2,4-dione;

5-methyl-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione;

6-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

7-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

8-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

8-methyl-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;

8-methyl-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione;

8-methyl-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione;

5-chloro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

5-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

5-chloro-3-{3-[(5)-2-oxo-3-(3-oxo-3,4-dihydro-2H-benzo[1,4]thiazin-6-yl-oxazolidin-5-yl]-propyl}-1H-quinazoline-2,4-dione;

5-chloro-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione;

5-chloro-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione;

8-chloro-3-{3-[(R)-2-oxo-3-(3-oxo-3,4-dihydro-2H-benzo[1,4]thiazin-6-yl-oxazolidin-5-yl]-propyl}-1H-quinazoline-2,4-dione;

8-chloro-3-{3-[(S)-2-oxo-3-(3-oxo-3,4-dihydro-2H-pyrido[3,2-b][1,4]thiazin-6-yl)-oxazolidin-5-yl]-propyl}-1H-quinazoline-2,4-dione;

8-chloro-3-{3-[(R)-2-oxo-3-(3-oxo-3,4-dihydro-2H-pyrido[3,2-b][1,4]oxazin-6-yl)-oxazolidin-5-yl]-propyl}-1H-quinazoline-2,4-dione;

8-chloro-3-{3-[(S)-2-oxo-3-(3-oxo-3,4-dihydro-2H-pyrido[3,2-b][1,4]oxazin-6-yl)-oxazolidin-5-yl]-propyl}-1H-quinazoline-2,4-dione;

6-chloro-3-{3-[(R)-2-oxo-3-(3-oxo-3,4-dihydro-2H-benzo[1,4]thiazin-6-yl-oxazolidin-5-yl]-propyl}1-1H-quinazoline-2,4-dione;

6-fluoro-3-{3-[(R)-2-oxo-3-(3-oxo-3,4-dihydro-2H-benzo[1,4]thiazin-6-yl)-oxazolidin-5-yl]-propyl}1-1H-quinazoline-2,4-dione;

7-chloro-3-{3-[(R)-2-oxo-3-(3-oxo-3,4-dihydro-2H-benzo[1,4]thiazin-6-yl)-oxazolidin-5-yl]-propyl}1-1H-quinazoline-2,4-dione;

7-fluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

8-chloro-3-{3-[(S)-2-oxo-3-(3-oxo-3,4-dihydro-2H-benzo[1,4]thiazin-6-yl-oxazolidin-5-yl]-propyl}-1H-quinazoline-2,4-dione;

8-chloro-1-methyl-3-(2-{2-[(R)-2-oxo-3-(3-oxo-3,4-dihydro-2H-benzo[1,4]thiazin-6-yl)-oxazolidin-5-yl]-ethylamino}-ethyl)-1H-quinazoline-2,4-dione;

8-chloro-1-methyl-3-{3-[(S)-2-oxo-3-(3-oxo-3,4-dihydro-2H-benzo[1,4]thiazin-6-yl)-oxazolidin-5-yl]-propyl}1-1H-quinazoline-2,4-dione;

8-fluoro-3-{3-[(R)-2-oxo-3-(3-oxo-3,4-dihydro-2H-benzo[1,4]thiazin-6-yl)-oxazolidin-5-yl]-propyl}1-1H-quinazoline-2,4-dione;

5-methoxy-3-{3-[(R)-2-oxo-3-(3-oxo-3,4-dihydro-2H-benzo[1,4]thiazin-6-yl)-oxazolidin-5-yl]-propyl}1-1H-quinazoline-2,4-dione;

6-methoxy-3-{3-[(R)-2-oxo-3-(3-oxo-3,4-dihydro-2H-benzo[1,4]thiazin-6-yl)-oxazolidin-5-yl]-propyl}1-1H-quinazoline-2,4-dione;

7-methoxy-3-{3-[(S)-2-oxo-3-(3-oxo-3,4-dihydro-2H-benzo[1,4]thiazin-6-yl)-oxazolidin-5-yl]-propyl}1-1H-quinazoline-2,4-dione;

8-methoxy-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

3-{3-[(S)-2-oxo-3-(3-oxo-3,4-dihydro-2H-benzo[1,4]thiazin-6-yl)-oxazolidin-5-yl]-propyl}-6-pyrrolidin-1-yl-1H-quinazoline-2,4-dione;

6,7-difluoro-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

6,7-dimethoxy-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

5,8-dichloro-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;

2-{3-[(R)-2-oxo-3-(3-oxo-3,4-dihydro-2H-benzo[1,4]thiazin-6-yl)-oxazolidin-5-yl]-propyl}-6,7-dihydro-5H-pyrido[3,2,1-ij]quinazoline-1,3-dione;

3-{3-[(S)-2-oxo-3-(3-oxo-3,4-dihydro-2H-benzo[1,4]thiazin-6-yl)-oxazolidin-5-yl]-propyl}-1H-benzo[g]quinazoline-2,4-dione;

1-cyclopropyl-6,7-difluoro-8-methoxy-3-{3-[(S)-2-oxo-3-(3-oxo-3,4-dihydro-2H-benzo[1,4]thiazin-6-yl)-oxazolidin-5-yl]-propyl}-1H-quinazoline-2,4-dione;

2-{3-[(S)-2-oxo-3-(3-oxo-3,4-dihydro-2H-benzo[1,4]thiazin-6-yl)-oxazolidin-5-yl]-propyl}-6,7-dihydro-5H-pyrido[3,2,1-ij]quinazoline-1,3-dione;

2-{3-[(S)-2-oxo-3-(3-oxo-3,4-dihydro-2H-pyrido[3,2-b][1,4]oxazin-6-yl)-oxazolidin-5-yl]-propyl}-6,7-dihydro-5H-pyrido[3,2,1-ij]quinazoline-1,3-dione;

7-bromo-1-methyl-3-{3-[(R)-2-oxo-3-(3-oxo-3,4-dihydro-2H-benzo[1,4]thiazin-6-yl)-oxazolidin-5-yl]-propyl}-1H-quinazoline-2,4-dione;

1-methyl-3-{3-[(R)-2-oxo-3-(3-oxo-3,4-dihydro-2H-benzo[1,4]thiazin-6-yl)-oxazolidin-5-yl]-propyl}-7-vinyl-1H-quinazoline-2,4-dione;

3-{4-[2-oxo-3-(3-oxo-3,4-dihydro-2H-benzo[1,4]thiazin-6-yl)-oxazolidin-5-yl]-butyl}-1H-quinazoline-2,4-dione;

3-{2-hydroxy-4-[(S)-2-oxo-3-(3-oxo-3,4-dihydro-2H-benzo[1,4]oxazin-6-yl)-oxazolidin-5-yl]-butyl}1-methyl-1H-quinazoline-2,4-dione;

3-{(R)-2-hydroxy-4-[(R)-2-oxo-3-(3-oxo-3,4-dihydro-2H-pyrido[3,2-b][1,4]thiazin-6-yl)-oxazolidin-5-yl]-butyl}1-methyl-1H-quinazoline-2,4-dione;

1-methyl-3-{4-[(R)-2-oxo-3-(3-oxo-3,4-dihydro-2H-pyrido[3,2-b][1,4]thiazin-6-yl)-oxazolidin-5-yl]-butyl}-1H-quinazoline-2,4-dione;

1-methyl-3-{4-[(R)-2-oxo-3-(3-oxo-3,4-dihydro-2H-pyrido[3,2-b][1,4]oxazin-6-yl)-oxazolidin-5-yl]-butyl}1-1H-quinazoline-2,4-dione;

3-(2-{[(R)-2-oxo-3-(3-oxo-3,4-dihydro-2H -pyrido[3,2-b][1,4]thiazin-6-yl)-oxazolidin -5-ylmethyl]-amino}-ethyl)-1H-quinazoline-2,4-dione;

3-(2-{[(R)-2-oxo-3-(3-oxo-3,4-dihydro-2H-benzo [1,4] thiazin-6-yl)-oxazolidin-5-ylmethyl]-amino}-ethyl)-1H-quinazoline-2,4-dione;

1-methyl-3-(2-{[(R)-2-oxo-3-(3-oxo-3,4-dihydro-2H-pyrido[3,2-b][1,4]thiazin-6-yl) -oxazolidin-5-ylmethyl]-amino}-ethyl)-1H-quinazoline-2,4-dione;

1-methyl-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione;

1,5-dimethyl-3-(2-{[(R)-2-oxo-3-(3-oxo-3,4-dihydro-2H-benzo[1,4]thiazin-6-yl)-oxazolidin-5-ylmethyl]-amino }1-ethyl)-1H-quinazoline-2,4-dione;

1,5-dimethyl-3-(2-{[(S)-2-oxo-3-(3-oxo-3,4-dihydro-2H-pyrido[3,2-b][1 ,4]thiazin-6-yl) -oxazolidin-5-ylmethyl]-amino}-ethyl)-1H-quinazoline-2,4-dione;

5-methyl-3-(2-{[(R)-2-oxo-3-(3-oxo-3,4-dihydro-2H-benzo[1,4]thiazin-6-yl)-oxazolidin-5-ylmethyl]-amino }-ethyl)-1H-quinazoline-2,4-dione;

8-methyl-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione;

8-chloro-1 -methyl-3-(2-{[(R)-2-oxo-3-(3-oxo -3,4-dihydro-2H-benzo[1,4]thiazin-6-yl) -oxazolidin-5-ylmethyl]-amino}-ethyl)-1H-quinazoline-2,4-dione;

8-chloro-1-methyl-3-(2-{[(S)-2-oxo-3-(3-oxo -3,4-dihydro-2H-pyrido[3,2-b][1,4]thiazin-6-yl) -oxazolidin-5-ylmethyl]-amino}-ethyl)-1H-quinazoline-2,4-dione;

(E)-3-[1-methyl-2,4-dioxo-3-(2-{[2-oxo-3-(3-oxo-3,4-dihydro-2H-benzo[1,4]thiazin-6-yl) -oxazolidin-5-yl]-ethylamino}-ethyl)-1,2,3,4-tetrahydro-quinazolin-7-yl]-acrylic acid methyl ester;

8-chloro-3-(2-{[(R)-2-oxo-3-(3-oxo-3,4-dihydro-2H-benzo[1,4]thiazin-6-yl)-oxazolidin-5-ylmethyl]-amino}-ethyl)-1H-quinazoline-2,4-dione;

(E)-3-[1-methyl-2,4-dioxo-3-(2-{[(S)-2-oxo-3-(3-oxo-3, 4-dihydro-2H-benzo[1,4]thiazin-6-yl) -oxazolidin-5-ylmethyl]-amino}-ethyl)-1,2,3,4-tetrahydro-quinazolin-7-yl]acrylic acid methyl ester;

2-(2-{[(R)-2-oxo-3-(3-oxo-3,4-dihydro-2H -benzo[1,4] thiazin-6-yl)-oxazolidin-5-ylmethyl]-amino}-ethyl)-6, 7-dihydro-5H-pyrido [3,2,1-ij]quinazoline-1,3-dione;

2-(2-{[(S)-2-oxo-3-(3-oxo-3,4-dihydro-2H -pyrido[3,2-b] [1,4]thiazin-6-yl)-oxazolidin -5-ylmethyl]-amino}-ethyl)-6,7-dihydro-5H-pyrido [3,2,1-ij]quinazoline-1 ,3-dione;

N-[2-(1-methyl-2,4-dioxo-1,4-dihydro-2H-quinazolin-3-yl)-ethyl]-N-[(R)-2-oxo-3-(3-oxo-3,4-dihydro-2H-pyrido [3,2-b][1,4]thiazin-6-yl)-oxazolidin-5-ylmethyl]-acetamide; or 8-chloro-l-methyl-3-(2-{[(S)-2-oxo-3-(3-oxo-3,4-dihydro-2H-pyrido[3,2-b][1,4]oxazin-6-yl) -oxazolidin-5-ylmethyl]-amino}-ethyl)-1H-quinazoline-2,4-dione;

or a salt of such a compound.

11. A medicament comprising the compound according to 1,or a pharmaceutically acceptable salt thereof.

12. A pharmaceutical composition comprising, as an active principle, the compound according to claim 1, or a pharmaceutically acceptable salt thereof, and at least one therapeutically inert excipient.

13. A method for treatment or prevention of bacterial infection comprising administering to a subject in need thereof a therapeutic amount of the compound according to claims 1, or a pharmaceutically acceptable salt thereof.

14. The method according to claim 13, wherein the bacterial infection comprises respiratory tract infections, otitis media, meningitis, skin and soft tissue infections, pneumonia, bacteremia, endocarditis, intraabdominal infections, gastrointestinal infections, *Clostridium difficile* infections, urinary tract infections, sexually transmitted infections, foreign body infections, osteomyelitis, lyme disease, topical infections, opthalmological infections, tuberculosis and tropical diseases.

15. The method according to claim 13, wherein the bacterial infection comprises respiratory tract infections, otitis media, meningitis, skin and soft tissue infections, pneumonia and bacteremia.

* * * * *